(12) United States Patent
Bondy et al.

(10) Patent No.: US 10,202,353 B2
(45) Date of Patent: Feb. 12, 2019

(54) THERAPEUTIC COMPOUNDS

(71) Applicant: Gilead Sciences, Inc., Foster City, CA (US)

(72) Inventors: Steven S. Bondy, Haiku, HI (US); Chien-Hung Chou, Dublin, CA (US); John O. Link, San Francisco, CA (US); Winston C. Tse, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 17 days.

(21) Appl. No.: 15/121,643

(22) PCT Filed: Feb. 26, 2015

(86) PCT No.: PCT/US2015/017820
§ 371 (c)(1),
(2) Date: Aug. 25, 2016

(87) PCT Pub. No.: WO2015/130964
PCT Pub. Date: Sep. 3, 2015

(65) Prior Publication Data
US 2016/0368881 A1  Dec. 22, 2016

Related U.S. Application Data

(60) Provisional application No. 61/946,669, filed on Feb. 28, 2014.

(51) Int. Cl.
| | |
|---|---|
| *C07D 403/12* | (2006.01) |
| *C07D 231/56* | (2006.01) |
| *C07D 231/54* | (2006.01) |
| *C07D 401/12* | (2006.01) |
| *C07D 409/12* | (2006.01) |
| *C07D 417/12* | (2006.01) |
| *C07D 491/10* | (2006.01) |
| *A61K 31/357* | (2006.01) |
| *A61K 31/416* | (2006.01) |
| *A61K 31/4162* | (2006.01) |
| *A61K 31/4178* | (2006.01) |
| *A61K 31/427* | (2006.01) |
| *A61K 31/4439* | (2006.01) |
| *A61K 31/522* | (2006.01) |
| *A61K 45/06* | (2006.01) |
| *C07D 319/08* | (2006.01) |
| *C07D 405/12* | (2006.01) |
| *C07D 473/06* | (2006.01) |
| *C07D 491/113* | (2006.01) |

(52) U.S. Cl.
CPC .......... *C07D 231/56* (2013.01); *A61K 31/357* (2013.01); *A61K 31/416* (2013.01); *A61K 31/4162* (2013.01); *A61K 31/4178* (2013.01); *A61K 31/427* (2013.01); *A61K 31/4439* (2013.01); *A61K 31/522* (2013.01); *A61K 45/06* (2013.01); *C07D 231/54* (2013.01); *C07D 319/08* (2013.01); *C07D 401/12* (2013.01); *C07D 403/12* (2013.01); *C07D 405/12* (2013.01); *C07D 409/12* (2013.01); *C07D 417/12* (2013.01); *C07D 473/06* (2013.01); *C07D 491/10* (2013.01); *C07D 491/113* (2013.01)

(58) Field of Classification Search
None
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,663,159 A | 9/1997 | Starrett, Jr. et al. |
| 5,792,756 A | 8/1998 | Starrett, Jr. et al. |
| 8,263,627 B2 | 9/2012 | Barrow et al. |
| 8,748,412 B2 | 6/2014 | Liao et al. |
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,220,710 B2 | 12/2015 | Bondy et al. |
| 9,540,343 B2 | 1/2017 | Bondy et al. |
| 9,789,089 B2 | 10/2017 | Bondy et al. |

(Continued)

FOREIGN PATENT DOCUMENTS

| | | |
|---|---|---|
| WO | WO-1991/019721 A1 | 12/1991 |
| WO | WO-2004/050643 A2 | 6/2004 |

(Continued)

OTHER PUBLICATIONS

Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem. 39(25):4958-4965.

(Continued)

*Primary Examiner* — Nyeemah A Grazier

(57) ABSTRACT

Compounds of Formula I, or salts thereof, are disclosed. Also disclosed are pharmaceutical compositions comprising a compound of Formula I, processes for preparing compounds of Formula I, intermediates useful for preparing compounds of Formula I and therapeutic, methods for treating a Retroviridae viral infection, in particular infection caused by the HIV virus.

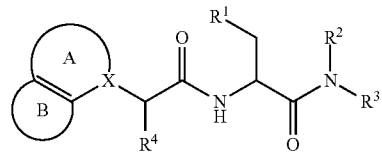

I

45 Claims, No Drawings

(56) References Cited

U.S. PATENT DOCUMENTS

| | | | |
|---|---|---|---|
| 2005/0282805 | A1 | 12/2005 | Hangeland et al. |
| 2007/0032469 | A1 | 2/2007 | Isaac et al. |
| 2007/0083045 | A1 | 4/2007 | Di Francesco et al. |
| 2010/0249176 | A1 | 9/2010 | Barrow et al. |
| 2012/0045761 | A1 | 2/2012 | Jagannath et al. |
| 2013/0165489 | A1 | 6/2013 | Cocklin et al. |
| 2014/0021347 | A1 | 1/2014 | Ominami et al. |
| 2014/0142085 | A1 | 5/2014 | Bondy et al. |
| 2014/0221346 | A1 | 8/2014 | Halcomb et al. |
| 2014/0221417 | A1 | 8/2014 | Bondy et al. |
| 2014/0221421 | A1 | 8/2014 | Bondy et al. |
| 2014/0296266 | A1 | 10/2014 | Hu et al. |
| 2014/0303164 | A1 | 10/2014 | Brizgys et al. |
| 2016/0067224 | A1 | 3/2016 | Bondy et al. |
| 2016/0083368 | A1 | 3/2016 | Brizgys et al. |
| 2016/0108030 | A1 | 4/2016 | Brizgys et al. |
| 2016/0368881 | A1 | 12/2016 | Bondy et al. |
| 2017/0137405 | A1 | 5/2017 | Bondy et al. |
| 2018/0051005 | A1 | 2/2018 | Graupe et al. |

FOREIGN PATENT DOCUMENTS

| | | |
|---|---|---|
| WO | WO-2005/123680 A1 | 12/2005 |
| WO | WO-2008/013622 A2 | 1/2008 |
| WO | WO-2009/005677 A2 | 1/2009 |
| WO | WO-2009/010804 A1 | 1/2009 |
| WO | WO-2009/062285 A1 | 5/2009 |
| WO | WO-2010/130034 A1 | 11/2010 |
| WO | WO-2011/059887 A1 | 5/2011 |
| WO | WO-2011/143772 A1 | 11/2011 |
| WO | WO-2012/003497 A1 | 1/2012 |
| WO | WO-2012/003498 A1 | 1/2012 |
| WO | WO-2012/065062 A1 | 5/2012 |
| WO | WO-2012065062 A1 | 5/2012 |
| WO | WO-2012/145728 A1 | 10/2012 |
| WO | WO-2013/006792 A1 | 1/2013 |
| WO | WO-2013006738 A1 | 1/2013 |
| WO | WO-2013/159064 A1 | 10/2013 |
| WO | WO-2014/016358 A1 | 1/2014 |
| WO | WO-2014/028931 A2 | 2/2014 |
| WO | WO-2014/110298 A1 | 7/2014 |
| WO | WO-2014110298 A1 | 7/2014 |
| WO | WO-2014/134566 A2 | 9/2014 |
| WO | WO-2015/008097 A1 | 1/2015 |
| WO | WO-2015/061518 A1 | 4/2015 |
| WO | WO-2015/130966 A1 | 9/2015 |
| WO | WO-2016/040084 A1 | 3/2016 |
| WO | WO-2016/172424 A1 | 10/2016 |
| WO | WO-2016/172425 A1 | 10/2016 |

OTHER PUBLICATIONS

Berge, S.M. et al. (1977) "Pharmaceutical Salts," *J. Pharma. Sci.* 66(1):1-19.

Bhattacharya et al. (2014) Structural Basis of HIV-1 Capsid Recognition by PF74 and CPSF6, *PNAS*; 111(52):18625-18630.

Blair et al., (2010) "HIV Capsid is a Tractable Target for Small Molecule Therapeutic Intervention," *PLoS Pathog.* 6(12): e1001220.

Briggs et al., (2003) "Structural Organization of Authentic, Mature HIV-1 Virions and Cores," *The EMBO Journal*; vol. 22 No. 7 pp. 1707-1715.

Brown, M.K. et al. ( 2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," *Angew Chem. Int. Ed. Engl.* 44(33):5306-5310.

Bundgaard, H. (1991). "Design and Application of Prodrugs," Chapter 5 in a Textbook of Drug Design and Development, Krogsgaard-Larsen, P. et al. eds., Harwood Academic Publishers, Chur, Switzerland, pp. 113-191.

Campbell et al., (2015) "HIV-1 Capsid: The Multifaceted Key Player in HIV-1 Infection," *Nat Rev Microbiol.*; 13(8): 471-483.

Chin et al. (2015) "Direct Visualization of HIV-1 Replication Intermediates Shows That Capsid and CPSF6 Modulate HIV-1 Intra-Nuclear Invasion and Integration", *Cell Reports* 13:1717-1731.

Cos, P. et al. (1998) "Structure-Activity Relationship and Classification of Flavonoids as Inhibitors of Xanthine Oxidase and Superoxide Seavengers," J. Natl. Prod. 61:71-76.

Cossy, J. et al. (1995) "Ring Opening of Cyclopropylketones Induced by Photochemical Electron Transfer," Tetrahedron 51(43):11751-11764.

Curreli et al., (2011) "Virtual Screening Based Identification of Novel Small-molecule Inhibitors Targeted to the HIV-1 Capsid," *Bioorganic & Medicinal Chemistry* 19:77-90.

De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.

Fader et al., (2013) Optimization of a 1,5-dihydrobenzo[b][1,4]diazepine-2,4-dione Series of HIV Capsid Assembly Inhibitors 2: Structure-Activity Relationships (SAR) of the C3-Phenyl Moiety, *Bioorganic & Medicinal Chemistry Letters*, doi: <http://dx.doi.org/10.1016/j.bmcl.2013.03.074>.

Forshey et al., (2002) "Formation of a Human Immunodeficiency Virus Type 1 Core of Optimal Stability Is Crucial for Viral Replication," *J. Virology*, 76(11) p. 5667-5677.

Ganser et al., (1999) "Assembly and Analysis of Conical Models for the HIV-1 Core," *Science* 283, 80-82.

Ganser-Pornillos et al., (2007) "Structure of Full-Length HIV-1 CA: A Model for the Mature Capsid Lattice," Cell.; 131(1):70-9.

Hammer, S.M. et al. (2008) "Antiretroviral Treatment of Adult HIV Infection: 2008 Recommendations of the International AIDS Society-USA Panel," JAMA 300(5):555-570.

Hodgson, D.M. et al. (2007) "Intramolecular Cyclopropanation of Unsaturated Terminal Epoxides and Chlorohydrins," *JACS* 129(14):4456-4462.

Hung et al. (2013) "Large-Scale Functional Purification of Recombinant HIV-1 Capsid" *PLOS One*, vol. 8, Issue 3, e58035.

International Search Report and Written Opinion dated Mar. 11, 2014 for PCT/US2014/010938.

International Search Report and Written Opinion dated Apr. 11, 2014 for PCT/US2014/010937.

International Search Report and Written Opinion dated Oct. 14, 2014 for PCT/US2014/019663.

International Search Report and Written Opinion dated Sep. 19, 2012 for PCT/US2012/045630.

Internationl Search Report and Written Opinion dated Mar. 21, 2014 for PCT/US2014/010939.

Jeong, .J.U. (2010) "Synthesis of Tetrasubstituted Pyrazones and Pyrazone N-Oxides," *Tetrahedron Letters* 51(6):974-976.

Jin et al., (2010) "SAR and Molecular Mechanism Study of Novel Acylhydrazone Compounds Targeting HIV-1 CA," Bioorganic & Medicinal Chemistry; 18: 2135-2140.

Jouvenet et al., (2006) "Plasma Membrane Is the Site of Productive HIV-1 Particle Assembly," *PLoS Biol.*;4(12):e435.

Kelly, et al., (2007) "Structure of the Antiviral Assembly Inhibitor CAP-1 Bound to the HIV-1 CA Protein," *Journal of Molecular Biology*, doi: 10.1016/j.jmb.2007.07.070.

Kim et al., (2013) "Discovery of a New HIV-1 Inhibitor Scaffold and Synthesis of Potential Prodrugs of Indazoles," *Bioorganic & Medicinal Chemistry Letters*, doi: <http://dx.doi.org/10.1016/j.bmcl.2013.03.075>.

Kocienski, P.J. (1994). "Protecting Groups: An Overview," Chapter 1 in *Protecting Groups*, Thieme Publishing Group: New York, NY, pp. 1-20.

Lad et al., (2015) "Functional Label-Free Assays for Characterizing the in Vitro Mechanism of Action of Small Molecule Modulators of Capsid Assembly" *Biochemistry*, 54, 2240-2248.

Lamorte et al. (2015) "Discovery of Novel Small-Molecule HIV-1 Replication Inhibitors That Stabilize Capsid Complexes" *Antimicrobial Agents and Chemotherapy*, 57(10): 4622-4631.

Lazerwith et al., (2017) "New Antiretrovirals for HIV and Antivirals for HBV," in Comprehensive Medicinal Chemistry, 3rd Edition, 1-36.

(56) References Cited

OTHER PUBLICATIONS

Lee et al., (2010) "Flexible Use of Nuclear Import Pathways by HIV-1," *Cell Host & Microbe*; 7, 221-233.

Lemke, C.T. et al. (2012) "Distinct Effects of Two HIV-1 Capsid Assembly Inhibitor Families That Bind the Same Site Within the N-Terminal Domain of the Viral CA Protein," J. Virol. 86(12):6643-6655.

Matreyek et al., (2013) "Nucleoporin NUP153 Phenylalanine-Glycine Motifs Engage a Common Binding Pocket within the HIV-1 Capsid Protein to Mediate Lentiviral Infectivity" *PLOS Pathogens* vol. 9 | Issue 10 | e1003693.

Pornillos et al., (2009) Supplemental Data for "X-ray Structures of the Hexameric Building Block of the HIV Capsid" Cell. Jun. 26, 2009;137(7):1282-92.

Powers, J.J. et al. (2009) "Synthesis of Methyl-, Fluoro-, and Chloro-Substituted 6-Hydroxyisoindolin-1-Ones," *Tetrahedron Letters* 50(12):1267-1269.

Price et al. (2012) "CPSF6 Defines a Conserved Capsid Interface That Modulates HIV-1 Replication" *PLOS Pathogens*, 8(8):e1002896.

Puech, F. et al. (Oct. 1993). "Intracellular Delivery of Nucleoside Monophosphates Through a Reductase-Mediated Activation Process," Antiviral Res. 22(2-3):155-174.

Rihn et al., (2013) "Extreme Genetic Fragility of the HIV-1 Capsid" *PLOS One*, vol. 9 Issue 6 e1003461.

Siddiqui, A. et al. (1999) "The Presence of SUbstituents on the Aryl Moiety of the Aryl Phosphoramidate Derivative of d4T Enhances Anti-HIV Efficacy in Cell Culture: A Structure-Activity Relationship" J. Med. Chem. 42:393-399.

Smith, R.J. et al. (2010) "Evolutionary Dynamics of Complex Networks of HIV Drug-Resistant Strains: The Case of San Francisco," Science 327(5966):697-701.

Sticht et al., (2005) "A peptide inhibitor of HIV-1 assembly in vitro" *Nature Structural & Molecular Biology*, vol. 12 No. 8 671-677.

Taiwo, B. (2009) "Understanding Transmitted HIV Resistance Through the Experience in the USA," *Int. J. Infect. Dis.* 13(5):552-559.

Tanaka, R. et al. (2005) "One-Pot Synthesis of Metalated Pyridines from Two Acetylenes, a Nitrile, and a Titanium(II) Alkoxide," *J. Am. Chem. Soc.* 127(21):7774-7780.

Tang et al., (2003) "Antiviral Inhibition of the HIV-1 Capsid Protein," *J. Mol. Biol.*, 327, 1013-1020.

Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA.

Tsiang et al., (2012) "A Trimer of Dimers Is the Basic Building Block for Human Immunodeficiency Virus-1 Capsid Assembly" *Biochemistry*, 51, 4416-4428.

Wong et al., (2014) "SPR Assay Development to Characterize Capsid Inhibitors Binding & MOA," Poster Presented at the Developments in Protein Interaction (DiPIA), La Jolla, CA.

Yant et al., (2014) "An Improved PF74 Analog Inhibits Multiple HIV Capsid Functions Independently of Host Cyclophilin a and CPSF6" Poster Presented at the Conference on Retroviruses and Opportunistic Infections (CROI), Boston, Massachusetts.

IPRP for International Application No. PCT/US2015/017820 dated Sep. 6, 2016.

Search Report and Written Opinion for International Application No. PCT/US2015/017820 dated May 13, 2015.

Shi et al. "Small-Molecule Inhibition of Human Immunodeficiency Virus Type 1 Infection by Virus Capsid Destabilization" *Journal of Virology* 85(1) 542-549.

THERAPEUTIC COMPOUNDS

CROSS REFERENCE TO RELATED APPLICATIONS

This patent application is a national stage filing under 35 U.S.C. § 371 of International Patent Application No. PCT/US2015/017820, filed on Feb. 26, 2015, which claims the benefit of priority of U.S. Provisional Patent Application Ser. No. 61/946,669, filed Feb. 28, 2014. The contents of each application is incorporated by reference.

BACKGROUND

Positive-single stranded RNA viruses comprising the Retroviridae family include those of the subfamily Orthoreirovirinae and genera *Alpharetrovirus, Betaretrovirus, Gamaretrovirus, Deltaretrovirus, Epsilonretrovirus, Lentivirus*, and *Spumavirus* which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J. et al. *Science* 2010, 327: 697-701). Therefore, there is a need to discover new antiretroviral agents.

SUMMARY

In one aspect, the present disclosure provides a compound of Formula (I):

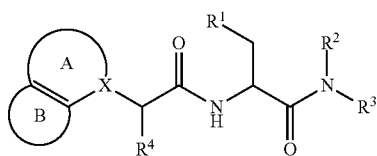

wherein:

ring A, including the two carbon atoms to which it is fused to ring B, is a 5-6 membered monocyclic heteroaryl or phenyl, wherein any 5-6 membered heteroaryl or phenyl of A is optionally substituted with 1, 2, or 3 $Z^1$ groups, wherein the $Z^1$ groups are the same or different;

ring B, including the two carbon atoms to which it is fused to ring A, is a 5-7 membered monocyclic carbocycle, 6-10 membered bicyclic carbocycle, 5-7 membered monocyclic heterocycle, or 6-10 membered bicyclic heterocycle, wherein any 5-7 membered monocyclic carbocycle, 6-10 membered bicyclic carbocycle, 5-7 membered monocyclic heterocycle, or 6-10 bicyclic heterocycle of B is optionally substituted with 1, 2, 3, 4 or 5 $Z^2$ groups, wherein the $Z^2$ groups are the same or different;

X is C or N;

$R^1$ is phenyl, 5-6 membered monocycle heteroaryl, 5-6-membered monocyclic heterocycle, 9-10 membered bicyclic heterocycle, or 3-7 membered carbocycle, wherein any phenyl, 5-6 membered monocycle heteroaryl, 5-6-membered monocycle heterocycle, 9-10 membered bicyclic heterocycle, or 3-7 membered carbocycle of $R^1$ optionally substituted with 1, 2, 3, 4 or 5 $Z^3$ groups, wherein the $Z^3$ groups are the same or different;

$R^2$ is $(C_1$-$C_6)$alkyl or 3-7 membered carbocycle, wherein any $(C_1$-$C_6)$alkyl of $R^2$ is optionally substituted with 1, 2, 3, 4 or 5 halo groups, which may be same or different;

$R^3$ is phenyl, 9-10 membered bicycle aryl, 5-7 membered monocycle heterocycle, or 8-10 membered bicyclic heterocycle, wherein any phenyl, 9-10 membered bicyclic aryl, 5-7 membered monocycle heterocycle, or 8-10 membered bicyclic heterocycle of $R^3$ is optionally substituted with 1, 2, 3, 4 or 5 $Z^4$ groups, wherein the $Z^4$ groups are the same or different;

$R^4$ is H or $(C_1$-$C_6)$alkyl optionally substituted with 1, 2, 3, 4 or 5 halo groups, which may be same or different;

each $Z^1$ is independently $(C_1$-$C_6)$alkyl, $(C_2$-$C_6)$alkenyl, $(C_2$-$C_6)$alkynyl, 3-7 membered carbocycle, halo, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —$C(O)R^{n1}$, —$C(O)OR^{n1}$, or —$C(O)NR^{q1}R^{r1}$, wherein any 3-7 membered carbocycle of $Z^1$ is optionally substituted with 1, 2, 3, 4 or 5 halo groups or $(C_1$-$C_6)$alkyl, which may be same or different, and wherein any $(C_1$-$C_6)$alkyl, $(C_2$-$C_6)$alkenyl and $(C_2$-$C_6)$alkynyl of $Z^1$ is optionally substituted with 1, 2, 3, 4 or 5 halo groups, which may be same or different;

each $R^{n1}$ is independently H or $(C_1$-$C_6)$alkyl;

each $R^{p1}$ is independently $(C_1$-$C_6)$alkyl;

each $R^{q1}$ and $R^{r1}$ is independently H or $(C_1$-$C_6)$alkyl;

each $Z^2$ is independently $(C_1$-$C_6)$alkyl, halo, oxo, or —$OR^{n2}$, wherein any 3-7 membered carbocycle of $Z^2$ is optionally substituted with 1, 2, 3, 4 or 5 $(C_1$-$C_6)$alkyl or halo groups, which may be same or different, and wherein any $(C_1$-$C_6)$alkyl of $Z^2$ is optionally substituted with 1, 2, 3, 4 or 5 halo groups, which may be same or different;

each R is independently H, $(C_1$-$C_3)$alkyl, $(C_1$-$C_3)$haloalkyl, or $(C_3$-$C_7)$carbocycle;

each $Z^3$ is independently $(C_1$-$C_6)$alkyl, halo, —CN, —$OR^{n3}$, $NO_2$, or —$C(O)NR^{q3}R^{r3}$, wherein any $(C_1$-$C_6)$alkyl of $Z^3$ is optionally substituted with 1, 2, 3, 4 or 5 halo groups, which may be same or different;

each $R^{n3}$ is independently H, $(C_1$-$C_3)$alkyl, $(C_1$-$C_3)$haloalkyl, or $(C_3$-$C_7)$carbocycle;

each $R^{q3}$ and $R^{r3}$ is independently H or $(C_1$-$C_6)$alkyl;

each $Z^4$ is independently $(C_1$-$C_6)$alkyl, $(C_2$-$C_6)$alkenyl, $(C_2$-$C_6)$alkynyl, $(C_3$-$C_7)$carbocycle, halo, oxo, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r1}$, —$NR^{n4}S(O)_2R^{p4}$, —$NR^{n4}S(O)_2OR^{p4}$, —$NR^{n4}S(O)_2NR^{q4}R^{r4}$, $NO_2$, —$C(O)R^{n4}$, —$C(O)OR^{n4}$, or —$C(O)NR^{q4}R^{r4}$, wherein any $(C_3$-$C_7)$carbocycle, of $Z^1$ is optionally substituted with 1, 2, 3, 4 or 5 halo groups or $(C_1$-$C_6)$alkyl, and wherein any $(C_1$-$C_6)$alkyl, $(C_2$-$C_6)$alkenyl and $(C_1$-$C_6)$alkynyl of $Z^4$ is optionally substituted with 1, 2, 3, 4 or 5 halo groups, which may be same or different;

each $R^{n4}$ is independently H or $(C_1$-$C_5)$alkyl;

each $R^{p4}$ is $(C_1$-$C_6)$alkyl; and each $R^{q4}$ and $R^{r4}$ is independently H or $(C_1$-$C_6)$alkyl;

or a pharmaceutically acceptable salt thereof.

In another aspect, the present disclosure provides a compound of Formula (I):

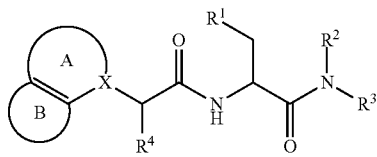

wherein:

ring A, including the two carbon atoms to which it is fused to ring B, is a 5-6 membered monocycle heteroaryl or phenyl, wherein any 5-6 membered heteroaryl or phenyl of A is optionally substituted with 1, 2, or 3 $Z^1$ groups, wherein the $Z^1$ groups are the same or different;

ring B, including the two carbon atoms to which it is fused to ring A, is a 5-7 membered monocyclic carbocycle, 6-10 membered bicyclic carbocycle, 5-7 membered monocycle heterocycle, or 6-10 membered bicyclic heterocycle, wherein any 5-7 membered monocycle carbocycle, 6-10 membered bicyclic carbocycle, 5-7 membered monocyclic heterocycle, or 6-10 bicycle heterocycle of B is optionally substituted with 1, 2, 3, 4 or 5 $Z^2$ groups, wherein the $Z^2$ groups are the same or different;

X is C or N;
or the moiety

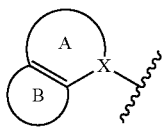

is

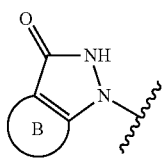

wherein B is as defined above;

$R^1$ is phenyl, 5-6 membered monocycle heteroaryl, 5-6-membered monocycle heterocycle, 9-10 membered bicyclic heterocycle, or 3-7 membered carbocycle, wherein any phenyl, 5-6 membered monocycle heteroaryl, 5-6-membered monocyclic heterocycle, 9-10 membered bicyclic heterocycle, or 3-7 membered carbocycle of $R^1$ is optionally substituted with 1, 2, 3, 4 or 5 $Z^3$ groups, wherein the $Z^3$ groups are the same or different; or $R^1$ is benzothiofuranyl, in which any of the rings are optionally substituted with 1, 2, or 3 $Z^3$ groups;

$R^2$ is $(C_1-C_6)$alkyl or 3-7 membered carbocycle, wherein any $(C_1-C_6)$alkyl of $R^2$ is optionally substituted with 1, 2, 3, 4 or 5 halo groups, which may be same or different;

$R^3$ is phenyl, 9-10 membered bicyclic aryl, 5-7 membered monocycle heterocycle, or 8-10 membered bicyclic heterocycle, wherein any phenyl, 9-10 membered bicycle aryl, 5-7 membered monocycle heterocycle, or 8-10 membered bicyclic heterocycle of $R^3$ is optionally substituted with 1, 2, 3, 4 or 5 $Z^4$ groups, wherein the $Z^4$ groups are the same or different;

$R^4$ is H or $(C_1-C_6)$alkyl optionally substituted with 1, 2, 3, 4 or 5 halo groups, which may be same or different;

each $Z^1$ is independently $(C_1-C_6)$alkyl, $(C_2-C_6)$alkenyl, $(C_2-C_6)$alkynyl, 3-7 membered carbocycle, halo, —CN, —$OR^{n1}$, —$OC(O)R^{p1}$, —$OC(O)NR^{q1}R^{r1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —$C(O)R^{n1}$, —$C(O)OR^{n1}$, or —$C(O)NR^{q1}R^{r1}$, wherein any 3-7 membered carbocycle of $Z^1$ is optionally substituted with 1, 2, 3, 4 or 5 halo groups or $(C_1-C_6)$alkyl, which may be same or different, and wherein any $(C_1-C_6)$alkyl, $(C_2-C_6)$alkenyl and $(C_2-C_6)$alkynyl of $Z^1$ is optionally substituted with 1, 2, 3, 4 or 5 halo groups, which may be same or different;

each $R^{n1}$ is independently H or $(C_1-C_6)$alkyl;
each $R^{p1}$ is independently $(C_1-C_6)$alkyl;
each $R^{q1}$ and $R^{r1}$ is independently H or $(C_1-C_6)$alkyl;
each $Z^2$ is independently $(C_1-C_6)$alkyl, halo, oxo, —$OR^{n2}$, wherein any 3-7 membered carbocycle of $Z^2$ is optionally substituted with 1, 2, 3, 4 or 5 $(C_1-C_6)$alkyl or halo groups, which may be same or different, and wherein any $(C_1-C_6)$alkyl of $Z^2$ is optionally substituted with 1, 2, 3, 4 or 5 halo groups, which may be same or different;

each $R^{n2}$ is independently H, $(C_1-C_3)$alkyl, $(C_1-C_3)$haloalkyl, or $(C_3-C_7)$carbocycle;

each $Z^3$ is independently $(C_1-C_6)$alkyl, halo, —CN, —$R^{n3}$, $NO_2$, or —$C(O)NR^{q3}R^{r3}$, wherein any $(C_1-C_6)$alkyl of $Z^3$ is optionally substituted with 1, 2, 3, 4 or 5 halo groups, which may be same or different;

each $R^{n3}$ is independently H, $(C_1-C_3)$alkyl, $(C_1-C_3)$haloalkyl, or $(C_3-C_7)$carbocycle;

each $R^{q3}$ and $R^{r3}$ is independently H or $(C_1-C_6)$alkyl;
each $Z^4$ is independently $(C_1-C_6)$alkyl, $(C_2-C_6)$alkenyl, $(C_2-C_6)$alkynyl, $(C_3-C_7)$carbocycle, halo, oxo, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, $NO_2$, —$C(O)R^{n4}$, —$C(O)OR^{n4}$, or —$C(O)NR^{q4}R^{r4}$, wherein any $(C_3-C_7)$carbocycle, of $Z^1$ is optionally substituted with 1, 2, 3, 4 or 5 halo groups or $(C_1-C_6)$alkyl, and wherein any $(C_1-C_6)$alkyl, $(C_2-C_6)$alkenyl and $(C_2-C_6)$alkynyl of $Z^4$ is optionally substituted with 1, 2, 3, 4 or 5 halo groups, which may be same or different;

each $R^{n4}$ is independently H or $(C_1-C_6)$alkyl;
each $R^{p4}$ is $(C_1-C_6)$alkyl; and
each $R^{q4}$ and $R^{r4}$ is independently H or $(C_1-C_6)$alkyl; or a pharmaceutically acceptable salt thereof.

One embodiment provides a pharmaceutical composition comprising a compound of formula I or a pharmaceutically acceptable salt thereof, and a pharmaceutically acceptable carrier.

One embodiment provides a pharmaceutical composition comprising a compound of formula I or a pharmaceutically acceptable salt thereof; and an additional therapeutic agent, wherein the additional therapeutic agent is an HIV protease inhibiting, compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor, or combinations thereof.

One embodiment provides a method for treating a Retroviridae viral infection (e.g., an HIV viral infection) in a patient (e.g., a human), comprising administering a compound of formula I, or a pharmaceutically acceptable salt thereof, to the patient.

One embodiment provides a method for treating an HIV infection in a patient (e.g., a human), comprising administering a compound of formula I, or a pharmaceutically acceptable salt thereof to the patient.

One embodiment provides a method for treating an HIV infection in a patient (e.g., a human), comprising administering to the patient in need thereof a therapeutically effective amount of a compound of formula I, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an my nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor, or combinations thereof.

One embodiment provides a compound of formula I, or a pharmaceutically acceptable salt thereof for use in medical therapy (e.g., for use in treating a Retroviridae viral infection (e.g., an HIV viral infection) or the proliferation of the HIV virus or AIDS in a patient (e.g., human)).

One embodiment provides a compound of formula I, or a pharmaceutically acceptable salt thereof, for use in the therapeutic treatment of a Retroviridae viral infection, an HIV virus infection, or AIDS.

One embodiment provides a compound of formula I, or a pharmaceutically acceptable salt thereof for use in the manufacture of a medicament for treating a Retrovfridae viral infection (e.g., an HIV viral infection) or the proliferation of the HIV virus or AIDS in a patient (e.g., a human) One embodiment provides a compound of formula I, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof, for use in a method for treating an HIV infection in a patient (e.g., a human).

One embodiment provides processes and intermediates disclosed herein that are useful for preparing compounds of formula I or salts thereof. Another embodiment provides processes and intermediates disclosed herein that are useful for preparing compounds of any one of formulas I, Ia, and Ib, or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

The present disclosure relates to, inter alia, compounds useful for treating viral infections, in particular an HIV infection, pharmaceutical compositions thereof, processes for making the compounds, and methods of use thereof in treating viral infections, in particular an HIV (human immunodeficiency virus) infection.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Terms

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. A prefix such as "$C_{u\text{-}v}$" or $(C_u\text{-}C_v)$ indicates that the following group has from u to v carbon atoms where u and v are each integers. For example, "$C_{1-6}$alkyl" indicates that the alkyl group has from 1 to 6 carbon atoms.

"Alkyl" is a linear or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms (i.e., ($C_1$-$C_4$)alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)(CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkenyl" is a linear or branched hydrocarbon with at least one carbon-carbon double bond. For example, an alkenyl group can have 2 to 8 carbon atoms $C_2$-$C_8$ alkenyl), or 2 to 6 carbon atoms (i.e., $C_2$-$C_6$ alkenyl) or 2 to 4 carbon atoms (i.e., $C_2$-$C_4$ alkenyl). Examples of suitable alkenyl groups include, but are not limited to, ethylene or vinyl (—CH=CH$_2$), allyl (—CH$_2$CH=CH$_2$) and 5-hexenyl (—CH$_2$CH$_2$CH$_2$CH$_2$CH=CH$_2$).

"Alkynyl" is a linear or branched hydrocarbon with at least one carbon-carbon triple bond. For example, an alkynyl group can have 2 to 8 carbon atoms (i.e., C$_2$-C$_8$ alkyne) or 2 to 6 carbon atoms C$_2$-C$_6$ alkynyl) or 2 to 4 carbon atoms (i.e., C$_2$-C$_4$ alkynyl). Examples of suitable alkynyl groups include, but are not limited to, acetylenyl (—CH≡CH), propargyl (—CH$_2$C≡CH), and the like.

The term "halo" or "halogen" as used herein refers to fluoro (—F), chloro (—Cl), bromo (—Br) and iodo (—I).

The term "haloalkyl" as used herein refers to an alkyl as defined herein, wherein one or more hydrogen atoms of the alkyl are each independently replaced by a halo substituent. For example, (C$_1$-C$_6$)haloalkyl is a (C$_1$-C$_6$)alkyl wherein one or more of the hydrogen atoms of the (C$_1$-C$_6$)alkyl have been replaced by a halo substituent. Examples of haloalkyls include but are not limited to fluoromethyl, fluorochloromethyl, difluoromethyl, difluorochloromethyl, trifluoromethyl, 1,1,1-trifluoroethyl and pentafluoroethyl.

The term "heteroalkyl" as used herein refers to an alkyl in which one or more of the carbon atoms are each independently replaced with a heteroatom selected from the group consisting of O, N, S, and Si. A heteroatom may optionally be oxidized or alkylated. A heteroatom may be placed at any interior position of the heteroalkyl group or at a position at which the group is attached to the remainder of the molecule. Examples include, but are not limited to, —CH$_2$OCH$_3$, —CH$_2$CH$_2$NHCH$_3$, —CH$_2$CH$_2$N(CH$_3$)—CH$_3$, —CH$_2$SCH$_2$CH$_3$, —S(O)CH$_3$, —CH$_2$(CH$_2$S(O)$_2$CH$_3$, —CHCHOCH$_3$, —Si(CH$_3$)$_3$, —CH$_2$CHNOCH$_3$, —CHCHN(CH$_3$)CH$_3$, —CH$_2$NHOCH$_3$ and —CH$_2$OS(CH$_3$)$_3$.

The term "aryl" as used herein refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Unless otherwise specified, an aryl group has from 6 to about 20 carbon atoms, for example from 6 to 20 carbon atoms, for example from 6 to 14 carbon atoms, for example from 6 to 10 carbon atoms, for example from about 6 to 10 carbon atoms.

The term "heteroaryl" as used herein refers to an aryl group in which one or more of the carbon atoms (and any associated hydrogen atoms) are each independently replaced with the same or different heteroatom, as defined above. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Unless otherwise specified, a heteroaryl group has from 5 to about 20 annular atoms, for example from 5 to 20 annular atoms, for example from 5 to 14 annular atoms, for example from 5 to 10 annular atoms. Thus, "heteroaryl" includes single aromatic rings of from about 1 to 6 annular carbon atoms and about 14 annular heteroatoms selected from the group consisting of oxygen, nitrogen and sulfur. The sulfur and nitrogen atoms may also be present in an oxidized form provided the ring is aromatic.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Thus, the term includes single saturated or partially unsaturated rings (e.g., 3, 4, 5, 6 or 7-membered rings) from about 1 to 6 annular carbon atoms and from about 1 to 3 annular heteroatoms selected from the group consisting of oxygen, nitrogen and sulfur in the ring. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

The term "carbocycle" or "carbocyclyl" refers to a single saturated or partially unsaturated all carbon ring having 3 to 7 annular carbon atoms (i.e., (C$_3$-C$_7$)carbocycle). The term "carbocycle" or "carbocyclyl" also includes multiple condensed, saturated and partially unsaturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of the multiple condensed ring system can be connected to each other via fused, spiro and bridged bonds when allowed by valency requirements Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH ~7). Thus, it is understood that "about x" includes and describes "x" per se.

As used herein, "treatment" or "treating" is an approach for obtaining beneficial or desired results. For purposes of this invention, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming an individual's HIV+ status and assessing the individual's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in individuals with functioning immune systems but does occur in AIDS patients). Development may also refer to disease progression that may be initially undetectable and includes occurrence, recurrence and onset.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term. "effective amount" refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The nomenclature used herein to name the subject compounds is illustrated in the Examples and elsewhere herein. This nomenclature has generally been derived using the commercially-available naming program used in Chem-Draw Ultra, Version 12.0 (Perkin Elmer, Waltham Mass.). Compounds The present disclosure provides a compound of Formula (I):

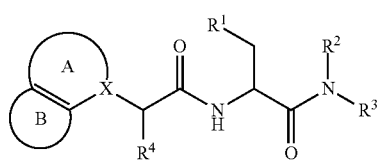

I wherein:
ring A, including the two carbon atoms to which it is fused to ring B, is a 5-6 membered monocyclic heteroaryl or phenyl, wherein any 5-6 membered heteroaryl or phenyl of A is optionally substituted with 1, 2, or 3 $Z^1$ groups, wherein the $Z^1$ groups are the same or different;

ring B, including the two carbon atoms to which it is fused to ring A, is a 5-7 membered monocyclic carbocycle, 6-10 membered bicyclic carbocycle, 5-7 membered monocyclic heterocycle, or 6-10 membered bicyclic heterocycle, wherein any 5-7 membered monocyclic carbocycle, 6-10 membered bicyclic carbocycle, 5-7 membered monocyclic heterocycle, or 6-10 bicyclic heterocycle of B is optionally substituted with 1, 2, 3, 4 or 5 $Z^2$ groups, wherein the $Z^2$ groups are the same or different;

X is C N;

$R^1$ is phenyl, 5-6 membered monocycle heteroaryl, 5-6-membered monocycle heterocycle, 9-10 membered bicyclic heterocycle, or 3-7 membered carbocycle, wherein any phenyl, 5-6 membered monocycle heteroaryl, 5-6-membered monocycle heterocycle, 9-10 membered bicyclic heterocycle, or 3-7 membered carbocycle of $R^1$ is optionally substituted with 1, 2, 3, 4 or 5 $Z^3$ groups, wherein the $Z^3$ groups are the same or different;

$R^2$ is $(C_1-C_6)$alkyl or 3-7 membered carbocycle, wherein any $(C_1-C_6)$alkyl of $R^2$ is optionally substituted with 1, 2, 3, 4 or 5 halo groups, which may be same or different;

$R^3$ is phenyl, 9-10 membered bicyclic aryl, 5-7 membered monocycle heterocycle, or 8-10 membered bicycle heterocycle, wherein any phenyl, 9-10 membered bicyclic aryl, 5-7 membered monocycle heterocycle, or 8-10 membered bicycle heterocycle of $R^3$ is optionally substituted with 1, 2, 3, 4 or 5 $Z^4$ groups, wherein the $Z^4$ groups are the same or different;

$R^4$ is H or $(C_1-C_6)$alkyl optionally substituted with 1, 2, 3, 4 or 5 halo groups, which may be same or different;

each Z is independently $(C_1-C_6)$alkyl, $(C_2-C_6)$alkenyl, $(C_2-C_6)$alkynyl, 3-7 membered carbocycle, halo, —CN, —$OR^{n1}$, —OC(O)$NR^{q1}R^{r1}$, —$SR^{n1}$, —S(O)$R^{p1}$, —S(O)$_2$OH, —S(O)$_2R^{p1}$, —S(O)$_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —C(O)$R^{n1}$, —C(O)$OR^{n1}$, or —C(O)$NR^{q1}R^{r1}$, wherein any 3-7 membered carbocycle of $Z^1$ is optionally substituted with 1, 2, 3, 4 or 5 halo groups or $(C_1-C_6)$alkyl, which may be same or different, and wherein any $(C_1-C_6)$alkyl, $(C_2-C_6)$alkenyl and $(C_2-C_6)$alkynyl of $Z^1$ is optionally substituted with 1, 2, 3, 4 or 5 halo groups, which may be same or different;

each $R^{n1}$ is independently H or $(C_1-C_6)$alkyl;
each $R^{p1}$ is independently $(C_1-C_6)$alkyl;
each $R^{q1}$ and $R^{r1}$ is independently H or $(C_1-C_6)$alkyl;
each $Z^2$ is independently $(C_1-C_6)$alkyl, halo, oxo, or —$OR^{n2}$, wherein any 3-7 membered carbocycle of $Z^2$ is optionally substituted with 1, 2, 3, 4 or 5 $(C_1-C_6)$alkyl or halo groups, which may be same or different, and wherein any $(C_1-C_6)$alkyl of $Z^2$ is optionally substituted with 1, 2, 3, 4 or 5 halo groups, which may be same or different;

each $R^{n2}$ is independently H, $(C_1-C_3)$alkyl, $(C_1-C_3)$haloalkyl or $(C_3-C_7)$carbocycle;

each $Z^3$ is independently $(C_1-C_6)$alkyl, halo, —CN, —$OR^{n3}$, $NO_2$, or —C(O)$NR^{q3}R^{r3}$, wherein any $(C_1-C_6)$alkyl of $Z^3$ is optionally substituted with 1, 2, 3, 4 or 5 halo groups, which may be same or different;

each $R^{n3}$ is independently H, $(C_1-C_3)$alkyl, $(C_1-C_3)$haloalkyl, or $(C_3-C_7)$carbocycle;

each $R^{q3}$ and $R^{r3}$ is independently H or $(C_1-C_6)$alkyl;
each $Z^4$ is independently $(C_1-C_6)$alkyl $(C_2-C_6)$alkenyl, $(C_2-C_6)$alkynyl, $(C_3-C_7)$carbocycle, halo, oxo, —CN, —$OR^{n4}$, —OC(O)$R^{p4}$, —OC(O)$NR^{q4}R^{r4}$, —$SR^{n4}$, —S(O)

$R^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{r4}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$, or —C(O)NR$^{q4}$R$^{r4}$, wherein any (C$_3$-C$_7$)carbocycle, of Z$^1$ is optionally substituted with 1, 2, 3, 4 or 5 halo groups or (C$_1$-C$_5$)alkyl, and wherein any (C$_1$-C$_6$)alkyl, (C$_2$-C$_6$)alkenyl and (C$_2$-C$_5$)alkynyl of Z$^4$ is optionally substituted with 1, 2, 3, 4 or 5 halo groups, which may be same or different;

each R$^{n4}$ is independently H or (C$_1$-C$_6$)alkyl;

each R$^{p4}$ is (C$_1$-C$_6$)alkyl; and each R$^{q4}$ and R$^{r4}$ is independently H or (C$_1$-C$_6$)alkyl;

or a pharmaceutically acceptable salt thereof.

The present disclosure also provides a compound of Formula (I):

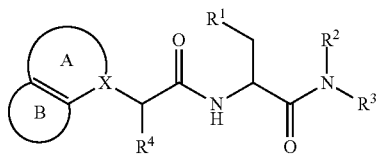

wherein:

ring A, including the two carbon atoms to which it is fused to ring B, is a 5-6 membered monocyclic heteroaryl or phenyl, wherein any 5-6 membered heteroaryl or phenyl of A is optionally substituted with 1, 2, or 3 Z$^1$ groups, wherein the Z$^1$ groups are the same or different;

ring B, including the two carbon atoms to which it is fused to ring A, is a 5-7 membered monocycle carbocycle, 6-10 membered bicyclic carbocycle, 5-7 membered monocyclic heterocycle, or 6-10 membered bicycle heterocycle, wherein any 5-7 membered monocyclic carbocycle, 6-10 membered bicyclic carbocycle, 5-7 membered monocyclic heterocycle, or 6-10 bicyclic heterocycle of B is optionally substituted with 1, 2, 3, 4 or 5 Z$^2$ groups, wherein the Z$^2$ groups are the same or different;

X is C or N;

or the moiety

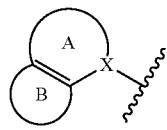

is

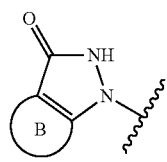

wherein B is as defined above;

R$^1$ is phenyl, 5-6 membered monocyclic heteroaryl, 5-6-membered monocycle heterocycle, 9-10 membered bicyclic heterocycle, or 3-7 membered carbocycle, wherein any phenyl, 5-6 membered monocycle heteroaryl, 5-6-membered monocycle heterocycle, 9-10 membered bicycle heterocycle, or 3-7 membered carbocycle of R$^1$ is optionally substituted with 1, 2, 3, 4 or 5 Z$^3$ groups, wherein the Z$^3$ groups are the same or different; or R$^1$ is benzothiofuranyl, in which any of the rings are optionally substituted with 1, 2, or 3 Z$^3$ groups;

R$^2$ is (C$_1$-C$_6$)alkyl or 3-7 membered carbocycle, wherein any (C$_1$-C$_6$)alkyl of R$^2$ is optionally substituted with 1, 2, 3, 4 or 5 halo groups, which may be same or different;

R$^3$ is phenyl, 9-10 membered bicyclic aryl, 5-7 membered monocycle heterocycle, or 8-10 membered bicyclic heterocycle, wherein any phenyl, 9-10 membered bicyclic aryl, 5-7 membered monocycle heterocycle, or 8-10 membered bicyclic heterocycle of R$^3$ is optionally substituted with 1, 2, 3, 4 or 5 Z$^4$ groups, wherein the Z$^4$ groups are the same or different;

R$^4$ is H or (C$_1$-C$_6$)alkyl optionally substituted with 1, 2, 3, 4 or 5 halo groups, which may be same or different;

each Z$^1$ is independently (C$_1$-C$_6$)alkyl, (C$_2$-C$_6$)alkenyl, (C$_2$-C$_6$)alkynyl 3-7 membered carbocycle, halo, —CN, —OR$^{n1}$, —OC(O)R$^{p1}$, —OC(O)NR$^{q1}$R$^{r1}$, —SR$^{n1}$, —S(O)R$^{p1}$, —S(O)$_2$OH, —S(O)$_2$R$^{p1}$, —S(O)$_2$NR$^{q1}$R$^{r1}$, —NR$^{q1}$R$^{r1}$, —NR$^{n1}$COR$^{p1}$, —NR$^{n1}$CO$_2$R$^{p1}$, —NR$^{n1}$CONR$^{q1}$R$^{r1}$, —NR$^{n1}$S(O)$_2$R$^{p1}$, —NR$^{n1}$S(O)$_2$OR$^{p1}$, —NR$^{n1}$S(O)$_2$NR$^{q1}$R$^{r1}$, NO$_2$, —C(O)R$^{n1}$, —C(O)OR$^{n1}$, or —C(O)NR$^{q1}$R$^{r1}$, wherein any 3-7 membered carbocycle of Z$^1$ is optionally substituted with 1, 2, 3, 4 or 5 halo groups or (C$_1$-C$_6$)alkyl, which may be same or different, and wherein any (C$_1$-C$_6$)alkyl, (C$_2$-C$_6$)alkenyl and (C$_2$-C$_6$)alkynyl of Z$^1$ is optionally substituted with 1, 2, 3, 4 or 5 halo groups, which may be same or different;

each R$^{n1}$ is independently H or (C$_1$-C$_6$)alkyl;

each R$^{p1}$ is independently (C$_1$-C$_6$)alkyl;

each R$^{q1}$ and R$^{r1}$ is independently H or (C$_1$-C$_5$)alkyl;

each Z$^2$ is independently (C$_1$-C$_6$)alkyl, halo, oxo, or —OR$^{n2}$, wherein any 3-7 membered carbocycle of Z$^2$ is optionally substituted with 1, 2, 3, 4 or 5 (C$_1$-C$_6$)alkyl or halo groups, which may be same or different, and wherein any (C$_1$-C$_6$)alkyl of Z$^2$ is optionally substituted with 1, 2, 3, 4 or 5 halo groups, which may be same or different;

each R$^{n2}$ is independently H, (C$_1$-C$_3$)alkyl, (C$_1$-C$_3$)haloalkyl, or (C$_3$-C$_7$)carbocycle;

each Z$^3$ is independently (C$_1$-C$_6$)alkyl, halo, —CN, —OR$^{n3}$, NO$_2$, or —C(O)NR$^{q3}$R$^{r3}$, wherein any (C$_1$-C$_6$) alkyl of Z$^3$ is optionally substituted with 1, 2, 3, 4 or 5 halo groups, which may be same or different;

each R$^{n3}$ is independently H, (C$_1$-C$_3$)alkyl, (C$_1$-C$_3$)haloalkyl, or (C$_3$-C$_7$)carbocycle;

each R$^{q3}$ and R$^{r3}$ is independently H or (C$_1$-C$_6$)alkyl;

each Z$^4$ is independently (C$_1$-C$_6$)alkyl, (C$_2$-C$_6$)alkenyl, (C$_2$-C$_6$)alkynyl, (C$_3$-C$_7$)carbocycle, halo, oxo, —CN, —OR$^{n4}$, —OC(O)R$^{p4}$, —OC(O)NR$^{q4}$R$^{r4}$, —SR$^{n4}$, —S(O)R$^{p4}$, —S(O)$_2$OH, —S(O)$_2$R$^{p4}$, —S(O)$_2$NR$^{q4}$R$^{r4}$, —NR$^{q4}$R$^{r4}$, —NR$^{n4}$COR$^{p4}$, —NR$^{n4}$CO$_2$R$^{p4}$, —NR$^{n4}$CONR$^{q4}$R$^{rr}$, —NR$^{n4}$S(O)$_2$R$^{p4}$, —NR$^{n4}$S(O)$_2$OR$^{p4}$, —NR$^{n4}$S(O)$_2$NR$^{q4}$R$^{r4}$, NO$_2$, —C(O)R$^{n4}$, —C(O)OR$^{n4}$, or —C(O)NR$^{q4}$R$^{r4}$, wherein any (C$_3$-C$_7$)carbocycle, of Z$^1$ is optionally substituted with 1, 2, 3, 4 or 5 halo groups or (C$_1$-C$_6$)alkyl, and wherein any (C$_1$-C$_6$)alkyl, (C$_2$-C$_6$)alkenyl and (C$_2$-C$_6$)alkynyl of Z$^4$ is optionally substituted with 1, 2, 3, 4 or 5 halo groups, which may be same or different;

each R$^{n4}$ is independently H or (C$_1$-C$_6$)alkyl;

each R$^{p4}$ is (C$_1$-C$_6$)alkyl; and each R$^{q4}$ and R$^{r4}$ independently H or (C$_1$-C$_6$)alkyl; or a pharmaceutically acceptable salt thereof.

The present disclosure also provides a compound of Formula (Ia)

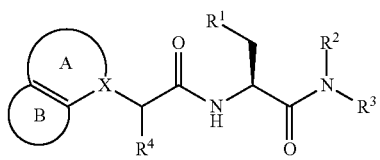

(Ia)

wherein:

ring A, including the two carbon atoms to which it is fused to ring B, is a 5-6 membered monocycle heteroaryl or phenyl, wherein any 5-6 membered heteroaryl or phenyl of A is optionally substituted with 1, 2, or 3 $Z^1$ groups, wherein the $Z^1$ groups are the same or different;

ring B, including the two carbon atoms to which it is fused to ring A, is a 5-7 membered monocycle carbocycle, 6-10 membered bicyclic carbocycle, 5-7 membered monocycle heterocycle, or 6-10 membered bicyclic heterocycle, wherein any 5-7 membered monocycle carbocycle, 6-10 membered bicyclic-carbocycle, 5-7 membered monocycle heterocycle, or 6-10 bicyclic heterocycle of B is optionally substituted with 1, 2, 3, 4 or 5 $Z^2$ groups, wherein the $Z^2$ groups are the same or different;

X is C or N;

$R^1$ is phenyl, 5-6 membered monocycle heteroaryl, 5-6-membered monocycle heterocycle, 9-10 membered bicyclic heterocycle, or 3-7 membered carbocycle, wherein any phenyl, 5-6 membered monocycle heteroaryl, 5-6-membered monocycle heterocycle, 9-10 membered bicycle heterocycle, or 3-7 membered carbocycle of $R^1$ is optionally substituted with 1, 2, 3, 4 or 5 $Z^3$ groups, wherein the $Z^3$ groups are the same or different;

$R^2$ is $(C_1\text{-}C_6)$alkyl or 3-7 membered carbocycle, wherein any $(C_1\text{-}C_6)$alkyl of $R^2$ is optionally substituted with 1, 2, 3, 4 or 5 halo groups, which may be same or different;

$R^3$ is phenyl, 9-10 membered bicyclic aryl, 5-7 membered monocycle heterocycle, or 8-10 membered bicycle heterocycle, wherein any phenyl, 9-10 membered bicyclic aryl, 5-7 membered monocycle heterocycle, or 8-10 membered bicyclic heterocycle of $R^3$ is optionally substituted with 1, 2, 3, 4 or 5 $Z^4$ groups, wherein the $Z^4$ groups are the same or different;

$R^4$ is H or $(C_1\text{-}C_6)$alkyl optionally substituted with 1, 2, 3, 4 or 5 halo groups, which may be same or different;

each $Z^1$ is independently $(C_1\text{-}C_6)$alkyl, $(C_2\text{-}C_6)$alkenyl, $(C_2\text{-}C_6)$alkynyl, 3-7 membered carbocycle, halo, —CN, —$OR^{n1}$, —$OC(O)R^{p1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —$C(O)R^{n1}$, —$C(O)OR^{n1}$, or —$C(O)NR^{q1}R^{r1}$, wherein any 3-7 membered carbocycle of $Z^1$ is optionally substituted with 1, 2, 3, 4 or 5 halo groups or $(C_1\text{-}C_6)$alkyl, which may be same or different, and wherein any $(C_1\text{-}C_6)$alkyl, $(C_2\text{-}C_6)$alkenyl and $(C_2\text{-}C_6)$alkynyl of $Z^1$ is optionally substituted with 1, 2, 3, 4 or 5 halo groups, which may be same or different;

each $R^{n1}$ is independently H or $(C_1\text{-}C_6)$alkyl;
each $R^{p1}$ is independently $(C_1\text{-}C_6)$alkyl;
each $R^{q1}$ and $R^{r1}$ is independently H or $(C_1\text{-}C_6)$alkyl;
each $Z^2$ is independently $(C_1\text{-}C_6)$alkyl, halo, oxo, or —$OR^{n2}$, wherein any 3-7 membered carbocycle of $Z^2$ is optionally substituted with 1, 2, 3, 4 or 5 $(C_1\text{-}C_6)$alkyl or halo groups, which may be same or different, and wherein any $(C_1\text{-}C_6)$alkyl of $Z^2$ is optionally substituted with 1, 2, 3, 4 or 5 halo groups, which may be same or different;

each $R^{n2}$ is independently H, $(C_1\text{-}C_3)$alkyl, $(C_1\text{-}C_3)$haloalkyl, or $(C_3\text{-}C_7)$carbocycle;

each $Z^3$ is independently $(C_1\text{-}C_6)$alkyl, halo, —CN, —$OR^{n3}$, $NO_2$, or —$C(O)NR^{q3}R^{r3}$, wherein any $(C_1\text{-}C_6)$alkyl of $Z^3$ is optionally substituted with 1, 2, 3, 4 or 5 halo groups, which may be same or different;

each $R^{n3}$ is independently H, $(C_1\text{-}C_3)$alkyl, $(C_1\text{-}C_3)$haloalkyl, or $(C_3\text{-}C_7)$carbocycle;

each $R^{q3}$ and $R^{r3}$ is independently H or $(C_1\text{-}C_6)$alkyl;

each $Z^4$ is independently $(C_1\text{-}C_6)$alkyl, $(C_2\text{-}C_6)$alkenyl, $(C_2\text{-}C_6)$alkynyl, $(C_3\text{-}C_7)$carbocycle, halo, oxo, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{r4}S(O)_2NR^{q4}R^{r4}$, $NO_2$, —$C(O)R^{n4}$, —$C(O)OR^{n4}$, or —$C(O)NR^{q4}R^{r4}$, wherein any $(C_3\text{-}C_7)$carbocycle, of $Z^1$ is optionally substituted with 1, 2, 3, 4 or 5 halo groups or $(C_1\text{-}C_6)$alkyl, and wherein any $(C_1\text{-}C_6)$alkyl, $(C_2\text{-}C_6)$alkenyl and $(C_2\text{-}C_6)$alkynyl of $Z^4$ is optionally substituted with 1, 2, 3, 4 or 5 halo groups, which may be same or different;

each $R^{n4}$ is independently H or $(C_1\text{-}C_6)$alkyl;
each $R^{p4}$ is $(C_1\text{-}C_6)$alkyl; and
each $R^{q4}$ and $R^{r4}$ independently H or $(C_1\text{-}C_6)$alkyl;

or a pharmaceutically acceptable salt thereof.

Specific values listed below are values for compounds of formula I as well as all related formulas (e.g., formulas Ia and Ib). It is to be understood that two or more values may combined. Thus, it is to be understood that any variable for compounds of formula I may be combined with any other variable for compounds of formula I the same as if each and every combination of variables were specifically and individually listed. For example, it is understood that any specific value of $R^1$ detailed herein for compounds of formula 1 may be combined with any other specific value for one or more of the variables A, B, X, $R^2$, $R^3$, or $R^4$, the same as if each and every combination were specifically and individually listed.

In one variation of Formula (I), the carbon bearing —$CH_2R^1$ is in the (S)-configuration. It is understood that compositions detailed herein may comprise a compound of Formula (I) in a racemic or non-racemic mixture of stereoisomers or may comprise a compound of Formula (I) as a substantially pure isomer (e.g., as the (S)-isomer at one or more stereocenters).

In certain embodiments of Formula (I) and (Ia), the 5-6 membered heteroaryl of A comprises 1-2 annular nitrogen atoms and 3-4 annular carbon atoms. In certain instances, ring A is a 5-6 membered monocyclic heteroaryl, wherein the 5-6 membered heteroaryl of A comprises 1-2 nitrogen atoms and 3-4 carbon atoms in the ring, and wherein any 5-6 membered heteroaryl of A is optionally substituted with one or two $Z^1$ groups. In certain instances, ring A, including the two carbon atoms to which it is fused to ring B, is a 5-6 membered monocycle heteroaryl, wherein the 5-6 membered heteroaryl of A comprises 1-2 annular nitrogen atoms and 3-4 annular carbon atoms in the ring, and wherein any 5-6 membered heteroaryl of A is optionally substituted with one or two $Z^1$ groups; and X is N.

In certain embodiments of Formula (I) and (Ia), the 5-6 membered heteroaryl of A comprises 1-2 annular nitrogen atoms and 3-4 annular carbon atoms in the ring. In certain instances, the 5-6 membered heteroaryl of A comprises 2 annular nitrogen atoms and 3 annular carbon atoms.

In certain embodiments of Formula (I) and (Ia), ring A is a 5-6 membered monocyclic heteroaryl or phenyl, wherein the 5-6 membered heteroaryl of A comprises 1-2 annular nitrogen atoms and 3-4 annular carbon atoms in the ring, and wherein any 5-6 membered heteroaryl or phenyl of A is optionally substituted with 1, 2, or 3 $Z^1$ groups. In certain embodiments, ring A is a 5-6 membered monocycle heteroaryl or phenyl, wherein the 5-6 membered heteroaryl of A comprises 1-2 annular nitrogen atoms and 3-4 annular carbon atoms in the ring, and wherein any 5-6 membered heteroaryl or phenyl of A is optionally substituted with 1 or 2 $Z^1$ groups.

In certain embodiments of Formula (I) and (Ia), ring A is a 5-6 membered monocycle heteroaryl, wherein the 5-6 membered heteroaryl of A comprises 1-2 annular nitrogen atoms and 3-4 annular carbon atoms in the ring, and wherein any 5-6 membered heteroaryl of A is optionally substituted with 1, 2, or 3 $Z^1$ groups. In one such variation, X is N. In certain embodiments, ring A is a 5-6 membered monocyclic heteroaryl, wherein the 5-6 membered heteroaryl of A comprises 1-2 annular nitrogen atoms and 34 annular carbon atoms in the ring, and wherein any 5-6 membered heteroaryl of A is optionally substituted with 1 or 2 $Z^1$ groups. In one such variation, X is N.

In certain embodiments of Formula (I) and (Ia), the moiety

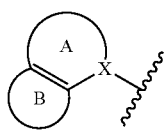

is

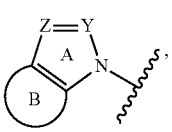

wherein Y is $CZ^{1a}$ or N; Z is $CZ^{1a}$ or N; and each $Z^{1a}$ is independently H or $Z^1$. In certain embodiments, Y is N. In certain embodiments, Y is $CZ^{1a}$, wherein $Z^{1a}$ is H. In certain embodiments, Y is $CZ^{1a}$, wherein $Z^{1a}$ is $Z^1$. In certain embodiments, Y is $CZ^{1a}$, wherein $Z^{1a}$ is $Z^1$ and $Z^1$ is an optionally substituted $(C_1-C_6)$alkyl (e.g., —$CH_3$ and —$CF_3$), halo, or —$NR^{q1}R^{r1}$ (e.g., —$NH_2$). In certain embodiments, Z is N. In certain embodiments, Z is $CZ^{1a}$, wherein $Z^{1a}$ is H. In certain embodiments, Z is $CZ^{1a}$, wherein $Z^{1a}$ is $Z^1$. In certain embodiments, Z is $CZ^{1a}$, wherein $Z^{1a}$ is $Z^1$ and $Z^1$ is an optionally substituted $(C_1-C_6)$alkyl (e.g., —$CH_3$ and —$CF_3$), halo, or —$NR^{q1}R^{r1}$ (e.g., —$NH_2$). It is understood that any Y moiety may be combined with any Z moiety the same as if each and every combination were specifically and individually listed. For example, it is understood that in one embodiment, Y is N and Z is $CZ^{1a}$ where $Z^{1a}$ is $Z^1$ (e.g., an optionally substituted $(C_1-C_6)$alkyl). B in these embodiments may be any B moiety as detailed herein.

In certain embodiments of Formula (I) and (Ia), the moiety

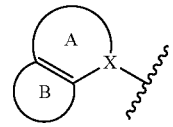

is

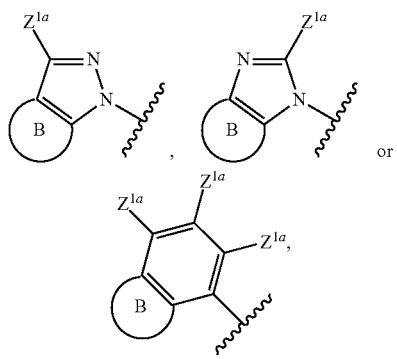

wherein each $Z^{1a}$ is independently or $Z^1$. In certain embodiments, each $Z^{1a}$ is H. In certain embodiments, $Z^{1g}$ is $Z^1$. In certain embodiments, $Z^{1a}$ is $Z^1$ and $Z^1$ is an optionally substituted $(C_1-C_6)$alkyl (e.g., —$CH_3$ and —$CF_3$), halo, or —$NR^{q1}R^{r1}$ (e.g., —$NH_2$). B in these embodiments may be any B moiety as detailed herein.

In certain embodiments of Formula (I) and (Ia), the moiety

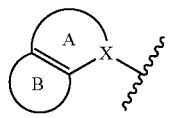

is

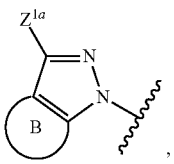

wherein $Z^{1a}$ is independently H or $Z^1$. In certain embodiments, $Z^{1a}$ is H. In certain embodiments, $Z^{1a}$ is $Z^1$. In certain embodiments, $Z^{1a}$ is $Z^1$ and $Z^1$ is an optionally substituted $(C_1-C_6)$alkyl (e.g., —$CH_3$ and —$CF_3$), halo, or —$NR^{q1}R^{r1}$ (e.g., —$NH_2$). B in these embodiments may be any B moiety as detailed herein.

In certain embodiments of Formula (I) and (Ia), the moiety

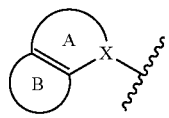

is

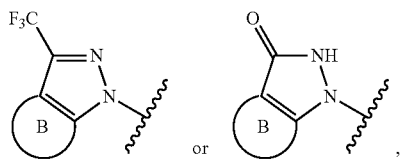

B in these embodiments may be any B moiety as detailed herein.

In certain embodiments of Formula (I) and (Ia), the moiety

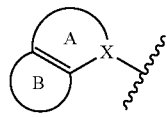

is

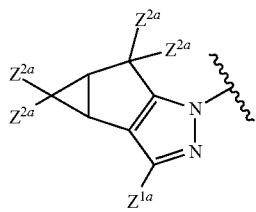

wherein $Z^{1a}$ is independently H or $Z^1$; and each $Z^{2a}$ is independently H or $Z^2$. In certain embodiments, $Z^{1a}$ is H and each $Z^{2a}$ is H. In certain embodiments, $Z^{1a}$ is $Z^1$ and $Z^1$ is an optionally substituted $(C_1$-$C_6)$alkyl (e.g., —$CH_3$ and —$CF_3$), halo, or —$NR^{q1}R^{r1}$ (e.g., —$NH_2$). In certain embodiments, $Z^{1a}$ is —$CF_3$. In certain embodiments, at least one $Z^{2a}$ is an optionally substituted $(C_1$-$C_6)$alkyl (e.g., —$CH_3$ and —$CF_3$), halo, or oxo. In certain embodiments, at least one $Z^{2a}$ is halo (e.g., fluoro). In certain embodiments, two $Z^{2a}$ are halo (e.g., fluoro) and two $Z^{2a}$ are hydrogen.

In certain embodiments of Formula (I) and (Ia), the moiety

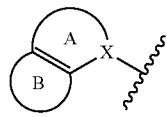

is

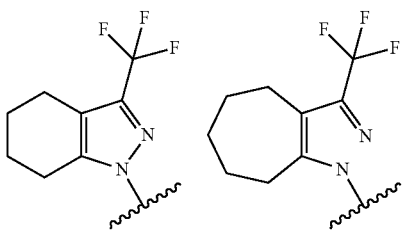

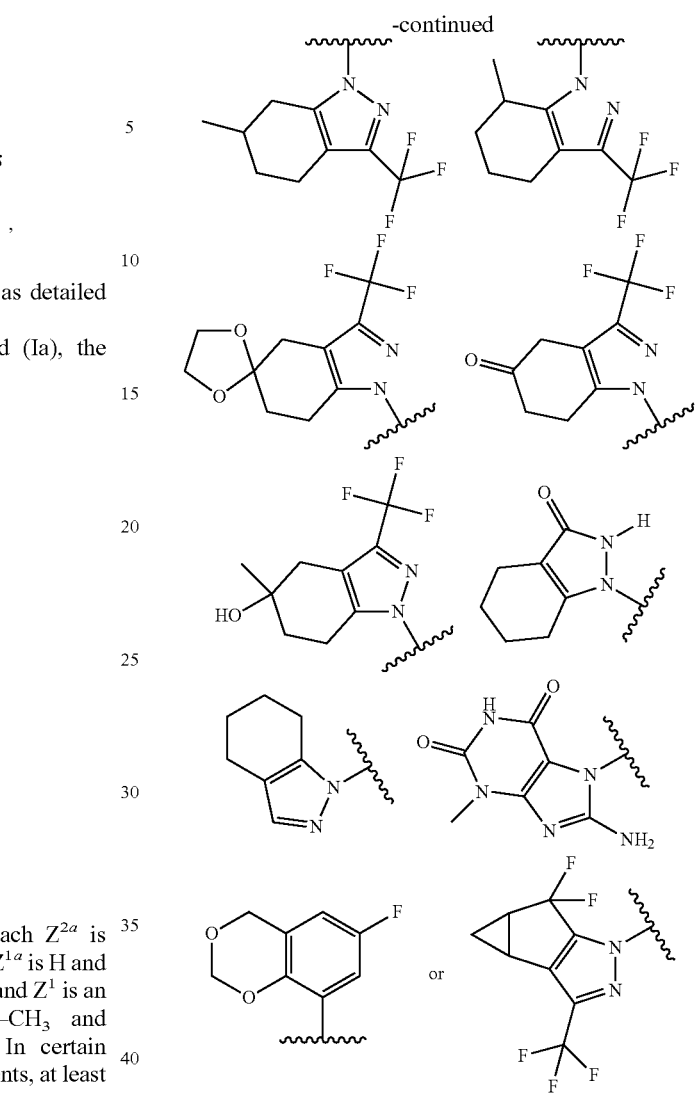

In certain embodiments of Formula (I) and (Ia), $R^4$ is H.

In certain embodiments, a compound of Formula (I) is a compound of Formula (Ib):

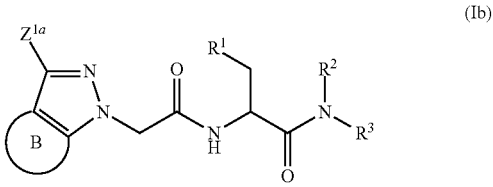

(Ib)

wherein $Z^{1a}$ is H or $Z^1$.

In one aspect, the compounds contain 1, 2, 3, 4 or 5 $Z^1$ moiety. In one aspect, the compounds contain 1 or 2 $Z^1$ moiety. In certain embodiments of Formula (I), (Ia), and (Ib), $Z^1$ is independently $(C_1$-$C_6)$alkyl, halo, —OH, or —$NR^{q1}R^{r1}$, wherein any $(C_1$-$C_6)$alkyl of $Z^1$ is optionally substituted with 1, 2, 3, 4 or 5 halo groups. In certain embodiments, $Z^1$ is independently $(C_1$-$C_6)$alkyl, halo, —OH, or —$NR^{q1}R^{r1}$, wherein any $(C_1$-$C_6)$alkyl of $Z^1$ is optionally substituted with 1, 2, or 3 halo groups. In certain embodiments, $Z^1$ is independently an optionally substituted $(C_1-C_6)$alkyl (e.g., —CH$_3$ and —CF$_3$), halo, or —NR$^{q1}$R$^{r1}$ (e.g., —NH$_3$).

In certain embodiments of Formula (I), (Ia), and (Ib), $Z^1$ is independently —CF$_3$, halo, —OH, or —NH$_2$.

In certain embodiments of Formula (I), (Ia), and (Ib), $Z^1$ is H, —CF$_3$, or OH. In certain instances, $Z^1$ is —CF$_3$.

In certain embodiments of Formula (I), (Ia), and (Ib), ring B is a 5-7 membered monocycle carbocycle, or 6-10 membered bicyclic carbocycle, wherein any 5-7 membered monocyclic carbocycle or 6-10 membered bicycle carbocycle of B is optionally substituted with 1, 2, 3, 4 or 5 $Z^2$ groups. In certain embodiments, ring B is a 5-7 membered monocycle carbocycle, or 6-10 membered bicycle carbocycle, wherein any 5-7 membered monocycle carbocycle or 6-10 membered bicyclic carbocycle of B is optionally substituted with 1, 2, or 3 $Z^2$ groups. In certain embodiments, ring B is a 5-7 membered monocycle carbocycle, or 6-10 membered bicyclic carbocycle, wherein any 5-7 membered monocycle, carbocycle or 6-10 membered bicyclic carbocycle of B is optionally substituted with 1 or 2 $Z^2$ groups.

In certain embodiments of Formula (I), (Ia), and (Ib), ring B is a 6-7 membered monocycle carbocycle, or 6 membered bicyclic carbocycle, wherein any 6-7 membered monocyclic carbocycle or 6 membered bicyclic carbocycle of B is optionally substituted with 1, 2, 3, 4 or 5 $Z^2$ groups. In certain embodiments, ring B is a 6-7 membered monocycle carbocycle, or 6 membered bicyclic carbocycle, wherein any 6-7 membered monocycle carbocycle or 6 membered bicyclic carbocycle of B is optionally substituted with 1, 2, or 3 groups. In certain embodiments, ring B is a 6-7 membered monocycle carbocycle, or 6 membered bicyclic carbocycle, wherein any 6-7 membered monocycle carbocycle or 6 membered bicycle carbocycle of B is optionally substituted with 1 or 2 $Z^2$ groups.

In certain embodiments of Formula (I), (Ia), and (Ib), ring B is a 6-10 membered bicycle carbocycle, or 6-10 membered bicyclic heterocycle, wherein any 6-10 membered bicycle carbocycle or 6-10 bicycle heterocycle of B is optionally substituted with 1, 2, 3, 4 or 5 $Z^2$ groups. In certain embodiments, ring B is a 6-10 membered bicycle carbocycle, or 6-10 membered bicyclic heterocycle, wherein any 6-10 membered bicycle carbocycle or 6-10 bicyclic heterocycle of B is optionally substituted with 1, 2, or 3 $Z^2$ groups. In certain embodiments, ring B is a 6-10 membered bicyclic carbocycle, or 6-10 membered bicyclic heterocycle, wherein any 6-10 membered bicycle carbocycle or 6-10 bicyclic heterocycle of B is optionally substituted with 1 or 2 $Z^2$ groups.

In certain embodiments of Formula (I), (Ia), and (Ib), ring B is a 6-10 membered bicyclic carbocycle, wherein any 6-10 membered bicycle carbocycle of B is optionally substituted with 1, 2, 3, 4 or 5 $Z^2$ groups. In certain embodiments, ring B is a 6-10 membered bicycle carbocycle, wherein any 6-10 membered bicyclic carbocycle of B is optionally substituted with 1, 2, or 3 $Z^2$ groups. In certain embodiments, ring B is a 6-10 membered bicyclic carbocycle, wherein any 6-10 membered bicyclic carbocycle of B is optionally substituted with 1 or 2 $Z^2$ groups.

In certain embodiments of Formula (I), (Ia), and (Ib), ring B is a 6-7 membered bicycle carbocycle, wherein any 6-7 membered bicycle carbocycle is optionally substituted with 1, 2, 3, 4 or 5 $Z^2$ groups. In certain embodiments, ring B is a 6-7 membered bicycle carbocycle, wherein any 6-7 membered bicycle carbocycle is optionally substituted with 1, 2, or 3 $Z^2$ groups. In certain embodiments, ring B is a 6-7 membered bicycle carbocycle, wherein any 6-7 membered bicycle carbocycle is optionally substituted with 1 or 2 $Z^2$ groups.

In certain embodiments of Formula (I), (Ia), and (Ib), ring B is bicyclo[3.1.0]hex-2-ene, wherein bicyclo[3.1.0]hex-2-ene is optionally substituted with 1, 2, 3, 4 or 5 $Z^2$ groups. In certain embodiments, ring B is bicyclo[3.1.0]hex-2-ene, wherein bicyclo[3.1.0]hex-2-ene is optionally substituted with 1, 2, or 3 $Z^2$ groups. In certain embodiments, ring B is bicyclo[3.1.0]hex-2-ene, wherein bicyclo[3.1.0]hex-2-ene is optionally substituted with 1 or 2 $Z^2$ groups.

In certain embodiments of Formula (I), (Ia), and (Ib), ring B is a 6-7-membered monocycle carbocycle. In certain embodiments, ring B, including the two carbon atoms to which it is fused to ring A, is a 6-membered bicycle carbocycle. In certain embodiments, ring B is a 6-membered monocycle heterocycle. In certain embodiments, ring B is a 10-membered bicycle heterocycle.

In certain embodiments of Formula (I), (Ia), and (Ib), ring B is

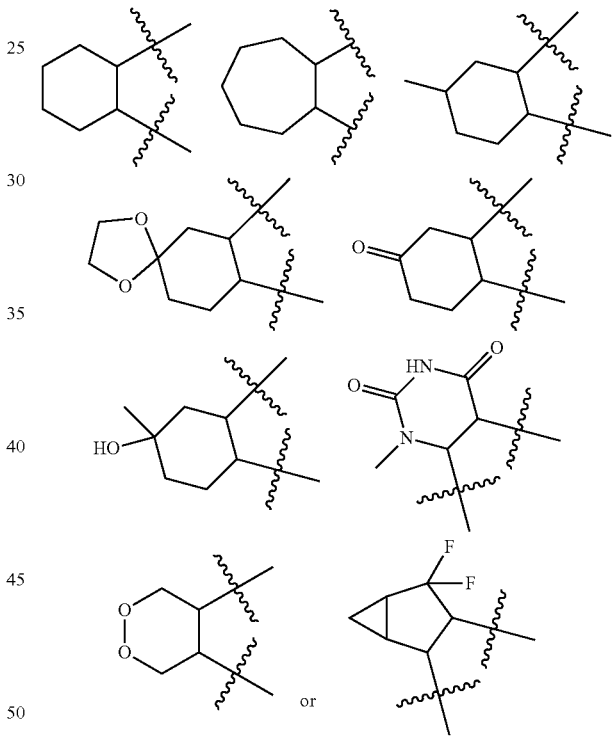

In one aspect, the compounds contain at least one $Z^2$ moiety. In one aspect, the compounds contain 1, 2 or 3 $Z^2$ moiety. In certain embodiments of Formula (I), (Ia), and (Ib), each $Z^2$ is independently $(C_1-C_6)$alkyl, halo, oxo, or —OR$^{n2}$, wherein any $(C_1-C_6)$alkyl of $Z^2$ is optionally substituted with 1, 2, 3, 4 or 5 halo groups. In certain embodiments, each $Z^2$ is independently $(C_1-C_6)$alkyl, halo, oxo, or —OR$^{n2}$, wherein any $(C_1-C_6)$alkyl of $Z^2$ is optionally substituted with 1, 2, or 3 halo groups. In certain embodiments, $Z^2$ is an optionally substituted $(C_1-C_6)$alkyl (e.g., —CH$_3$ and —CF$_3$), halo, or oxo.

In certain embodiments of Formula (I), (Ia), and (Ib), each $Z^2$ is independently methyl, fluoro, oxo, or OH. In certain embodiments of Formula (I), (Ia), and (Ib), each $Z^2$ is independently methyl, fluoro, or OH.

In certain embodiments of Formula (I), (IA), and (Ib), $R^1$ is phenyl, 9-10-membered bicycle heterocycle, 5-6 membered monocycle heteroaryl or 3-7 member carbocycle, wherein any phenyl, 9-10-membered bicyclic heterocycle, 5-6 membered monocycle heteroaryl or 3-7 member carbocycle of $R^1$ is optionally substituted with 1, 2, 3, 4, or 5 $Z^3$ groups. In certain embodiments of Formula (I), (Ia), and (Ib), $R^1$ is phenyl, 9-10-membered bicycle heterocycle, or 5-6 membered monocycle heteroaryl, wherein any phenyl, 9-10-membered bicycle heterocycle, or 5-6 membered monocycle heteroaryl of $R^1$ is optionally substituted with 1, 2, 3, 4, or 5 $Z^3$ groups. In certain embodiments, $R^1$ is phenyl or 5-6 membered monocycle heteroaryl, wherein any phenyl or 5-6 membered monocycle heteroaryl of $R^1$ is optionally substituted with 1, 2, or 3 $Z^3$ groups. In certain embodiments, $R^1$ is phenyl or 5-6 membered monocycle heteroaryl, wherein any phenyl or 5-6 membered monocycle heteroaryl of $R^1$ is optionally substituted with 1 or 2 $Z^3$ groups.

In certain embodiments of Formula (I), (Ia), and (Ib), $R^1$ is phenyl, wherein the phenyl is optionally substituted with 1, 2, or 3 $Z^3$ groups. In certain embodiments, $R^1$ is phenyl, wherein the phenyl is optionally substituted with 1 or 2 $Z^3$ groups.

In certain embodiments of Formula (I), (Ia) and (Ib), $R^1$ is pyridinyl, thiofuranyl, imidazolyl, benzothiofuranyl, thiazolyl, or pyrazolyl, in which any of the ring are optionally substituted with 1, 2, or 3 $Z^3$ groups. In certain embodiments of Formula (I), (Ia), and (Ib), $R^1$ is tetrahydrofuranyl, which is optionally substituted with 1, 2, or 3 $Z^3$ groups. In certain embodiments of Formula (I), (Ia), and (Ib), $R^1$ is cyclobutyl, which is optionally substituted with 1, 2, or 3 $Z^3$ groups.

In one aspect, the compounds contain at least one $Z^3$ moiety. In certain embodiments of Formula (I), (Ia), and (Ib), each $Z^3$ is independently $(C_1-C_6)$alkyl, halo, —CN, —NO$_2$, or —C(O)NR$^{q3}$R$^{r3}$, wherein any $(C_1-C_6)$alkyl of $Z^3$ is optionally substituted with 1, 2, 3, 4 or 5 halo groups. In certain embodiments, each $Z^3$ is independently $(C_1-C_6)$alkyl, halo, —CN, —NO$_2$, or —C(O)NR$^{q3}$R$^{r3}$, wherein any $(C_1-C_6)$alkyl of $Z^3$ is optionally substituted with 1, 2, or 3 halo groups.

In certain embodiments of Formula (I), (Ia), and (Ib), each $Z^3$ is independently methyl, fluoro, bromo, chloro, CN, NO$_2$, —C(O)NH$_2$, or —CF$_3$ In certain embodiments of Formula (I), (Ia), and (Ib), each $Z^3$ is fluoro.

In certain embodiments of Formula (I), (Ia), and (Ib), R is

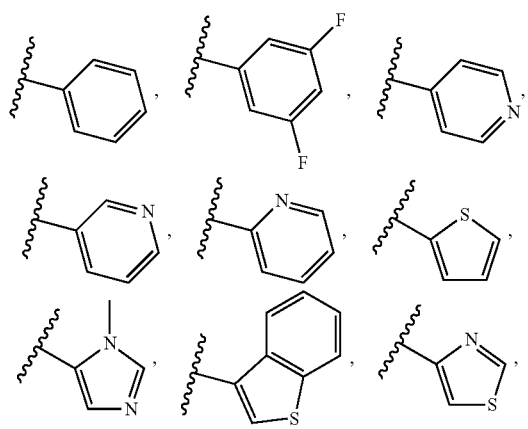

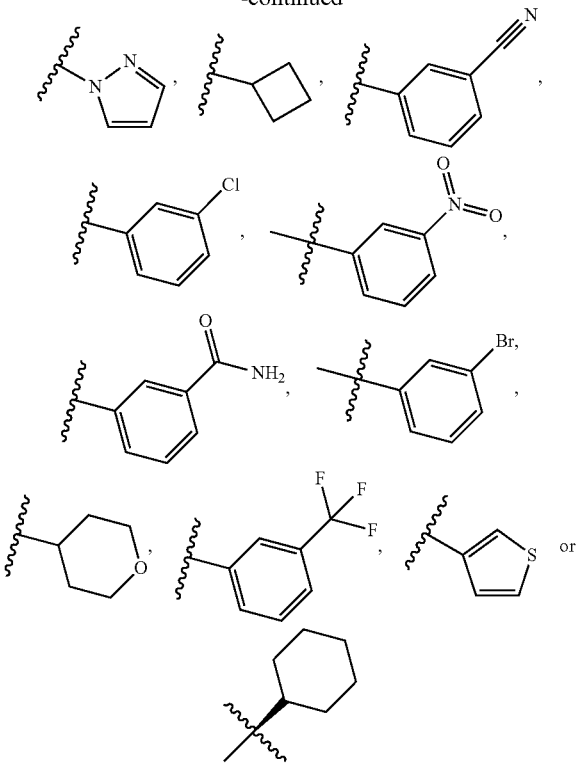

In certain embodiments of Formula (I), (Ia), and (Ib), $R^2$ is $(C_1-C_6)$alkyl.

In certain embodiments of Formula (I), (Ia), and (Ib), $R^2$ is methyl.

In certain embodiments of Formula (I), (Ia), and (Ib), $R^2$ is optionally substituted with 1, 2, or 3 halo groups.

In certain embodiments of Formula (I), (Ia), and (Ib), $R^3$ is phenyl, 9-10 membered bicyclic aryl, or 8-10 membered bicyclic heterocycle, wherein any phenyl, 9-10 membered bicyclic aryl or 8-10 membered bicyclic heterocycle of $R^3$ is optionally substituted with 1, 2 or 3 $Z^4$ groups.

In certain embodiments of Formula (I), (Ia), and (Ib), $R^3$ is phenyl or 9-10 membered bicycle aryl, wherein any phenyl or 9-10 membered bicycle aryl of $R^4$ is optionally substituted with 1, 2 or 3 $Z^4$ groups.

In certain embodiments of Formula (I), (Ia), and (Ib), $R^3$ is phenyl, naphthyl or isoindolin-1-one, wherein any phenyl, naphthyl, or isoindolin-1-one of $R^4$ is optionally substituted with 1, 2 or 3 $Z^4$ groups. In certain embodiments, $R^3$ is phenyl, wherein the phenyl of $R^4$ is optionally substituted with 1, 2 or 3 $Z^4$ groups.

In one aspect, the compounds contain at least one $Z^4$ moiety. In certain embodiments of Formula (I), (Ia), and (Ib), the compounds contain 1, 2, or 3 $Z^4$ moiety. In certain embodiments of Formula (I), (Ia), and (Ib), the compounds contain 2 $Z^4$ moieties. In certain embodiments of Formula (I), (Ia), and (Ib), the compounds contain 1 $Z^4$ moiety. In certain embodiments of Formula (I), (Ia), and (Ib), each $Z^4$ is independently $(C_1-C_6)$alkyl, halo, —CN, —OR$^{r4}$, —NR$^{q4}$R$^{r4}$, or oxo, wherein any $(C_1-C_6)$alkyl, of $Z^4$ is optionally substituted with 1, 2, 3, 4 or 5 halo groups. In certain embodiments, each $Z^4$ is independently $(C_1-C_6)$alkyl, halo, —CN, —OR$^4$, —NR$^{q4}$R$^{r4}$, or oxo, wherein any $(C_1-C_6)$alkyl, of $Z^4$ is optionally substituted with 1, 2, or 3 halo groups.

In certain embodiments of Formula (I), (Ia), and (Ib), each $Z^4$ is independently $(C_1-C_6)$alkyl, halo, —CN, —O$(C_1-C_6)$alkyl, —N$((C_1-C_6)$alkyl$)_2$, or oxo.

In certain embodiments of Formula (I), (Ia), and (Ib), each $Z^4$ is independently methyl, —OCH$_3$, fluoro, chloro, —N(CH$_3)_2$, or oxo.

In certain embodiments of Formula (I), (Ia), and (Ib), $R^3$ is:

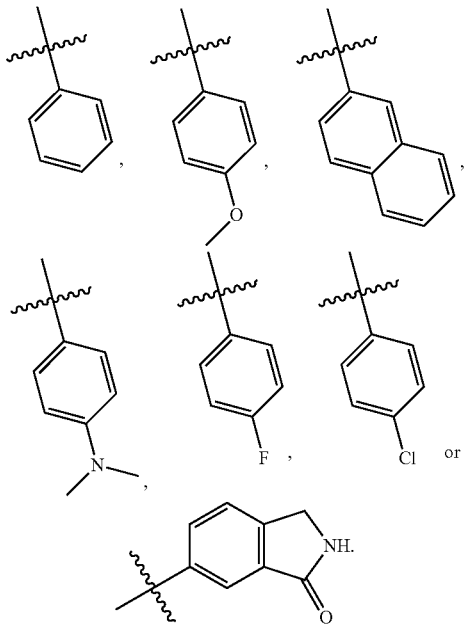

In certain embodiments of Formula (I), (Ia), and (Ib), $R^4$ is H.

It is understood that any variable for ring B of Formula (I) and (Ia) may be combined with any variable of $R^4$ of Formula (I) and (Ia) the same as if each and every combination were specifically and individually listed. For example, in one variation of Formula (I) and (Ia), ring B is an optionally substituted 6-7 member carbocycle and $R^4$ is hydrogen. In another variation, ring B is a 6-7 member carbocycle substituted with —CF$_3$ and $R^4$ is hydrogen.

It is understood that any variable for ring B of Formula (I) and (Ia) may be combined with any variable of $R^1$ of Formula (I) and (Ia) the same as if each and every combination were specifically and individually listed. For example, in one variation of Formula (I) and (Ia), ring B is an optionally substituted 6-7 member carbocycle and $R^1$ is optionally substituted and is phenyl, pyridinyl, thiofuranyl, imidazolyl, benzothiofuranyl, thiazolyl, pyrazolyl, tetrahydrofuranyl, or cyclobutyl. In another variation, ring B is an optionally substituted 6-7 member carbocycle and $R^1$ is optionally substituted and is phenyl. In another variation, ring B is a 6-7 member carbocycle substituted with —CF$_3$ and $R^1$ is optionally substituted and is phenyl, pyridinyl, thiofuranyl, imidazolyl, benzothiofuranyl, thiazolyl, pyrazolyl, tetrahydrofuranyl, or cyclobutyl. In another variation, ring B is a 6-7 membered carbocycle substituted with —CF$_3$ and $R^1$ is optionally substituted and is phenyl.

It is understood that any variable for ring B of Formula (I) and (Ia) may be combined with any variable of $R^2$ of Formula (I) and (Ia) the same as if each and every combination were specifically and individually listed. For example, in one variation of Formula (I) and (Ia), ring B is an optionally substituted 6-7 membered carbocycle and $R^2$ is $(C_1-C_6)$alkyl, such as methyl. In another variation, ring B is a 6-7 membered carbocycle substituted with —CF$_3$ and $R^2$ is $(C_1-C_5)$alkyl, such as methyl It is understood that any variable for ring B of Formula (I) and (Ia) may be combined with any variable of $R^3$ of Formula (I) and (Ia) the same as if each and every combination were specifically and individually listed. For example, in one variation of Formula (I) and (Ia), ring B is an optionally substituted 6-7 member carbocycle and $R^3$ is phenyl, naphthyl or isoindolin-1-one, wherein any phenyl, naphthyl, or isoindolin-1-one of $R^4$ is optionally substituted with 1, 2 or 3 $Z^4$ groups. In another variation, ring B is a 6-7 member carbocycle substituted with —CF$_3$ and $R^3$ is phenyl, naphthyl or isoindolin-1-one, wherein any phenyl, naphthyl, or isoindolin-1-one of $R^4$ is optionally substituted with 1, 2 or 3 $Z^4$ groups.

It is understood that any variable for $R^2$ of Formula (I) and (Ia) may be combined with any variable of $R^3$ of Formula (I) and (Ia) the same as if each and every combination were specifically and individually listed. For example, in one variation of Formula (I) and (Ia), $R^2$ is $(C_1-C_6)$alkyl, such as methyl and $R^3$ is phenyl, naphthyl or isoindolin-1-one, wherein any phenyl, naphthyl, or isoindolin-1-one of $R^4$ is optionally substituted with 1, 2 or 3 $Z^4$ groups.

In certain embodiments of Formula (I) and (Ia), where the moiety

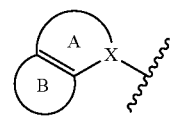

has an A ring as detailed herein, the compounds may have any one or more of the following structural features:

(a) ring B is a 5-7 membered monocycle carbocycle (e.g., cycloheptane, cyclohexane and cyclopentane) optionally substituted with 1, 2, 3, 4 or 5 $Z^2$ groups (e.g., —CH$_3$, —CF$_3$, —OH, halo or oxo), such as unsubstituted cyclohexane or a mono- or di-substituted cyclohexane;

(b) $R^4$ is H;

(c) R is phenyl, 9-10-membered bicycle heterocycle (e.g., tetrahydrofuranyl), 5-6 membered monocycle heteroaryl (e.g., pyridinyl, thiofuranyl, imidazolyl, benzothiofuranyl, thiazolyl, pyrazolyl), or 3-7 member carbocycle (e.g., cyclobutyl), wherein any phenyl, 9-10-membered bicycle heterocycle, 5-6 membered monocycle heteroaryl or 3-7 member carbocycle of $R^1$ is optionally substituted with one or more $Z^3$ groups;

(d) $R^2$ is $(C_1-C_6)$alkyl (e.g., methyl); and (e) $R^3$ is phenyl or 9-10 membered bicyclic aryl, wherein any phenyl or 9-10 membered bicycle aryl of $R^4$ is optionally substituted with 1, 2 or 3 $Z^4$ groups (e.g., phenyl, naphthyl, or isoindolin-1-one).

In one variation, the compounds conform to at least one of features (a)-(e). In another variation, the compounds conform to two or more (and in certain variations, all) of features (a)-(e). In a particular variation, the compounds conform to feature (a). In another variation, the compounds confirm to feature (a) and (b).

In certain embodiments of Formula (I) and (Ia), where the moiety

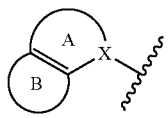

has a B ring as detailed herein, the compounds may have any one or more of the following structural features:
(a) ring A is a 5-6 membered heteroaryl ring (e.g., a 5-6 membered heteroaryl ring bearing, 1-2 annular nitrogen atoms and 3-4 annular carbon atoms) optionally substituted with 1, 2, or $3Z^1$ groups (e.g, —CH$_3$, —OF$_3$, halo or —NH$_2$). For example, ring A may be a 5 membered heteroaryl containing 2 annular nitrogen atoms, e.g., pyrazolyl (e.g., —CF$_3$ substituted pyrazolyl) and imidazolyl (e.g., —NH$_2$ substituted imidazolyl);
(b) $R^4$ is H;
(c) $R^1$ is phenyl, 9-10-membered bicyclic heterocycle (e.g., tetrahydrofuranyl), 5-6 membered monocycle heteroaryl (e.g., pyridinyl, thiofuranyl, imidazolyl, benzothiofuranyl, thiazolyl, pyrazolyl), or 3-7 member carbocycle (e.g, cyclobutyl), wherein any phenyl, 9-10-membered bicycle heterocycle, 5-6 membered monocycle heteroaryl or 3-7 member carbocycle of $R^1$ is optionally substituted with 1, 2, 3, 4, or 5 $Z^3$ groups;
(d) $R^2$ is (C$_1$-C$_6$)alkyl; (e.g., methyl); and
(e) $R^3$ is phenyl or 9-10 membered bicyclic aryl, wherein any phenyl or 9-10 membered bicyclic aryl of $R^4$ is optionally substituted with 1, 2 or 3 $Z^4$ groups (e.g., phenyl, naphthyl, or isoindolin-1-one).

In one variation, the compounds conform to at least one of features (a)-(e). In another variation, the compounds conform to two or more (and in certain variations, all) of features (a)-(e). In a particular variation, the compounds conform to feature (a). In another variation, the compounds conform to features (a) and (h).

In certain embodiments, the compound of Formula (I), (Ia), or (Ib), is selected from a compound of Formula (II)

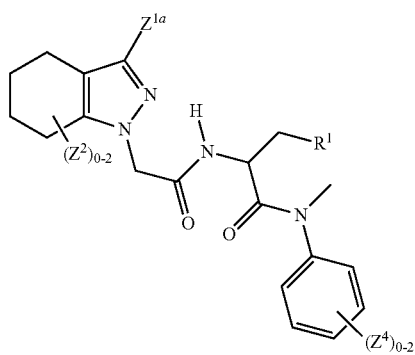

(II)

wherein $R^1$, $Z^{1a}$, $Z^2$, and $Z^4$ are as defined herein.

In certain embodiments of Formula (II), each $Z^2$ is independently (C$_1$-C$_6$)alkyl, halo, oxo, or —OR$^{n2}$, wherein any (C$_1$-C$_6$)alkyl of $Z^2$ is optionally substituted with 1, 2, 3, 4 or 5 halo groups. In certain embodiments, each $Z^2$ is independently (C$_1$-C$_6$)alkyl, halo, oxo, or —OR$^{n2}$, wherein any (C$_1$-C$_6$)alkyl of $Z^2$ is optionally substituted with 1, 2, or 3 halo groups. In certain embodiments, $Z^2$ is an optionally substituted (C$_1$-C$_6$)alkyl (e.g., —CH$_3$ and —CF$_3$), halo, or oxo.

In certain embodiments of Formula (II), each $Z^2$ is independently methyl, fluoro, oxo, or OH. In certain embodiments of Formula (II), each $Z^2$ is independently methyl, fluoro, or OH.

In certain embodiments of Formula (II), $R^1$ is phenyl, 9-10-membered bicyclic heterocycle, 5-6 membered monocyclic heteroaryl or 3-7 member carbocycle, wherein any phenyl, 9-10-membered bicyclic heterocycle, 5-6 membered monocycle heteroaryl or 3-7 member carbocycle of $R^1$ is optionally substituted with 1, 2, 3, 4, or 5 $Z^3$ groups. In certain embodiments of Formula (II), $R^1$ is phenyl, 9-10-membered bicyclic heterocycle, or 5-6 membered monocyclic heteroaryl, wherein any phenyl, 9-10-membered bicyclic heterocycle, or 5-6 membered monocycle heteroaryl of $R^1$ is optionally substituted with 1, 2, 3, 4, or 5 $Z^3$ groups. In certain embodiments, $R^1$ is phenyl or 5-6 membered monocycle heteroaryl, wherein any phenyl or 5-6 membered monocycle heteroaryl of $R^1$ is optionally substituted with 1, 2, or 3 $Z^3$ groups. In certain embodiments, $R^1$ is phenyl or 5-6 membered monocycle heteroaryl, wherein any phenyl or 5-6 membered monocycle heteroaryl of $R^1$ is optionally substituted with 1 or 2 $Z^3$ groups.

In certain embodiments of Formula (II), $R^1$ is phenyl, wherein the phenyl is optionally substituted with 1, 2, or 3 $Z^3$ groups. In certain embodiments, $R^1$ is phenyl, wherein the phenyl is optionally substituted with 1 or 2 $Z^3$ groups.

In certain embodiments of Formula (II), $R^1$ is pyridinyl, thiofuranyl, benzothiofuranyl, thiazolyl, or pyrazolyl, in which any of the ring are optionally substituted with 1, 2, or 3 $Z^3$ groups. In certain embodiments of Formula (II), R is tetrahydrofuranyl, which is optionally substituted with 1, 2, or 3 $Z^3$ groups. In certain embodiments of Formula (II), R is cyclobutyl, which is optionally substituted with 1, 2, or 3 $Z^3$ groups.

In one aspect, the compounds contain at least one Z moiety. In certain embodiments of Formula (II), each $Z^3$ is independently (C$_1$-C$_6$)alkyl, halo, —CN, —NO$_2$, or —C(O)NR$^{q3}$R$'^3$, wherein any (C$_1$-C$_6$)alkyl of $Z^3$ is optionally substituted with 1, 2, 3, 4 or 5 halo groups. In certain embodiments, each $Z^3$ is independently (C$_1$-C$_6$)alkyl, halo, —CN, —NO$_2$, or —C(O)NR$^{q3}$R$'^3$, wherein any (C$_1$-C$_6$) alkyl of $Z^3$ is optionally substituted with 1, 2, or 3 halo groups.

In certain embodiments of Formula (II), each $Z^3$ is independently methyl, fluoro, bronco, chloro, CN, NO$_2$, —C(O)NH$_2$, or —CF$_3$.

In certain embodiments of Formula (II), each $Z^3$ is fluoro.

In certain embodiments of Formula (II), $R^1$ is:

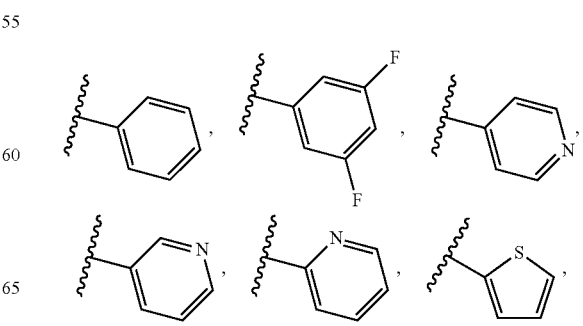

-continued

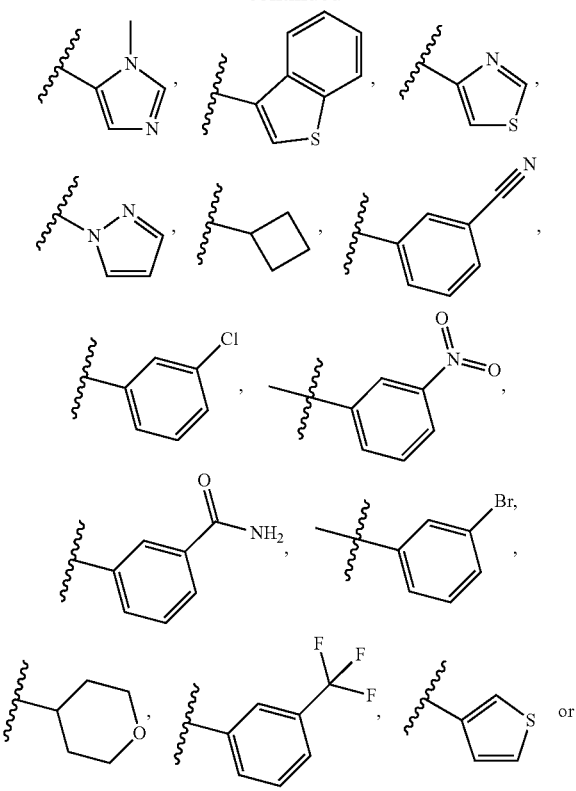

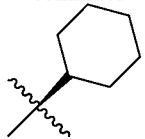

-continued

In certain embodiments of Formula (II), the compounds contain 2 $Z^4$ moieties. In certain embodiments of Formula (II), the compounds contain 1 $Z^4$ moiety. In certain embodiments of Formula (II), each $Z^4$ is independently $(C_1-C_6)$ alkyl, halo, —CN, —$OR^{n4}$, —$NR^{q4}R^{r4}$, or oxo, wherein any $(C_1-C_6)$alkyl of $Z^4$ is optionally substituted with 1, 2, 3, 4 or 5 halo groups. In certain embodiments, each $Z^4$ is independently $(C_1-C_6)$alkyl, halo, —CN, —$OR^{n4}$, —$NR^{q4}R^{r4}$, or oxo, wherein any $(C_1-C_6)$alkyl of $Z^4$ is optionally substituted with 1, 2, or 3 halo groups.

In certain embodiments of Formula (II), each $Z^4$ is independently $(C_1-C_6)$alkyl, halo, —CN, —O$(C_1-C_6)$alkyl, —N$((C_1-C_6)$alkyl$)_2$, or oxo.

In certain embodiments of Formula (II), each $Z^4$ is independently methyl, —$OCH_3$, fluoro, chloro, —$N(CH_3)_2$, or oxo.

In certain embodiments of the compound of Formula (II), $Z^{1a}$ is H or $Z^1$, wherein each $Z^1$ is independently $(C_1-C_6)$ alkyl, halo, —OH, or —$NR^{q1}R^{r1}$, wherein any $(C_1-C_6)$alkyl of $Z^1$ is optionally substituted with 1, 2, or 3 halo groups. In certain embodiments, each $Z^1$ is independently —$CF_3$, halo, —OH, or —$NH_2$. In certain embodiments, each $Z^1$ is independently —$CF_3$ or —OH.

The present disclosure provides the following compounds or a pharmaceutically acceptable salt thereof.

| Compound Number | Compound Structure |
|---|---|
| Compound 1 | 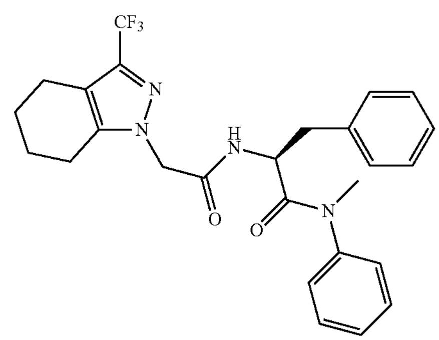 [SMILES: CN(C(=O)[C@H](Cc1ccccc1)NC(=O)Cn1nc(C(F)(F)F)c2c1CCCC2)c1ccccc1] |
| Compound 2 | 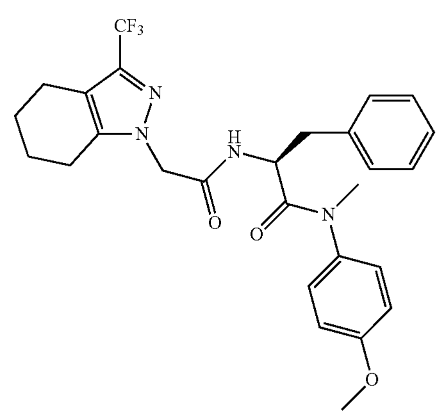 [SMILES: COc1ccc(N(C)C(=O)[C@H](Cc2ccccc2)NC(=O)Cn2nc(C(F)(F)F)c3c2CCCC3)cc1] |

-continued
| Compound Number | Compound Structure |
|---|---|
| Compound 3 | 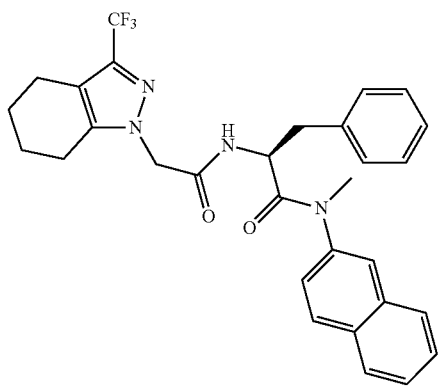 [SMILES: CN(C(=O)[C@H](Cc1ccccc1)NC(=O)Cn1nc(C(F)(F)F)c2c1CCCC2)c1ccc2ccccc2c1] |
| Compound 4 | 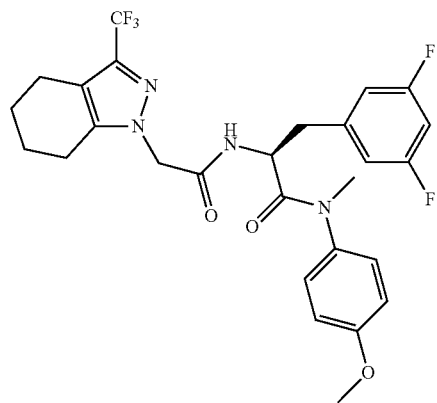 [SMILES: COc1ccc(N(C)C(=O)[C@H](Cc2cc(F)cc(F)c2)NC(=O)Cn2nc(C(F)(F)F)c3c2CCCC3)cc1] |
| Compound 5 | 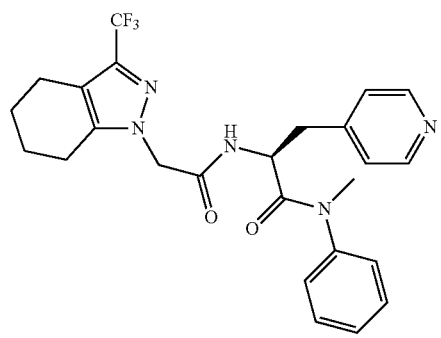 [SMILES: CN(C(=O)[C@H](Cc1ccncc1)NC(=O)Cn1nc(C(F)(F)F)c2c1CCCC2)c1ccccc1] |
| Compound 6 | 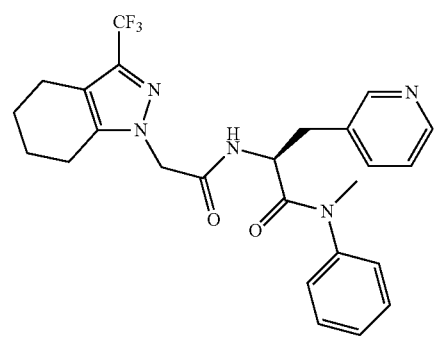 [SMILES: CN(C(=O)[C@H](Cc1cccnc1)NC(=O)Cn1nc(C(F)(F)F)c2c1CCCC2)c1ccccc1] |

-continued
| Compound Number | Compound Structure |
|---|---|
| Compound 7 | 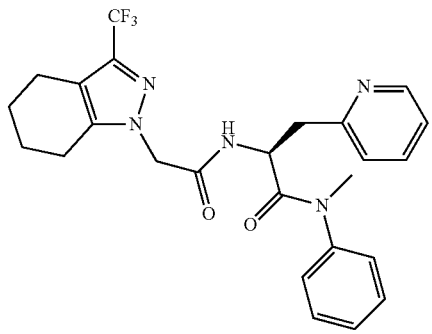 [SMILES: CN(C(=O)[C@H](Cc1ccccn1)NC(=O)Cn1nc(C(F)(F)F)c2c1CCCC2)c1ccccc1] |
| Compound 8 | 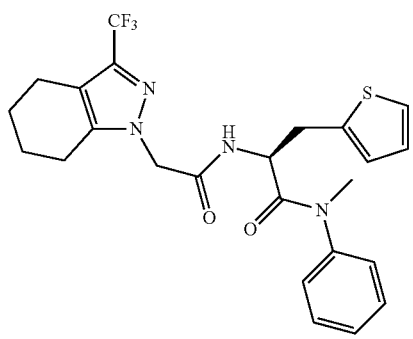 [SMILES: CN(C(=O)[C@H](Cc1cccs1)NC(=O)Cn1nc(C(F)(F)F)c2c1CCCC2)c1ccccc1] |
| Compound 9 | 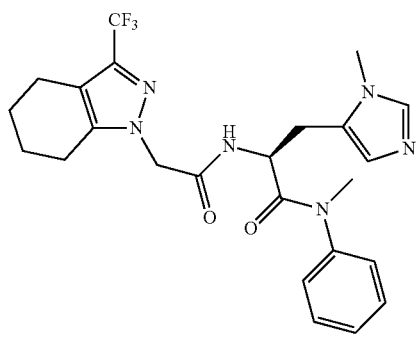 [SMILES: CN(C(=O)[C@H](Cc1cncn1C)NC(=O)Cn1nc(C(F)(F)F)c2c1CCCC2)c1ccccc1] |
| Compound 10 | 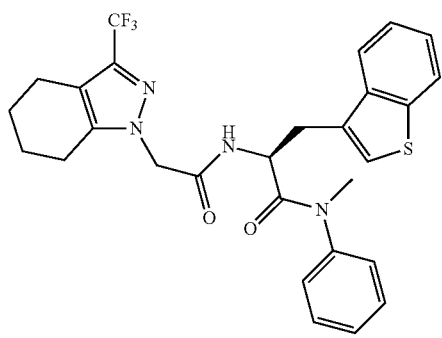 [SMILES: CN(C(=O)[C@H](Cc1csc2ccccc12)NC(=O)Cn1nc(C(F)(F)F)c2c1CCCC2)c1ccccc1] |

-continued
| Compound Number | Compound Structure |
| --- | --- |
| Compound 11 | 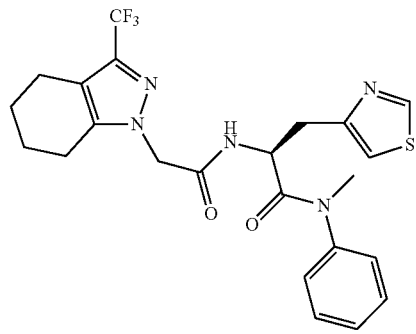 [SMILES: CN(C(=O)[C@H](Cc1cscn1)NC(=O)Cn1nc(C(F)(F)F)c2c1CCCC2)c1ccccc1] |
| Compound 12 | 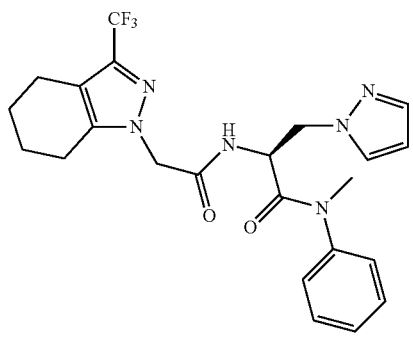 [SMILES: CN(C(=O)[C@H](Cn1cccn1)NC(=O)Cn1nc(C(F)(F)F)c2c1CCCC2)c1ccccc1] |
| Compound 13 | 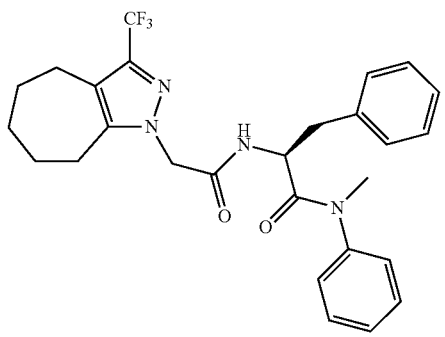 [SMILES: CN(C(=O)[C@H](Cc1ccccc1)NC(=O)Cn1nc(C(F)(F)F)c2c1CCCCC2)c1ccccc1] |
| Compound 14 | 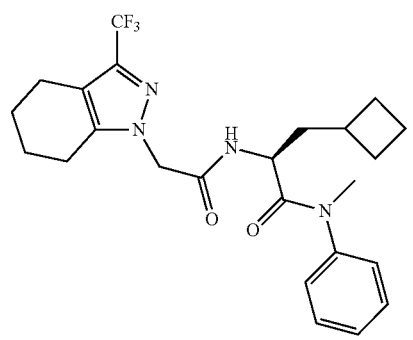 [SMILES: CN(C(=O)[C@H](CC1CCC1)NC(=O)Cn1nc(C(F)(F)F)c2c1CCCC2)c1ccccc1] |

-continued
| Compound Number | Compound Structure |
|---|---|
| Compound 15 | 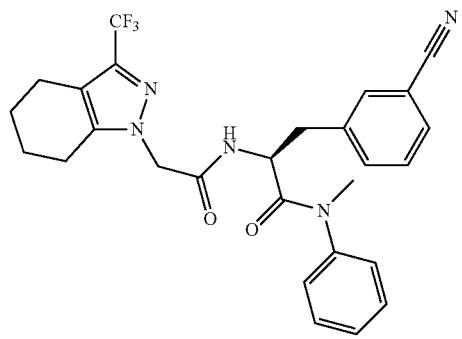 [SMILES: CN(C(=O)[C@H](Cc1cccc(C#N)c1)NC(=O)Cn1nc(C(F)(F)F)c2c1CCCC2)c1ccccc1] |
| Compound 16 | 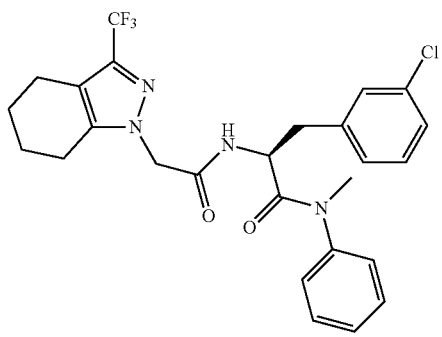 [SMILES: CN(C(=O)[C@H](Cc1cccc(Cl)c1)NC(=O)Cn1nc(C(F)(F)F)c2c1CCCC2)c1ccccc1] |
| Compound 17 | 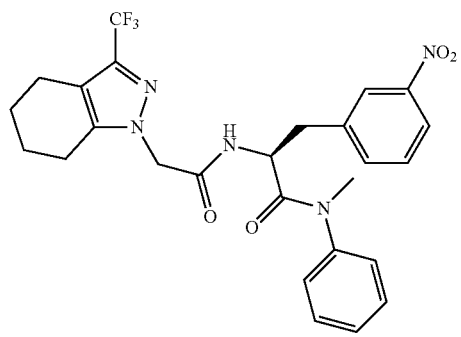 [SMILES: CN(C(=O)[C@H](Cc1cccc([N+](=O)[O-])c1)NC(=O)Cn1nc(C(F)(F)F)c2c1CCCC2)c1ccccc1] |
| Compound 18 | 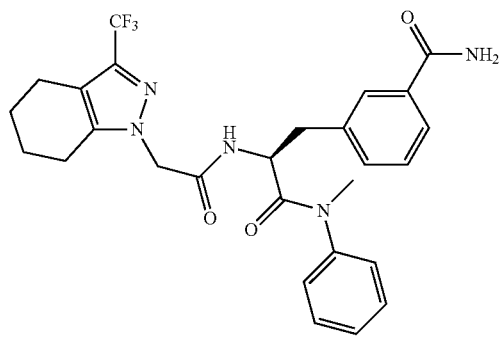 [SMILES: CN(C(=O)[C@H](Cc1cccc(C(N)=O)c1)NC(=O)Cn1nc(C(F)(F)F)c2c1CCCC2)c1ccccc1] |

-continued
| Compound Number | Compound Structure |
|---|---|
| Compound 19 | 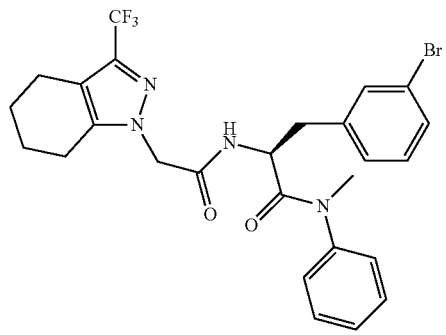 [SMILES: CN(C(=O)[C@H](Cc1cccc(Br)c1)NC(=O)Cn1nc(C(F)(F)F)c2c1CCCC2)c1ccccc1] |
| Compound 20 | 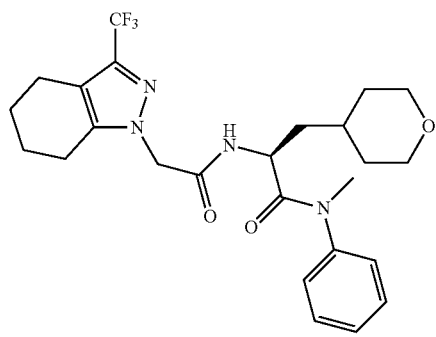 [SMILES: CN(C(=O)[C@H](CC1CCOCC1)NC(=O)Cn1nc(C(F)(F)F)c2c1CCCC2)c1ccccc1] |
| Compound 21 | 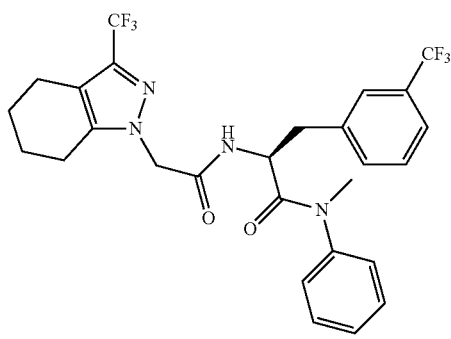 [SMILES: CN(C(=O)[C@H](Cc1cccc(C(F)(F)F)c1)NC(=O)Cn1nc(C(F)(F)F)c2c1CCCC2)c1ccccc1] |
| Compound 22 | 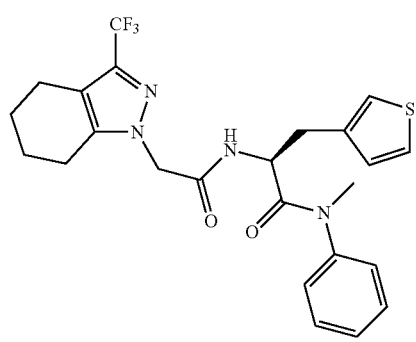 [SMILES: CN(C(=O)[C@H](Cc1ccsc1)NC(=O)Cn1nc(C(F)(F)F)c2c1CCCC2)c1ccccc1] |

-continued
| Compound Number | Compound Structure |
|---|---|
| Compound 23 | 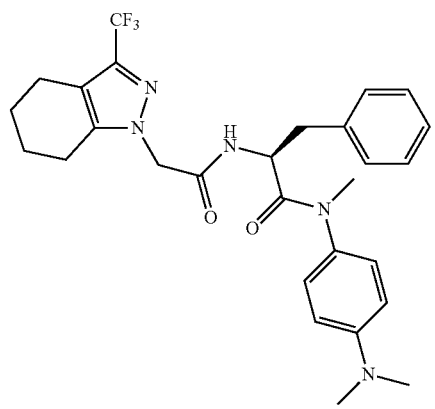 [SMILES: CN(C)c1ccc(N(C)C(=O)[C@H](Cc2ccccc2)NC(=O)Cn2nc(C(F)(F)F)c3c2CCCC3)cc1] |
| Compound 24 | 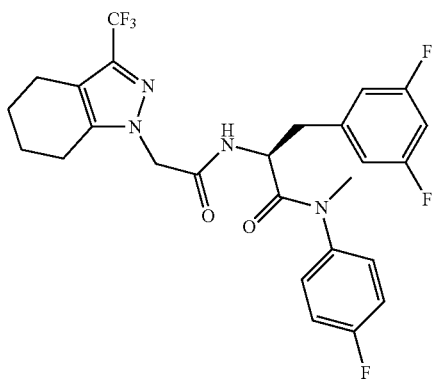 [SMILES: CN(C(=O)[C@H](Cc1cc(F)cc(F)c1)NC(=O)Cn1nc(C(F)(F)F)c2c1CCCC2)c1ccc(F)cc1] |
| Compound 25 | 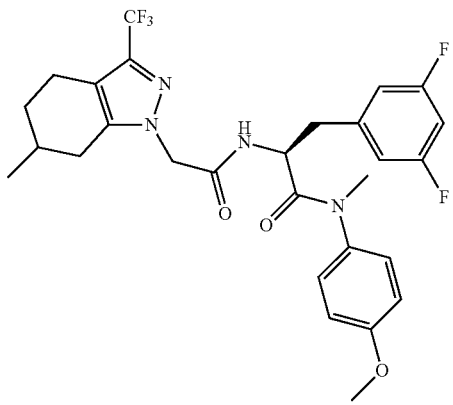 [SMILES: COc1ccc(N(C)C(=O)[C@H](Cc2cc(F)cc(F)c2)NC(=O)Cn2nc(C(F)(F)F)c3c2CC(C)CC3)cc1] |
| Compound 26 | 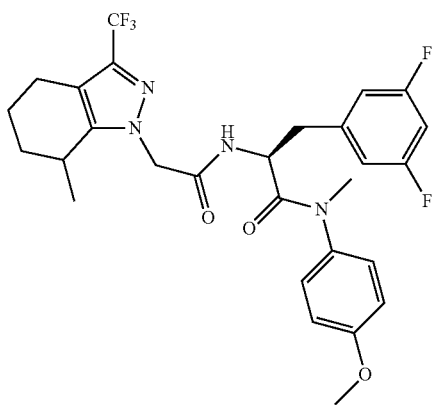 [SMILES: COc1ccc(N(C)C(=O)[C@H](Cc2cc(F)cc(F)c2)NC(=O)Cn2nc(C(F)(F)F)c3c2C(C)CCC3)cc1] |

-continued

| Compound Number | Compound Structure |
|---|---|
| Compound 27 | 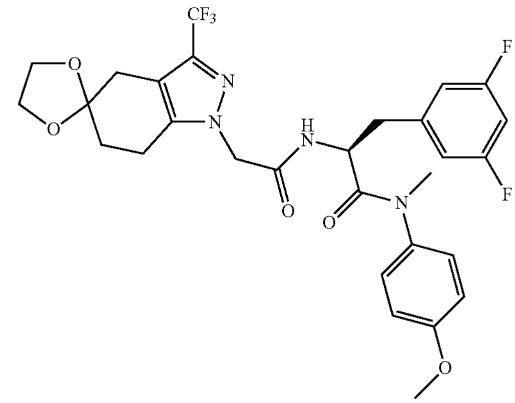 [SMILES: COc1ccc(N(C)C(=O)[C@H](Cc2cc(F)cc(F)c2)NC(=O)Cn2nc(C(F)(F)F)c3c2CCC2(C3)OCCO2)cc1] |
| Compound 28 | 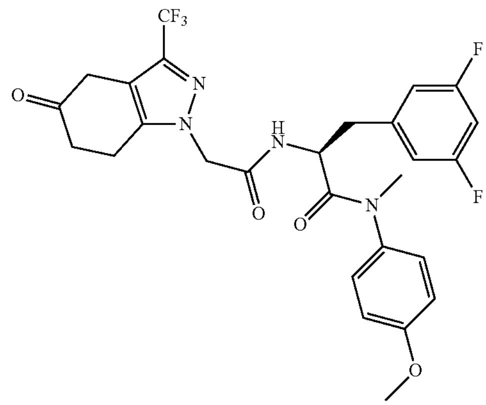 [SMILES: COc1ccc(N(C)C(=O)[C@H](Cc2cc(F)cc(F)c2)NC(=O)Cn2nc(C(F)(F)F)c3c2CCC(=O)C3)cc1] |
| Compound 29 | 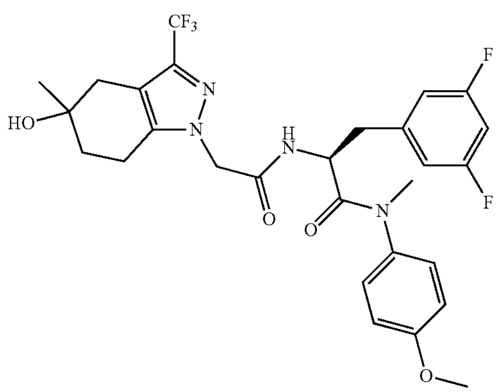 [SMILES: COc1ccc(N(C)C(=O)[C@H](Cc2cc(F)cc(F)c2)NC(=O)Cn2nc(C(F)(F)F)c3c2CCC(C)(O)C3)cc1] |
| Compound 30 | 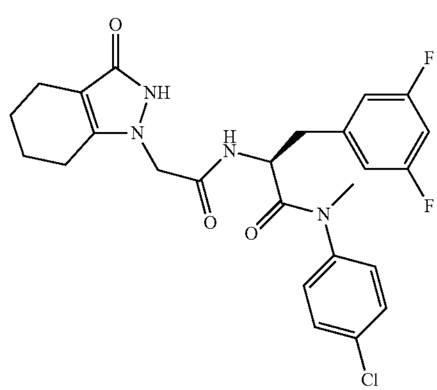 [SMILES: CN(C(=O)[C@H](Cc1cc(F)cc(F)c1)NC(=O)Cn1[nH]c(=O)c2c1CCCC2)c1ccc(Cl)cc1] |

-continued
| Compound Number | Compound Structure |
|---|---|
| Compound 31 | 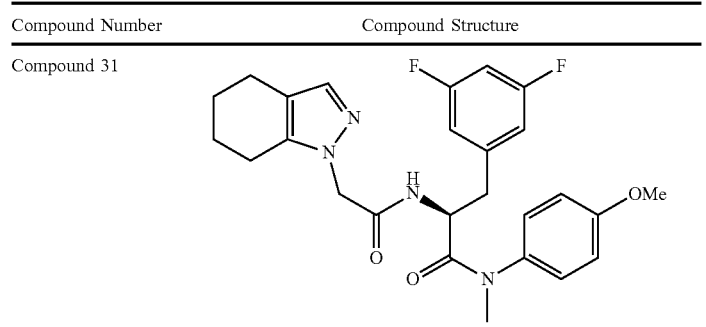 |
| Compound 32 | 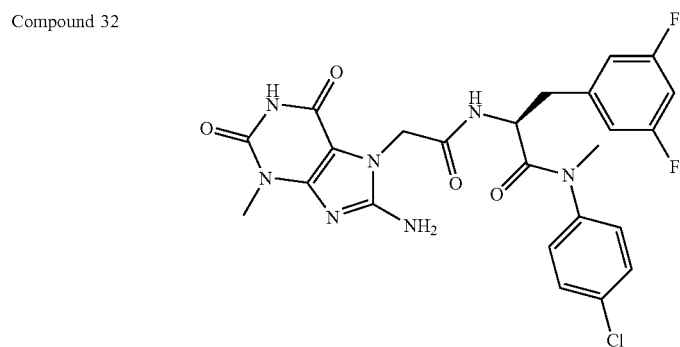 |
| Compound 33 | 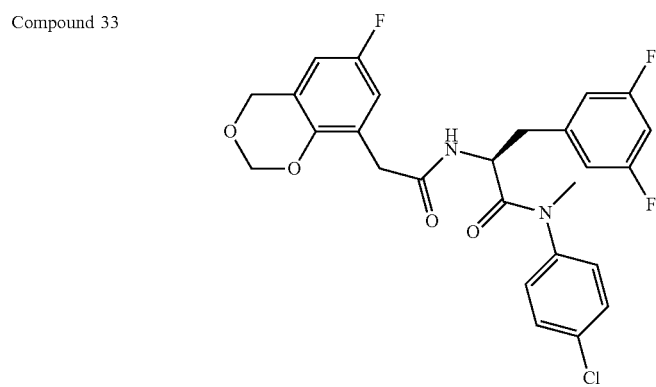 |
| Compound 34 | 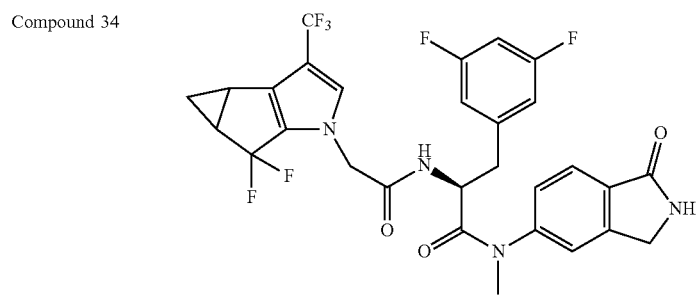 |

| Compound Number | Compound Structure |
|---|---|
| Compound 35 | 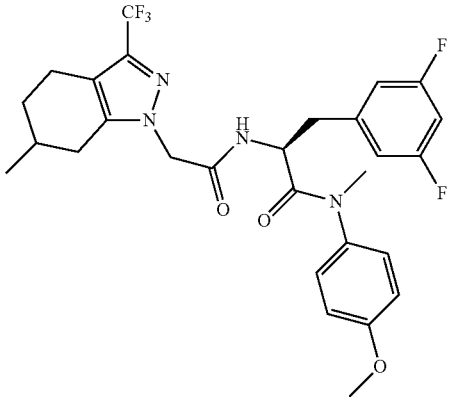 [SMILES: COc1ccc(N(C)C(=O)[C@H](Cc2cc(F)cc(F)c2)NC(=O)Cn2nc(C(F)(F)F)c3c2CC(C)CC3)cc1] |
The present disclosure provides the following compounds or a pharmaceutically acceptable salt thereof.
| Compound Number | Compound Structure |
|---|---|
| Compound 1z | 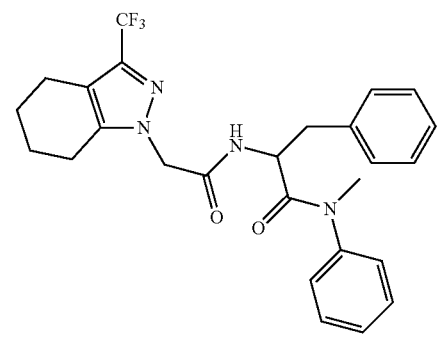 [SMILES: CN(C(=O)C(Cc1ccccc1)NC(=O)Cn1nc(C(F)(F)F)c2c1CCCC2)c1ccccc1] |
| Compound 2z | 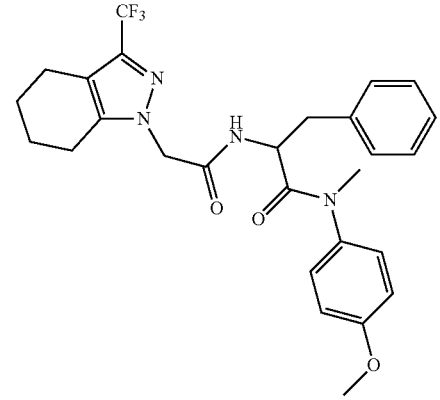 [SMILES: COc1ccc(N(C)C(=O)C(Cc2ccccc2)NC(=O)Cn2nc(C(F)(F)F)c3c2CCCC3)cc1] |

-continued
| Compound Number | Compound Structure |
|---|---|
| Compound 3z | 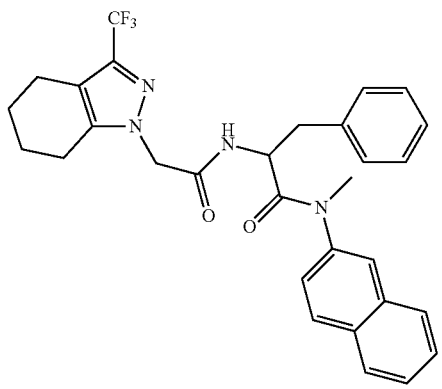 [SMILES: CN(C(=O)C(Cc1ccccc1)NC(=O)Cn1nc(C(F)(F)F)c2c1CCCC2)c1ccc2ccccc2c1] |
| Compound 4z | 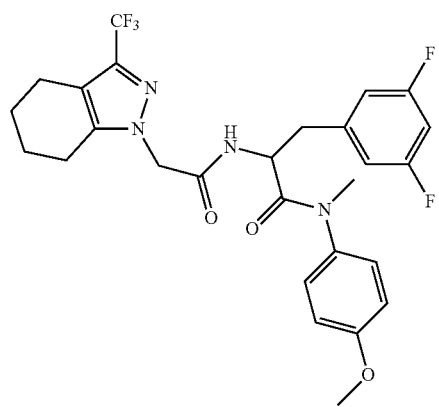 [SMILES: COc1ccc(N(C)C(=O)C(Cc2cc(F)cc(F)c2)NC(=O)Cn2nc(C(F)(F)F)c3c2CCCC3)cc1] |
| Compound 5z | 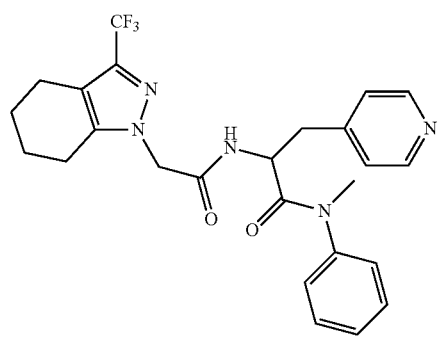 [SMILES: CN(C(=O)C(Cc1ccncc1)NC(=O)Cn1nc(C(F)(F)F)c2c1CCCC2)c1ccccc1] |
| Compound 6z | 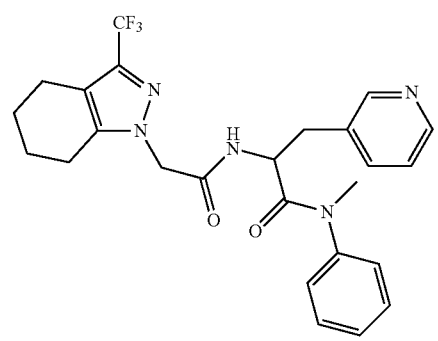 [SMILES: CN(C(=O)C(Cc1cccnc1)NC(=O)Cn1nc(C(F)(F)F)c2c1CCCC2)c1ccccc1] |

-continued
| Compound Number | Compound Structure |
|---|---|
| Compound 7z | 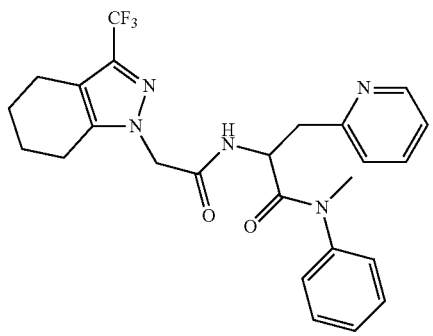 [SMILES: CN(C(=O)C(Cc1ccccn1)NC(=O)Cn1nc(C(F)(F)F)c2c1CCCC2)c1ccccc1] |
| Compound 8z | 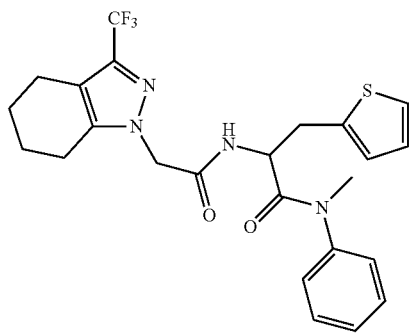 [SMILES: CN(C(=O)C(Cc1cccs1)NC(=O)Cn1nc(C(F)(F)F)c2c1CCCC2)c1ccccc1] |
| Compound 9z | 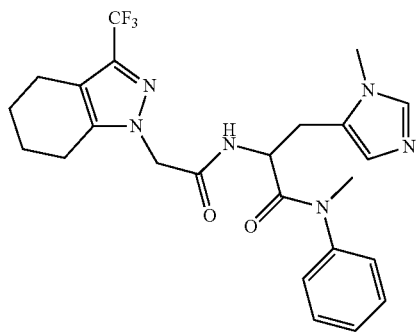 [SMILES: CN(C(=O)C(Cc1cncn1C)NC(=O)Cn1nc(C(F)(F)F)c2c1CCCC2)c1ccccc1] |
| Compound 10z | 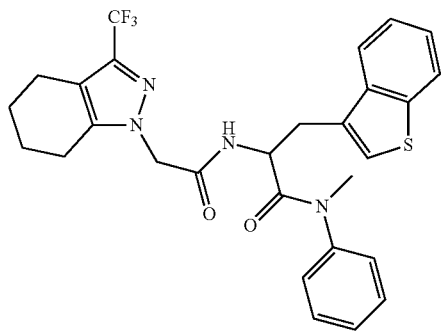 [SMILES: CN(C(=O)C(Cc1csc2ccccc12)NC(=O)Cn1nc(C(F)(F)F)c2c1CCCC2)c1ccccc1] |

| Compound Number | Compound Structure |
|---|---|
| Compound 11z | 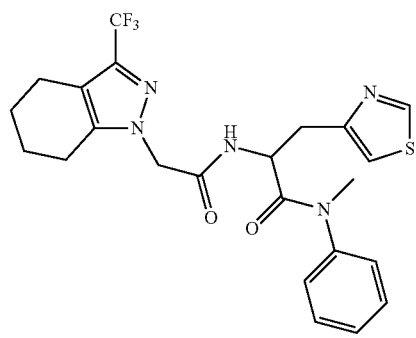 [SMILES: CN(C(=O)C(Cc1cscn1)NC(=O)Cn1nc(C(F)(F)F)c2c1CCCC2)c1ccccc1] |
| Compound 12z | 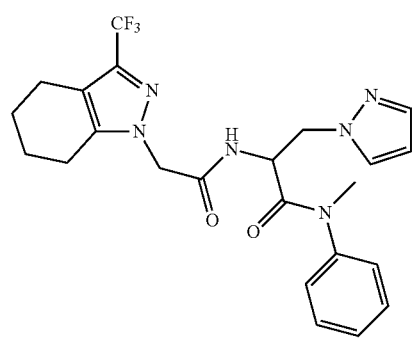 [SMILES: CN(C(=O)C(Cn1cccn1)NC(=O)Cn1nc(C(F)(F)F)c2c1CCCC2)c1ccccc1] |
| Compound 13z | 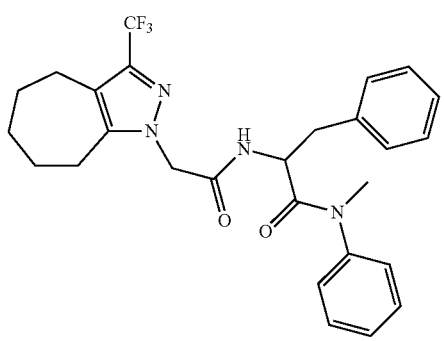 [SMILES: CN(C(=O)C(Cc1ccccc1)NC(=O)Cn1nc(C(F)(F)F)c2c1CCCCC2)c1ccccc1] |
| Compound 14z | 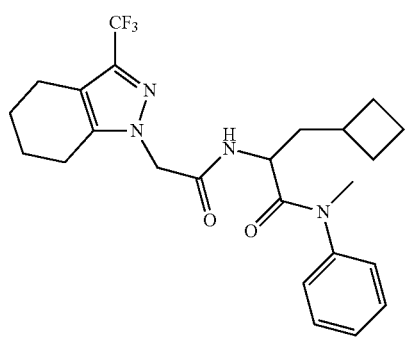 [SMILES: CN(C(=O)C(CC1CCC1)NC(=O)Cn1nc(C(F)(F)F)c2c1CCCC2)c1ccccc1] |

| Compound Number | Compound Structure |
|---|---|
| Compound 15z | 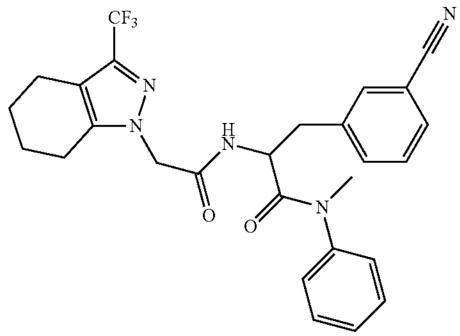 [SMILES: CN(C(=O)C(Cc1cccc(C#N)c1)NC(=O)Cn1nc(C(F)(F)F)c2c1CCCC2)c1ccccc1] |
| Compound 16z | 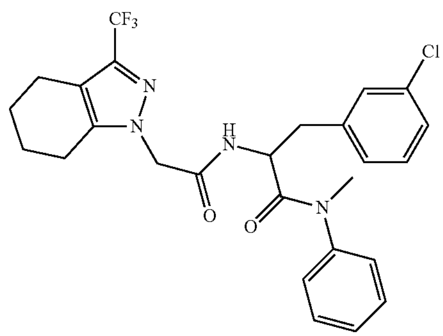 [SMILES: CN(C(=O)C(Cc1cccc(Cl)c1)NC(=O)Cn1nc(C(F)(F)F)c2c1CCCC2)c1ccccc1] |
| Compound 17z | 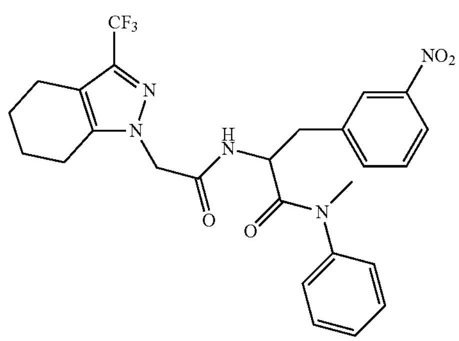 [SMILES: CN(C(=O)C(Cc1cccc([N+](=O)[O-])c1)NC(=O)Cn1nc(C(F)(F)F)c2c1CCCC2)c1ccccc1] |
| Compound 18z | 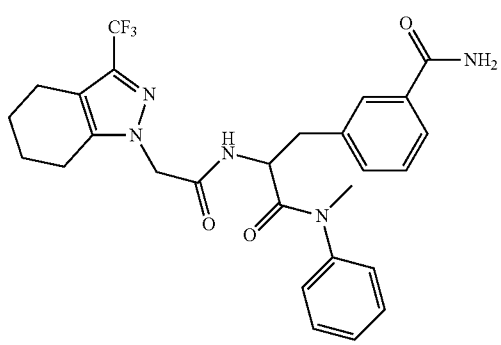 [SMILES: CN(C(=O)C(Cc1cccc(C(N)=O)c1)NC(=O)Cn1nc(C(F)(F)F)c2c1CCCC2)c1ccccc1] |

| Compound Number | Compound Structure |
|---|---|
| Compound 19z | 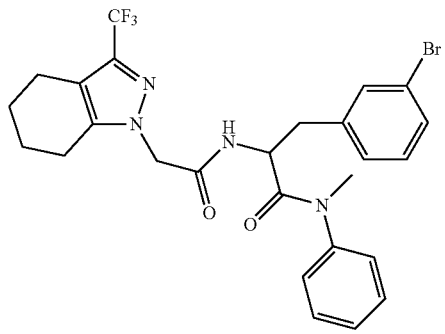 [SMILES: CN(C(=O)C(Cc1cccc(Br)c1)NC(=O)Cn1nc(C(F)(F)F)c2c1CCCC2)c1ccccc1] |
| Compound 20z | 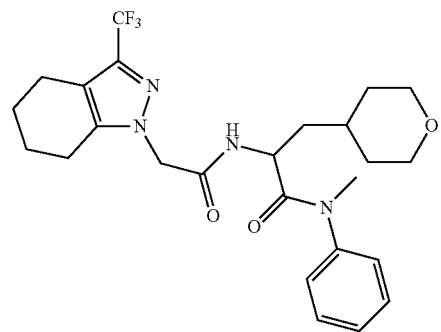 [SMILES: CN(C(=O)C(CC1CCOCC1)NC(=O)Cn1nc(C(F)(F)F)c2c1CCCC2)c1ccccc1] |
| Compound 21z | 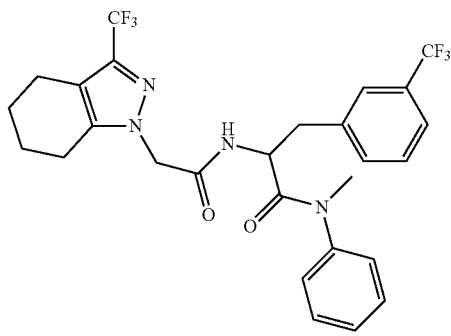 [SMILES: CN(C(=O)C(Cc1cccc(C(F)(F)F)c1)NC(=O)Cn1nc(C(F)(F)F)c2c1CCCC2)c1ccccc1] |
| Compound 22z | 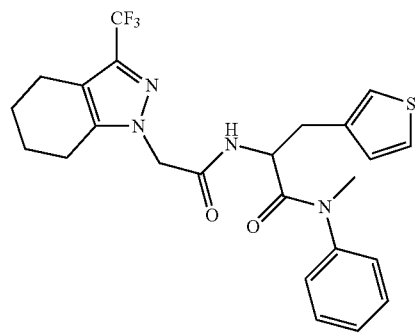 [SMILES: CN(C(=O)C(Cc1ccsc1)NC(=O)Cn1nc(C(F)(F)F)c2c1CCCC2)c1ccccc1] |

-continued

| Compound Number | Compound Structure |
|---|---|
| Compound 23z | 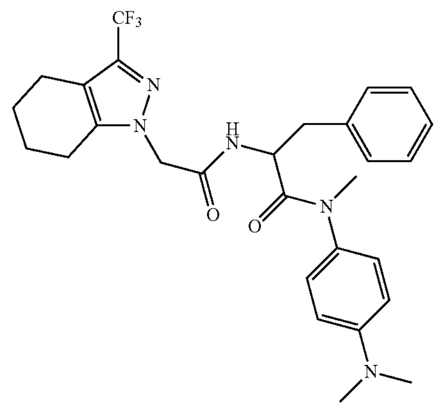 [SMILES: CN(C)c1ccc(N(C)C(=O)C(Cc2ccccc2)NC(=O)Cn2nc(C(F)(F)F)c3c2CCCC3)cc1] |
| Compound 24z | 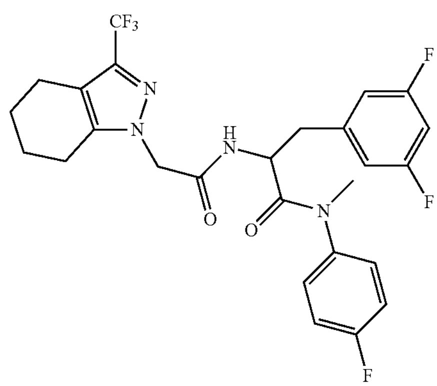 [SMILES: CN(C(=O)C(Cc1cc(F)cc(F)c1)NC(=O)Cn1nc(C(F)(F)F)c2c1CCCC2)c1ccc(F)cc1] |
| Compound 25z | 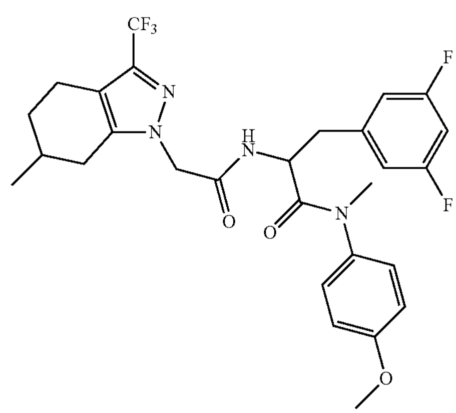 [SMILES: COc1ccc(N(C)C(=O)C(Cc2cc(F)cc(F)c2)NC(=O)Cn2nc(C(F)(F)F)c3c2CC(C)CC3)cc1] |
| Compound 26z | 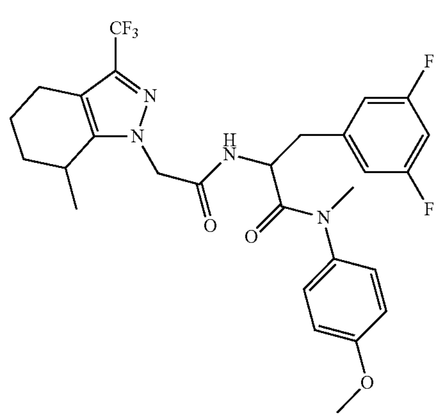 [SMILES: COc1ccc(N(C)C(=O)C(Cc2cc(F)cc(F)c2)NC(=O)Cn2nc(C(F)(F)F)c3c2C(C)CCC3)cc1] |

-continued

| Compound Number | Compound Structure |
|---|---|
| Compound 27z | 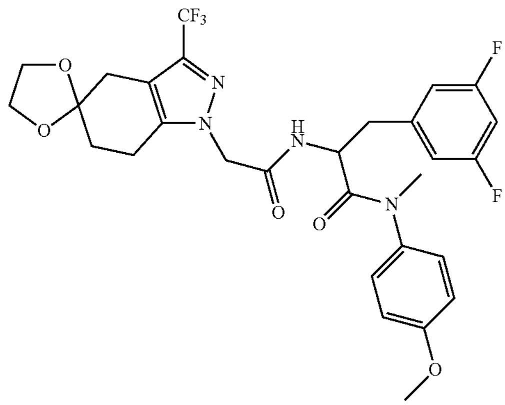 [SMILES: COc1ccc(N(C)C(=O)C(Cc2cc(F)cc(F)c2)NC(=O)Cn2nc(C(F)(F)F)c3c2CCC2(C3)OCCO2)cc1] |
| Compound 28z | 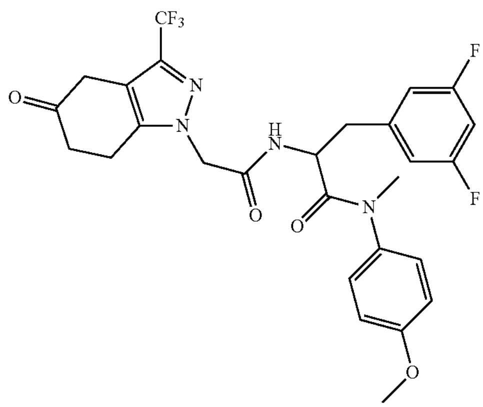 [SMILES: COc1ccc(N(C)C(=O)C(Cc2cc(F)cc(F)c2)NC(=O)Cn2nc(C(F)(F)F)c3c2CCC(=O)C3)cc1] |
| Compound 29z | 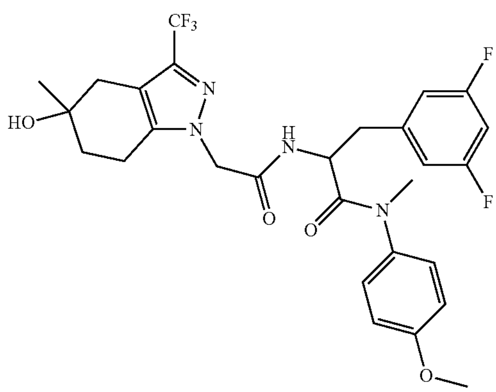 [SMILES: COc1ccc(N(C)C(=O)C(Cc2cc(F)cc(F)c2)NC(=O)Cn2nc(C(F)(F)F)c3c2CCC(C)(O)C3)cc1] |
| Compound 30z | 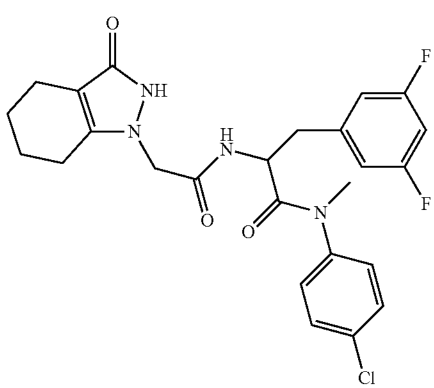 [SMILES: CN(C(=O)C(Cc1cc(F)cc(F)c1)NC(=O)Cn1[nH]c(=O)c2c1CCCC2)c1ccc(Cl)cc1] |

-continued
| Compound Number | Compound Structure |
|---|---|
| Compound 31z | 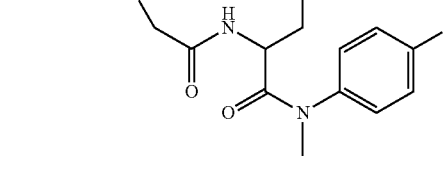 |
| Compound 32z | 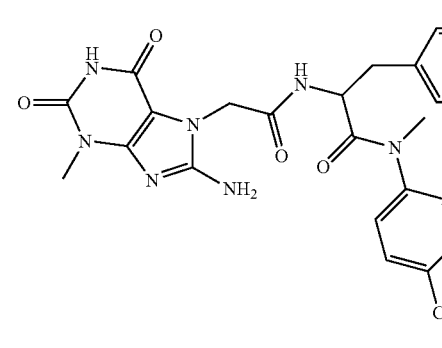 |
| Compound 33z | 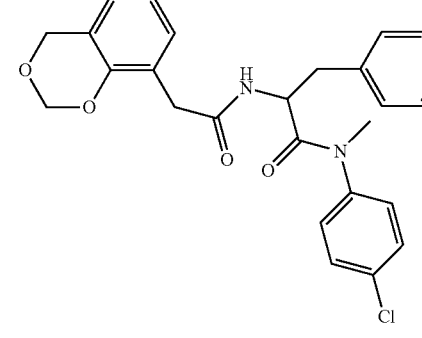 |
| Compound 34z | 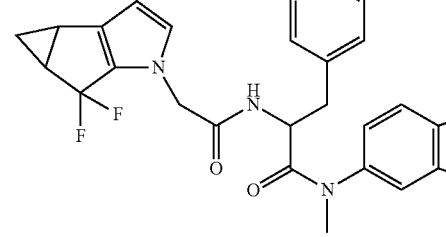 |

| Compound Number | Compound Structure |
|---|---|
| Compound 35z | 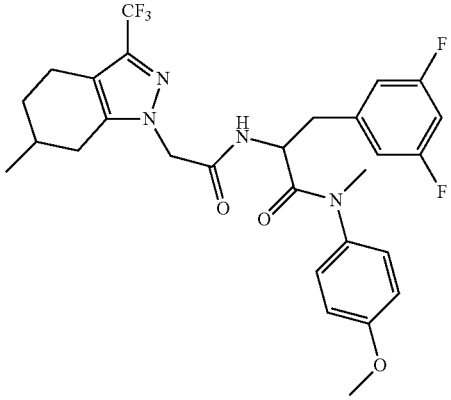 [SMILES: COc1ccc(N(C)C(=O)C(Cc2cc(F)cc(F)c2)NC(=O)Cn2nc(C(F)(F)F)c3c2CC(C)CC3)cc1] |

One skilled in the art will recognize that substituents and other moieties of the compounds of Formula (I), (Ia), or (Ib), such as Compounds 1-35 or 1z-35z, should be selected in order to provide, a compound which is sufficiently stable to provide a pharmaceutically useful compound which can be formulated into an acceptably stable pharmaceutical composition. Compounds of Formula (I), (Ia), or (Ib), such as Compounds 1-35 or 1z-35z, which have such stability are contemplated as falling within the scope of the present invention.

The compounds of Formula (I), (Ia), or (Ib), such as Compounds 1-35 or 1z-35z, may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogeuphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates chlorobenzoates methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: *The Science and Practice of Pharmacy*, 21$^{th}$ Edition, Lippincott Williams and Wilkins, Philadelphia, Pa., 2006.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

It is understood by one skilled in the art that this invention also includes any compound provided herein that may be enriched at any or all atoms above naturally occurring isotopic ratios with one or more isotopes such as, but not limited to, deuterium ($^2$H or D).

The compounds disclosed herein may contain chiral centers, which may be either of the (R) or (S) configuration, or which may comprise a mixture thereof. Accordingly, the present disclosure includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present disclosure.

The compounds of the present disclosure may be compounds according to Formula (I), (Ia), or (Ib) with one or more chiral centers, which may be either of, the (R) or (S) configuration, or which may comprise a mixture thereof. The carbon to which R$^4$ and the carbon to which —CH$_2$—R$^1$ are connected may be either of the R or S configurations. When R$^4$ is a substituent other than H, the carbon to which R$^4$ is connected is a chiral center and may be either of the R or S configuration. The carbon to which —CH$_2$—R$^1$ is connected to is a chiral center and may be either of the R or S configuration. In one variation of Formula I, R$^4$ is H and the chiral center is of the S configuration.

The present disclosure includes both racemic mixtures of a compound of Formula I and isolated isomers of Formula I. Where more than one chiral center is present in a compound of the present disclosure, some, none, or all of the chiral centers may be enantiomerically enriched. Thus, mixtures of a compound of Formula I may be racemic with respect to one or more chiral centers and/or enantiomerically enriched with respect to one or more chiral centers.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). Such formulations comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations described herein that are suitable for oral administration may be presented as discrete units including but not limited to capsules, cachets or tablets each containing a predetermined amount of the active ingredient.

Pharmaceutical formulations disclosed herein comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material), in some embodiments, a dosage form (e.g., for oral administration to humans) contains: from 10 mg to 1000 mg or from 50 mg to 1000 mg or from 100 mg to 1000 mg or from 200 mg to 1000 mg or from 300 mg to 1000 mg or from 10 mg to 800 mg or from 10 mg to 600 mg or from 10 mg to 500 mg or from 10 mg to 400 mg or from 10 mg to 300 mg or from 50 mg to 800 mg or from 100 mg to 600 mg or from 150 mg to 500 mg or from 200 mg to 400 mg or from 50 mg to 500 mg or from 10 mg to 300 mg or from 50 mg to 300 mg or from 10 mg to 200 mg or from 50 mg to 200 mg or from 100 mg to 300 mg or from 100 mg to 200 mg or from 200 mg to 300 mg of active material (e.g., a compound of any of Formula (I), (Ia), or (Ib)). In some embodiments, a dosage form for oral administration to humans contains at least any of 10, 25, 50, 100, 150, 200, 250 or 300 mg and no more than 500 or 800 or 1000 mg of active material (e.g., from at least 50 mg to no more than 500 mg). In some embodiments, a dosage form for oral administration to humans contains at least any of 10, 25, 50, 100, 150, 200, 250 or 300 mg or no more than 500 or 800 or 1000 mg of active material. In some embodiments, a dosage form for oral administration to humans contains any of 10, 25, 50, 100, 150, 200, 250, 300, 350, 400, 450, 500, 550, 600, 650, 700, 750, 800, 850, 900, 950, or 1000 mg of active material. It is understood that a dosage form in an amount provided herein may be administered to a patient (e.g., a human in need thereof) in accordance with a dosing regimen provided herein, such as once, twice or thrice daily dosing. In one aspect, a dosing regimen provides for administration of at least 10 mg and no more than 1,000 mg of active material (e.g., a compound of any of Formula (I), (Ia), or (Ib)) daily, and it is understood that the amount may be provided in any suitable dosage form and amount (e.g., 500 mg twice daily or 1,000 mg once daily would provide the same amount of 1,000 mg/day dosing). The invention embraces once daily dosing to an individual (e.g., a human in need thereof) of a dosage form of compound (e.g., a compound of any of Formula (I), (Ia), or (Ib)) containing at least 50 mg and not more than 300 mg of compound. In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

In certain embodiments, a formulation comprising an active ingredient provided herein (a compound of any one of Formula (I), (Ia), or (Ib), such as any one of Compounds 1-35 or 1z-35z or a pharmaceutical salt thereof) in one variation does not contain an agent that affects the rate at which the active ingredient is metabolized. Thus, it is understood that compositions comprising a compound of any one of Formula (I), (Ia), or (Ib) in one aspect do not comprise an agent that would affect (e.g., slow, hinder or retard) the metabolism of a compound of any one of Formula (I), (Ia), or (Ib) or any other active ingredient administered separately, sequentially or simultaneously with a compound of any one of Formula (I), (Ia), or (Ib). It is also understood that any of the methods, kits, articles of manufacture and the like detailed herein in one aspect do not comprise an agent that would affect (e.g., slow, hinder or retard) the metabolism of a compound of any one of Formula (I), (Ia), or (Ib) or any other active ingredient administered separately, sequentially or simultaneously with a compound of any one of Formula (I), (Ia), or (Ib).

In certain embodiments, a compound of any one of Formula (I), (Ia), or (Ib), such as any one of Compounds 1-35 or 1z-35z, is formulated as a tablet, which may optionally contain one or more other compounds useful for treating HIV. In certain instances, the tablet can contain another active ingredient for treating HIV, such as an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor, and combinations thereof. In one variation, such tablets are suitable for once daily dosing.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Methods of Use

Provided herein is a method of inhibiting the proliferation of the HIV virus in an individual in need thereof, comprising administering a compound of any of Formula (I), (Ia), (Ib) or (II), or a pharmaceutically acceptable salt thereof, to the individual. Also provided herein is a compound of any of Formula (I), (Ia), (Ib), or (II), or a pharmaceutically acceptable salt thereof, for use in such a method. In one aspect, the individual in need thereof is a human who has been infected with HIV. In one variation, the individual in need thereof is a human who has been infected with HIV but who has not developed AIDS. In one variation, the individual in need thereof is an individual at risk for developing AIDS. In another variation, the individual in need thereof is a human who has been infected with HIV and who has developed AIDS. In one aspect of the methods provided herein, a compound of any of Formula (I), (Ia), (Ib), or (II), or a pharmaceutically acceptable salt thereof, is administered to the individual separately, sequentially or simultaneously with another active ingredient for treating HIV, such as an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

One embodiment provides a method for treating a Retroviridae viral infection (e.g., an HIV viral infection) in an individual (e.g., a human), comprising administering a compound of any of Formula (I), (Ia), (Ib), or (II), or a pharmaceutically acceptable salt thereof, to the individual.

One embodiment provides a method for inhibiting the proliferation of the HIV virus, treating AIDS or delaying the onset of AIDS in an individual (e.g., a human), comprising administering a compound of any of Formula (I), (Ia), (Ib), or (II), or a pharmaceutically acceptable salt thereof, to the individual.

One embodiment provides a method for treating an HIV infection in an individual (e.g., a human), comprising administering a compound of any of Formula (I), (Ia), (Ib), or (II), or a pharmaceutically acceptable salt thereof; to the individual.

One embodiment provides a method for treating an HIV infection in an individual (e.g., a human), comprising administering to the individual in need thereof a therapeutically effective amount of a compound of any of Formula (I), (Ia), (Ib), or (II), or a pharmaceutically acceptable salt thereof, in combination with a therapeutically effective amount of an additional therapeutic agent, wherein the therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof. Also provided herein is a compound of any of Formula (I), (Ia), (Ib), or (II), or a pharmaceutically acceptable salt thereof; for use in such a method.

One embodiment provides a compound of any of Formula (I), (Ia), (Ib), or (II), or a pharmaceutically acceptable salt thereof for use in medical therapy (e.g., for use in treating a Retroviridae viral infection (e.g., an HIV viral infection) or the proliferation of the HIV virus or AIDS or delaying the onset of AIDS in an individual (e.g., a human)).

One embodiment provides a compound of any of Formula (I), (Ia), (Ib), or (II), or a pharmaceutically acceptable salt thereof for use in the manufacture of a medicament for treating a Retroviridae viral infection (e.g., an HIV viral infection) or the proliferation of the HIV virus or AIDS or delaying the onset of AIDS in an individual (e.g., a human).

One embodiment provides a compound of any of Formula (I), (Ia), (Ib), or (II), or a pharmaceutically acceptable salt thereof, for use in the prophylactic or therapeutic treatment of the proliferation of a Retroviridae virus, an HIV virus or AIDS or for use in the therapeutic treatment of delaying the onset of AIDS.

One embodiment provides the use of a compound of any of Formula (I), (Ia), (Ib), or (II), or a pharmaceutically acceptable salt thereof, for the manufacture of a medicament for a Retroviridae virus infection (e.g., an HIV virus infection) in an individual (e.g., a human). One embodiment provides a compound of any of Formula (I), (Ia), (Ib), or (II), or a pharmaceutically acceptable salt thereof, for use in the prophylactic or therapeutic treatment of a Retroviridae virus infection (e.g., an HIV virus infection).

In some embodiments, in the methods of use, the administration is to an individual (e.g., a human) in need of the treatment. In some embodiments, in the methods of use, the administration is to an individual (e.g., a human) who is at risk of developing AIDS.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds disclosed herein is that they are orally bioavailable and can be dosed orally.

Dosing Regimen

The compound, such as a compound of any of Formula (I), (Ia), (Ib), or (II), may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of any of Formula (I), (Ia), (Ib), or (II) may be adjusted over the course of the treatment, e.g., based on the judgment of the administering physician.

The compound may be administered to an individual in an effective amount. In one aspect, the compound is administered once daily. In one aspect, the compound is administered twice a day. In one aspect, the compound is administered three times daily. It is understood that the compound may be administered in any dosage amount provided herein, such as a dosage amount that would provide at least 10 mg/day dosing and no more than 1,000 mg/day dosing. Once daily oral dosing is embraced, such as by administering a dosage form containing from 50 mg to 300 mg of compound.

Combination Therapy

In one embodiment, the invention provides a method for treating an HIV infection, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection. Also provided herein is a compound disclosed herein, or a pharmaceutically acceptable salt thereof, for use in such a method.

A compound as disclosed herein (e.g., a compound of any of Formula (I), (Ia), (Ib), or (II) or a pharmaceutically acceptable salt thereof) may be combined with one or more additional therapeutic agents in any dosage amount of the compound (e.g., from 50 mg to 300 mg of compound).

In one embodiment, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more additional therapeutic agents. Also provided herein is a compound disclosed herein, or a pharmaceutically acceptable salt thereof, for use in such a method.

In one embodiment, the invention provides pharmaceutical compositions comprising a compound disclosed herein, or a pharmaceutically acceptable salt thereof, in combination with at least one additional therapeutic agent, and a pharmaceutically acceptable carrier. For example, the therapeutic agent used in combination with the compound disclosed herein can be any anti-HIV agent.

In one embodiment, combination pharmaceutical agents comprising a compound disclosed herein, or a pharmaceutically acceptable salt thereof, in combination with one or more additional therapeutic agents are provided.

One embodiment provides pharmaceutical compositions comprising a compound disclosed herein, or a pharmaceutically acceptable salt thereof, in combination with at least one additional therapeutic agent, and a pharmaceutically acceptable carrier. In one embodiment, the additional therapeutic agent may be an anti-HIV agent. For example, in some embodiments, the additional therapeutic agent is selected from the group consisting of HIV protease inhibiting compounds (HIV protease inhibitors), HIV non-nucleoside inhibitors of reverse transcriptase, HIV nucleoside inhibitors of reverse transcriptase, HIV nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, capsid polymerization inhibitors or capsid disrupting compounds such as those disclosed in US 2013/0165489 (University of Pennsylvania), and WO 2013/006792 (Pharma Resources), pharmacokinetic enhancers, and other drug for treating HIV, and combinations thereof.

One embodiment provides a pharmaceutical composition comprising a compound disclosed herein; and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DFC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene BILR 355 BS, VRX 840773, lersivirine (UK-453061), RDEA806, KM023 and MK-1439;

(3) HIV nucleoside inhibitors of reverse transeriptase selected from the group consisting of zidovudine, emtricitabine didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, GS-9131 (Gilead Sciences) and fosalvudine tidoxil (formerly HDP 99.0003);

(4) HIV nucleotide inhibitors of reverse transcriptase selected from the group consisting of tenofovir, tenofovir disoproxil fumarate, tenofovir disoproxil hemifumarate, tenofovir disoproxil, tenofovir alafemunide fumarate, tenofovir alafenamide hemifumarate, tenofovir alafenamide, GS-7340 (Gilead Sciences), GS-9148 (Gilead Sciences), adefovir, adefovir dipivoxil, CMX-001 (Chimerix) and CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by reference in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of cobicistat, ritonavir, and SPI-452; and

(15) other drugs for treating HIV selected from the group consisting of BAS-100, SPI-452, REP 9, SP-01A, MX-355, DES6, ODN-93, ODN-112, VGV-1, PA-457 (bevirimat), HRG214, VGX-410, KD-247, AMZ 0026, CYT 99007A-221 DEBIO-025, BAY 50-4798, MDX010 (ipilimumab), PBS 119, ALG 889, and PA-1050040 (PA-040).

In certain embodiments, a compound disclosed herein, or a pharmaceutically acceptable salt thereof, is combined with two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleotide inhibitor of reverse transcriptase, and an HIV protease inhibiting compound. In a further embodiment, a compound disclosed herein, or a pharmaceutically acceptable salt thereof, is combined with an HIV nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleotide inhibitor of reverse transcriptase, an HIV non-nucleoside inhibitor of reverse transcriptase, and a pharmacokinetic enhancer.

In a specific embodiment, a compound disclosed herein, or a pharmaceutically acceptable salt thereof, is combined with tenofovir, tenofovir disoproxil fumarate, tenofovir disoproxil hemifumarate, tenofovir disoproxil, tenofovir alafenamide fumarate, tenofovir alafenamide hemifumarate, or tenofovir alafenamide. In another specific embodiment, a compound disclosed herein, or a pharmaceutically acceptable salt thereof, is combined with tenofovir disoproxil fumarate, tenofovir disoproxil hemifumarate, or tenofovir alafenamide. In a specific embodiment, a compound disclosed herein, or a pharmaceutically acceptable salt thereof, is combined with emtricitabine, abacavir or lamivudine.

In a specific embodiment, a compound disclosed herein, or a pharmaceutically acceptable salt thereof, is combined with one of tenofovir, tenofovir disoproxil fumarate, tenofovir disoproxil hemifumarate, tenofovir disoproxil, tenofovir alafenamide fumarate, tenofovir alafenamide hemifumarate, or tenofovir alafenamide and one of emtricitabine, abacavir or lamivudine. In a specific embodiment, a compound disclosed herein, or a pharmaceutically acceptable salt thereof, is combined with one of tenofovir disoproxil fumarate, tenofovir disoproxil hemifumarate, tenofovir alafenamide fumarate, or tenofovir alafenamide and one of emtricitabine or abacavir.

In some embodiments, a compound disclosed herein, or a pharmaceutically acceptable salt thereof, is combined with 5-30 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 10 mg tenofovir alafenamide fumarate, tenofovir alafenamide hemifumarate, or tenofovir alafenamide and 200 mg emtricitabine. In some embodiments, a compound disclosed herein, or a pharmaceutically acceptable salt thereof, is combined with 25 mg tenofovir alafenamide fumarate, tenofovir alafenamide hemifumarate, or tenofovir alafenamide and 200 mg emtricitabine. A compound as disclosed herein (e.g., a compound of any of Formula (I), (Ia), (Ib), or (II) or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, a compound disclosed herein, or a pharmaceutically acceptable salt thereof, is combined with 200-400 mg tenofovir disoproxil fumarate, tenofovir disoproxil hemifumarate, or tenofovir disoproxil and 200 mg emtricitabine. In some embodiments, a compound disclosed herein, or a pharmaceutically acceptable salt thereof, is combined with 200-250; 200-300; 200-350; 250-350; 250-400; 350-400; 300-400; or 250-400 mg tenofovir disoproxil fumarate, tenofovir disoproxil hemifumarate, or tenofovir disoproxil and 200 mg emtricitabine. In some embodiments, a compound disclosed herein, or a pharmaceutically acceptable salt thereof, is combined with 300 mg tenofovir disoproxil fumarate, tenofovir disoproxil hemifumarate, or tenofovir disoproxil and 200 mg emtricitabine. A compound as disclosed herein (e.g., a compound of any of Formula (I), (Ia), (Ib), or (II) or a pharmaceutically acceptable salt thereof) may be combined with the agents provided herein in any dosage amount of the compound (e.g., from 50 mg to 300 mg of compound) the same as if each combination of dosages were specifically and individually listed.

In some embodiments, one or more of the compounds disclosed herein are combined with one or more other active therapeutic agents in a unitary dosage form for simultaneous or sequential administration to a patient. In certain embodiments, a pharmaceutical composition including one or more of the compounds disclosed herein combined with one or more other active therapeutic agents is provided. In certain embodiments, the compounds disclosed herein are combined with one or more other active therapeutic agents in a solid dosage form. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of disclosed herein and one or more other active therapeutic agents are both present in the body of the patient.

In yet another embodiment, the present application provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents such as those disclosed above. Also provided is a compound disclosed herein, or a pharmaceutically acceptable salt thereof, in combination with one or more additional therapeutic agents such as those disclosed above, for use in treating an HIV infection. The invention also provides a product comprising a compound disclosed herein, or a pharmaceutically acceptable salt or co-crystal thereof, and an additional therapeutic agent such as those disclosed above as a combined preparation for simultaneous, separate or sequential use in therapy (e.g., in treating an HIV infection).

Kits and Articles of Manufacture

The present disclosure provides a kit comprising a compound of any of Formula (I), (In), (Ib), or (II), or a pharmaceutically acceptable salt thereof. The kit may further comprise instructions for use, e.g., for use in inhibiting an HIV protease, such as for use in treating an HIV infection or AIDS. The instructions for use are generally written instructions, although electronic storage media (e.g., magnetic diskette or optical disk) containing instructions are also acceptable.

The present disclosure also provides a pharmaceutical kit comprising one or more containers comprising a compound of any of Formula (I), (Ia), (Ib), or (II), or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also provided are articles of manufacture comprising a unit dosage of a compound of any of Formula (I), (Ia), (Ib), or (II), or a pharmaceutically acceptable salt thereof; in suitable packaging for use in the methods described herein. Suitable packaging is known in the art and includes, for example, vials, vessels, ampules, bottles, jars, flexible packaging and the like. An article of manufacture may further be sterilized and/or sealed.

General Synthetic Procedures

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, $2^{nd}$ ed., ed. L. R. Snyder and J. J. Kirkland, John Wiley and Sons, 1979; and Thin Layer Chromatography, E. Stahl (ed.), Springer-Verlag, New York, 1969.

Although some schemes below may illustrate a certain stereochemistry, it is understood that the schemes and methods are applicable to compounds of the general structure provided, and are not limited to the compounds with the stereochemistry as shown.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, as suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I), (Ia), (Ib), or (II).

Representative syntheses of compounds of the present disclosure are described in schemes below, and the particular examples that follow.

Scheme 1 shows a representative synthesis of the compounds of the embodiments.

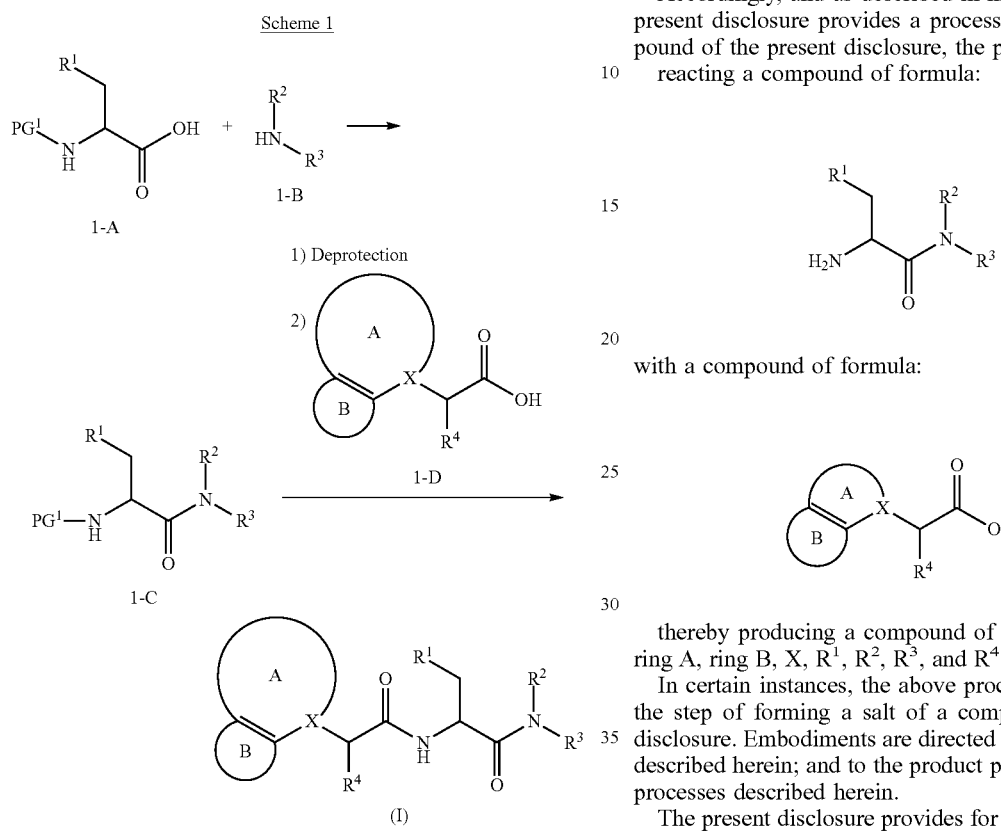

In Scheme 1, ring A, ring B, X, R¹, R², R³, and R⁴ are as defined herein. As discussed below, PG¹ is an amino protecting group. Starting materials may be obtained from commercial sources or via well-established synthetic procedures.

With continued reference to Scheme 1, the carboxyl group of Compound 1-A can react with the amino group of Compound 1-B through standard coupling conditions to produce Compound 1-C. In certain instances, the carboxyl group of Compound 1-A can be activated to facilitate reaction with an amine. Activating agents for carboxyl groups include, but are not limited to, various phosphorus compounds, carbodiimides, and chloroformates. In certain instances, an activating agent for a carboxyl group is isobutyl chloroformate.

Compound 1-C is then protected to remove the amino protecting group PG¹. In some instances, the protecting group PG¹ is a Boc-group, which can be removed with TFA. Other examples of suitable protecting groups for amino groups and the procedure for removal of the protecting group can be found in T. W. Greene and P. G. M. Wuts, "Protective Groups in Organic Synthesis," 4$^{th}$ ed., Wiley, New York 2006.

Upon removal of the protecting group, the amino group of Compound 1-C can react with the carboxyl group of Compound 1-C through standard peptide coupling conditions to produce a compound of Formula (I). Reagents such as EDCI/HOBt, HOBt, PyBOP, HATU, or BEM (Carpino, L. A. J. Am. Chem. Soc. 1993, 115, 4397. Camino, L. A.; El-Faham, A. J. Am. Chem. Soc. 1995, 117, 5401. Li, P.; Xu, J. C, J. Pept. Res. 2001, 58, 129.) in the presence of a base such as DIEA or other bases familiar to one skilled in the art and in an appropriate solvent can be used.

Accordingly, and as described in more detail herein, the present disclosure provides a process of preparing a compound of the present disclosure, the process involving:

reacting a compound of formula:

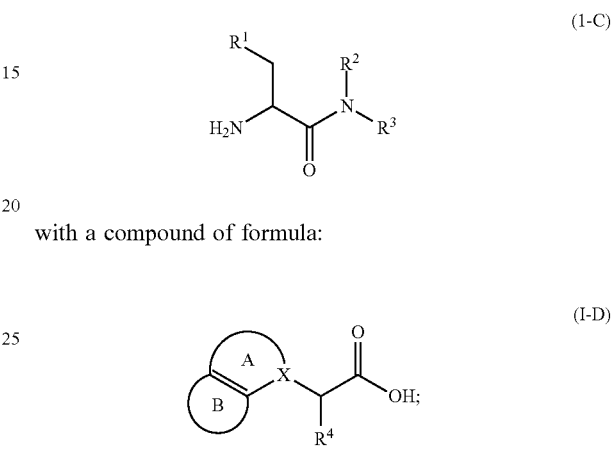

with a compound of formula:

thereby producing a compound of Formula (I), wherein ring A, ring B, X, R¹, R², R³, and R⁴ are described herein.

In certain instances, the above processes further involve the step of forming a salt of a compound of the present disclosure. Embodiments are directed to the other processes described herein; and to the product prepared by any of the processes described herein.

The present disclosure provides for intermediates used to make a compound of the Formula (I), (Ia), (Ib), or (II). The intermediates are contemplated as falling within the scope of the present invention.

Except as otherwise noted, the methods and techniques of the present embodiments are generally performed according to conventional methods well known in the art and as described in various general and more specific references that are cited and discussed throughout the present specification. See, e.g., London, Organic Chemistry, 5$^{th}$ edition, New York: Oxford University Press, 2009; Smith, March's Advanced Organic Chemistry: Reactions, Mechanisms, and Structure, 7$^{th}$ edition, Wiley-Interscience, 2013.

EXAMPLES

The following examples are offered to illustrate but not to limit the invention. Although the examples herein may show certain stereoisomers, a skilled artisan can adapt the disclosed methods to prepare racemic mixtures and other stereoisomers.

The following abbreviations may be used throughout the specification, and have the following meanings:

° C.=degrees Celsius
Å=Angstrom
Ac=acetyl
AcOH=acetic acid
aq=aqueous
Ar=argon
atm=atmosphere BEP=2-bromo-1-ethyl pyridinium tetrafluoroborate
Bn=benzyl
Boc=tert-butoxy carbonyl
Boc₂O=di-tert-butyl dicarbonate
bp=boiling point
Bs=4-bromopbenylsulfonyl
Bu=butyl
calcd=calculated
CBS-Corey-Bakshi-Shibata
CDI-1,1'-carbonyldiimidazole
COMU=1-cyano-2-ethoxy-2-oxoethylidenaminooxy)dimethylamino-morpholino-carbenium hexafluorophosphate
DABCO=1,4-diazabicyclo[2.2.2]octane
DBU=1,8-diazabicycloundec-7-ene
DCE=1,2-dichloroethane
DCM=dichloromethane
DIAD=diisopropyl azodicarboxylate
dioxane=1,4-dioxane
DIPEA=N,N-diisopropyl-N-ethylamine
DMF=N,N-dimethylformamide
DMAP=4-dimethylaminopyridine
DMPU=1,3-dimethyl-3,4,5,6-tetrahydro-2(1H)-pyrimidinone
DMSO=dimethyl sulfoxide
dppf=1,1'-bis(diphenylphosphino)ferrocene
DSC=N,N'-disuccinimidyl carbonate
EC₅₀=half maximal effective concentration
EDC=1-ethyl-3-(3-dimetlaylaminopropyl) carbodiimide
Et=ethyl
Et₂O=diethyl ether
EtOAc=ethyl acetate
EtOH=ethanol
equiv=equivalent
F-NMR=fluorine nuclear magnetic resonance spectroscopy
g=gram
h=hour
HATU=O-(7-azabenzotriazol-1-yl)-N,N,N',N'-tetramethyluronium hexafluorophosphate
HCV=hepatitis C virus
Hex=hex=hexanes
HMDS=hexamethyldisilazane(azide)
HMPA=hexamethylphosphoramide
¹H-NMR=proton nuclear magnetic resonance spectroscopy
HOAc=acetic acid
HPLC=high pressure liquid chromatography
L=liter
LCMS-ESI⁺=liquid chromatography mass spectrometer (electrospray ionization)
M=molar concentration (mol/L)
Me=methyl
MeCN=acetonitrile
MeOH=methanol
MeTHF=2-methyltetrahydrofuran
mg=milligram
MHz=mega Hertz
mL=milliliter
mmol=millimole
min=minute
MTBE=methyl tert-butyl ether
Ms=methanesulfonyl
MsCl=methanesulfonyl chloride
MS=molecular sieves
n=normal
N=normal concentration
NMO=N-methylmorpholine-N-oxide
NMP=N-methylpyrrolidinone
o/n=overnight
Pf=9-phenyl-9H-fluoren-9-yl
PPh₃=triphenylphosphine
PE=petroleum ether
Ph=phenyl
PhMe=toluene
pM=picomolar
rt=room temperature
sat=sat.=saturated
sec=secondary
$S_N1$=nucleophilic substitution unimolecular
$S_N2$=nucleophilic substitution bimolecular
$S_NAr$=nucleophilic substitution aromatic
t=tert=tertiary
TBAF=tetra-n-butylammonium fluoride
TBTU=O-(benzotriazol-1-yl)-N,N,N',N'-tetramethyluronium tetrafluoroborate
TEA=triethylamine
temp=temperature
Tf=trifluoromethanesulfonyl
TFA=trifluoroacetic acid
THF=tetrahydrofuran
TLC=thin layer chromatography
TMS=trimethylsilyl
TMSOTf=trimethylsilyltrifluoromethanesulfonate
TPAP=tetrapropylammonium perruthenate
Tr=triphenylmethyl
Ts=para-toluenesulfonyl
w/w=weight/weight ratio Example 1

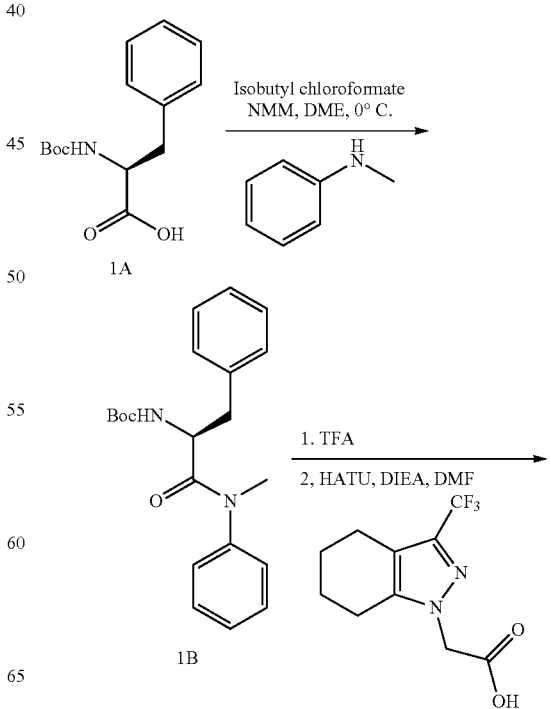

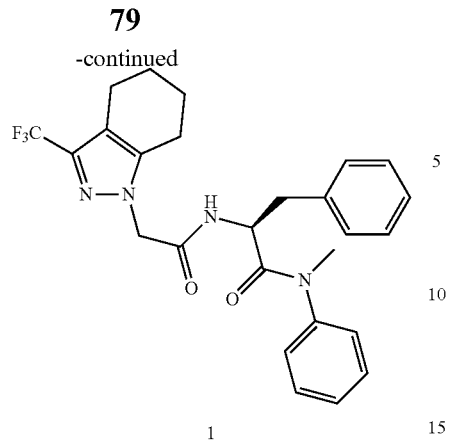

1

Synthesis of (S)-tert-butyl (1-(methyl(phenyl) amino)-1-oxo-3-phenylpropan-2-yl)carbamate (1B)

To a solution of (S)-2-((tert-butoxycarbonyl)amino)-3-phenylpropanoic acid (1 g, 3.58 mmol) and 4-methylmorpholine (0.43 mL, 3.58 mmol) in DME (1.5 mL) at 0° C., isobutyl chloroformate (0.49 mL, 3.58 mmol) was added to the solution slowly. After 30 minutes, N-methylaniline (422 mg, 3.94 mmol) was added to the mixture. The reaction mixture was stirred for 2 hours. The reaction mixture was diluted with EtOAc (100 mL) and washed with water (50 mL) and brine (50 mL). The organic layer was separated and was concentrated to dryness in vacuo. The residue was purified by flash column chromatography (Rf: 0.3, 20% EtOAc/Hexanes) to afford 1.1 g of title compound. MS (m/z) 355 [M+H]$^+$.

Synthesis of (S)—N-methyl-N,3-diphenyl-2-(2-(3-(trifluoromethyl)-4,5,6,7-tetrahydro-1H-indazol-1-yl)acetamido)propanamide (1)

To a solution of 1B (36 mg, 0.1 mmol) in TFA (1 mL), was stirred for 1 hour. The solvent was removed and concentrated to dryness in vacuo. To a solution of 2-(3-(trifluoromethyl)-4,5,6,7-tetrahydro-1H-indazol-1-yl)acetic acid (50 mg, 0.2 mmol), diisopropylethylamine (0.05 mL, 0.5 mmol) and HATU (82 mg, 2 mmol) in DMF (1 mL), the TFA salt of product from previous step was added to the solution after 10 minutes. The reaction mixture was stirred at room temperature for 1 hour. Purified reaction mixture on prep reverse phase HPLC using 20-80% B over 20 min. (A=0.1% TFA/H2O; B=0.1% TFA/Acetonitrile). Combined pure fractions as determined by LC/MS and lyophilized to provide 26 mg of desired compound. MS (m/z) 485 [M+H]$^+$.

Example 2

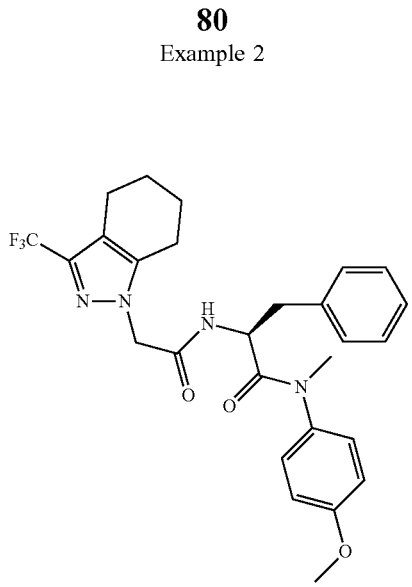

2

Synthesis of (S)—N-(4-methoxyphenyl-N-methyl-3-phenyl-2-(2-(3-(trifluoromethyl)-4,5,6,7-tetrahydro-1H-1-indazol-1-yl)acetamido)propanamide (2)

Compound 2 was prepared according to the method presented for the synthesis of Example 1 utilizing 1A and substituting 4-methoxy-N-methylaniline for N-methylaniline to provide 14 mg of title compound. MS (m/z) 515 [M+H]$^+$.

Example 3

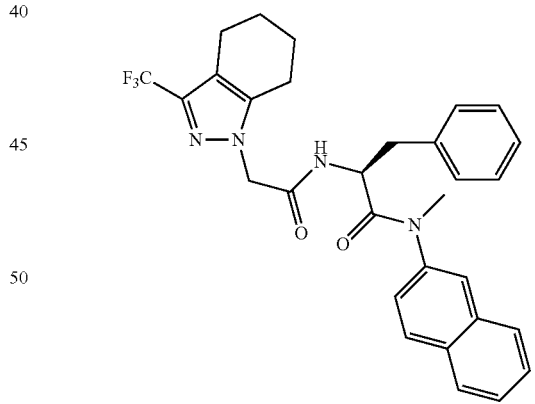

3

Synthesis of (S)—N-methyl-N-(naphthalen-2-yl)-3-phenyl-2-(2-(3-(trifluoromethyl)-4,5,6,7-tetrahydro-1H-indazol-1-yl)acetamido)propanamide (3)

Compound 3 was prepared according to the method presented for the synthesis of Example 1 utilizing 1A and substituting N-methylnaphthalen-2-amine for N-methylaniline to provide 9 mg of title compound. MS (m/z) 535 [M+H]$^+$.

Example 4

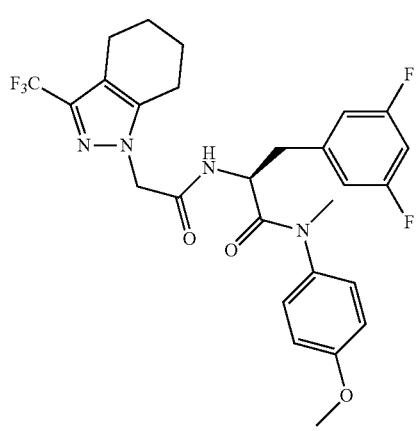

Synthesis of (S)-3-(3,5-difluorophenyl)-N-(4-methoxyphenyl)-N-methyl-2-(2-(3-(trifluoromethyl)-4,5,6,7-tetrahydro-1H-indazol-1-yl)acetamido)propanamide (4)

Compound 4 was prepared according to the method presented for the synthesis of Example 1 utilizing (S)-2-((tert-butoxycarbonyl)amino)-3-(3,5-difluorophenyl)propanoic acid for 1A and substituting 4-methoxy-N-methylaniline for N-methylaniline to provide 7 mg of title compound. MS (m/z) 551 [M+H]$^+$.

Example 5

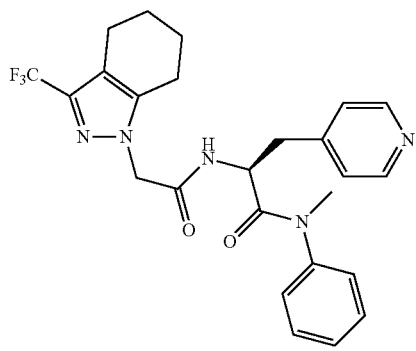

Synthesis of (S)—N-methyl-N-phenyl-3-(pyridin-4-yl)-2-(2-(3-(trifluoromethyl-4,5,6,7-tetrahydro-1H-indazol-1-yl)acetamido)propanamide (5)

Compound 5 was prepared according to the method presented for the synthesis of Example 1 utilizing (S)-2-((tert-butoxycarbonyl)amino)-3-(pyridin-4-yl)propanoic acid for 1A to provide 34 mg of title compound. MS (m/z) 486 [M+H]$^+$.

Example 6

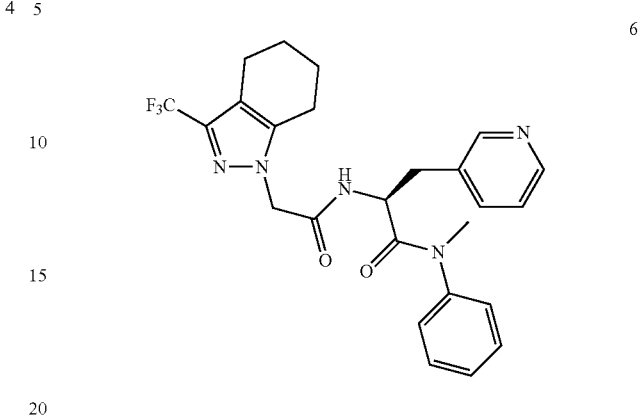

Synthesis of (S)—N-methyl-N-phenyl-3-(pyridin-3-yl)-2-(2-(3-(trifluoromethyl)-4,5,6,7-tetrahydro-1H-indazol-1-yl)acetamido)propanamide (6)

Compound 6 was prepared according to the method presented for the synthesis of Example 1 utilizing (S)-2-((tert-butoxycarbonyl)amino)-3-(pyridin-3-yl)propanoic acid for 1A to provide 34 mg of title compound. MS (m/z) 486 [M+H]$^+$.

Example 7

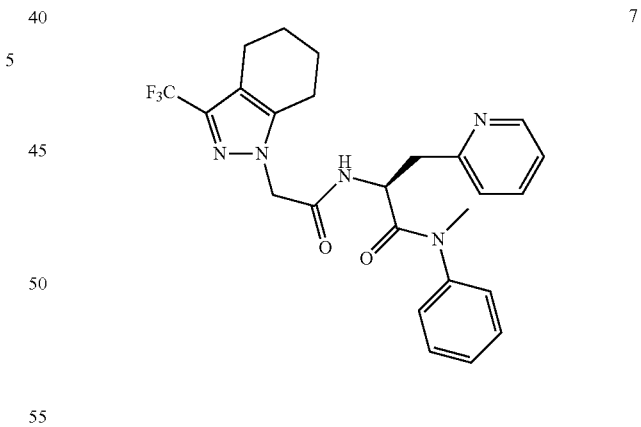

Synthesis of (S)—N-methyl-N-phenyl-3-(pyridin-2-yl)-2-(2-(3-(trifluoromethyl)-4,5,6,7-tetrahydro-1H-indazol-1-acetamido)propanamide (7)

Compound 7 was prepared according to the method presented for the synthesis of Example 1 utilizing (S)-2-((tert-butoxycarbonyl)amino)-3-(pyridin-2-yl)propanoic acid for 1A to provide 31 mg of title compound. MS (m/z) 486 [M+H]$^+$.

Example 8

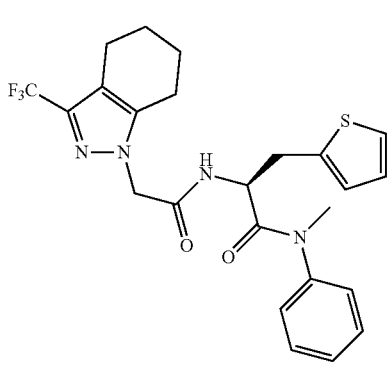

Synthesis of (S)—N-methyl-N-phenyl-3-(thiophen-2-yl)-2-(2-(3-trifluoromethyl)-4,5,6,7-tetrahydro-1H-indazol-1-yl)acetamido)propanamide (8)

Compound 8 was prepared according to the method presented for the synthesis of Example 1 utilizing (S)-2-((tert-butoxycarbonyl)amino)-3-(thiophen-2-yl)propanoic acid for 1A to provide 23 mg of title compound. MS (m/z) 491 [M+H]$^+$.

Example 9

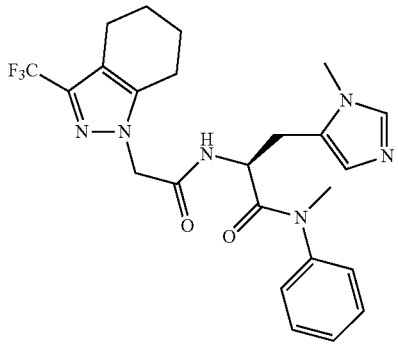

Synthesis of (S)—N-methyl-3-(1-methyl-1H-imidazol-5-yl)-N-phenyl-2-(2-(3-(trifluoromethyl)-4,5,6,7-tetrahydro-1H-1-indazol-1-yl)acetamido)propanamide (9)

Compound 9 was prepared according to the method presented for the synthesis of Example 1 utilizing (S)-2-((tert-butoxycarbonyl)amino)-3-(1-methyl-1H-imidazol-5-yl)propanoic acid for 1A to provide 9 mg of title compound. MS (m/z) 489 [M+H]$^+$.

Example 10

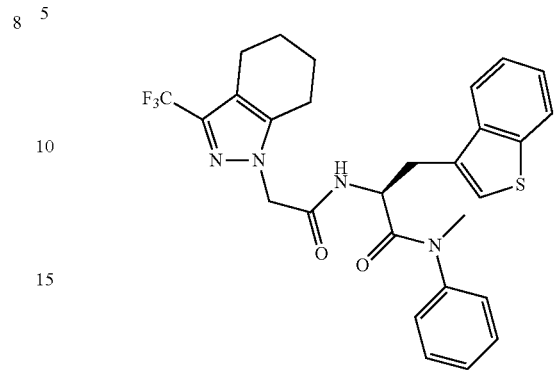

Synthesis of (S)-3-(benzo[b]thiophen-3-yl)-N-methyl-N-phenyl-2-(2-(3-(trifluoromethyl)-4,5,6,7-tetrahydro-1H-indazol-1-yl)acetamido)propanamide (10)

Compound 10 was prepared according to the method presented for the synthesis of Example 1 utilizing (S)-3-(benzo[b]thiophen-3-yl)-2-((tert-butoxycarbonyl)amino)propanoic acid for 1A to provide 36 mg of title compound. MS (m/z) 541 [M+H]$^+$.

Example 11

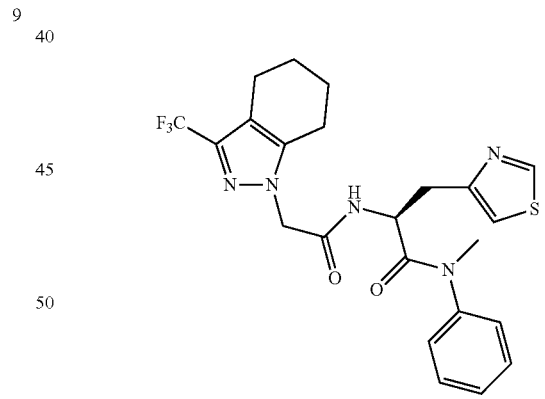

Synthesis of (S)—N-methyl-N-phenyl-3-(thiazol-4-yl)-2-(2-(3-(trifluoromethyl)-4,5,6,7-tetrahydro-1H-indazol-1-yl)acetamido)propanamide (11)

Compound 11 was prepared according to the method presented for the synthesis of Example 1 utilizing (S)-2-((tert-butoxycarbonyl)amino)-3-(thiazol-4-yl)propanoic acid for 1A to provide 23 mg of title compound. MS (m/z) 492 [M+H]$^+$.

Example 12

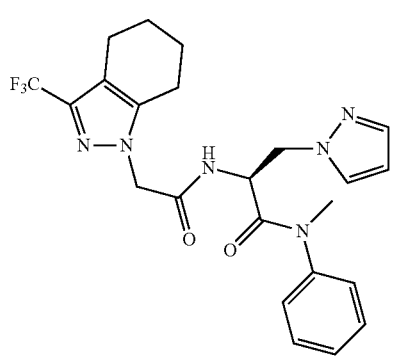

Synthesis of (S)—N-methyl-N-phenyl-3-(1H-pyrazol-1-yl)-2-(2-(3-(trifluoromethyl)-4,5,6,7-tetrahydro-1H-indazol-1-yl)acetamido)propanamide (12)

Compound 12 was prepared according to the method presented for the synthesis of Example 1 utilizing (S)-2-((tert-butoxycarbonyl)amino)-3-(1H-pyrazol-1-yl)propanoic acid for 1A to provide 20 mg of title compound. MS (m/z) 475 [M+H]$^+$.

Example 13

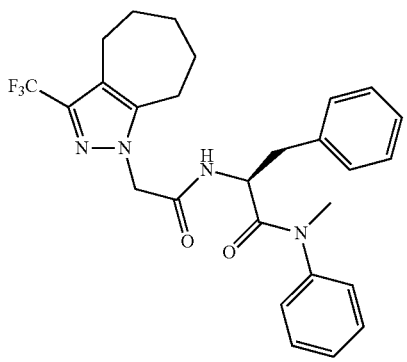

Synthesis of (S)—N-methyl-N,3-diphenyl-2-(2-(3-trifluoromethyl)-5,6,7,8-tetrahydrocyclohepta[c]pyrazol-1(4H)-yl)acetamido)propanamide (13)

Compound 13 was prepared according to the method presented for the synthesis of Example 1 utilizing 1A and substituting 2-(3-(trifluoromethyl)-5,6,7,8-tetrahydrocyclohepta[c]pyrazol-1(4H)-yl)acetic acid for 2-(3-(trifluoromethyl)-4,5,6,7-tetrahydro-1H-indazol-1-yl)acetic acid to provide 20 mg of title compound. MS (m/z) 499 [M+H]$^+$.

Example 14

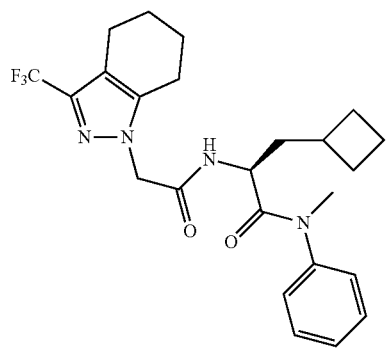

Synthesis of (S)-3-cyclobutyl-N-methyl-N-phenyl-2-(2-3-(trifluoromethyl)-4,5,6,7-tetrahydro-1H-indazol-1-yl)acetamido)propanamide (14)

Compound 14 was prepared according to the method presented for the synthesis of Example 1 utilizing (S)-2-((tert-butoxycarbonyl)amino)-3-cyclobutylpropanoic acid for 1A to provide 20 mg of title compound. MS (m/z) 463 [M+H]$^+$, $^1$H NMR (400 MHz, DMSO-d$_6$) δ 8.47 (d, 1H), 7.52-7.25 (m, 4H), 4.74 (s, 2H), 4.22 (td, 4.2 Hz, 1H), 3.13 (d, 3H), 2.53-2.41 (m, 6H), 2.04 (p, 1H), 1.86-1.74 (m, 1H), 1.71-1.45 (m, 7H), 1.44-1.28 (m, 1H), 0.76 (q, 1H).

Example 15

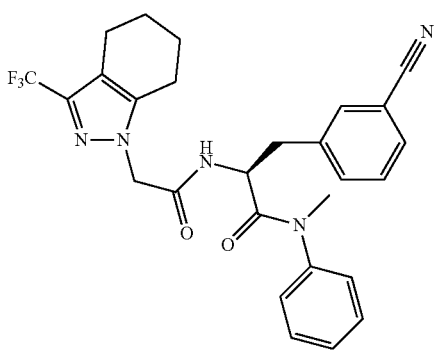

Synthesis of (S)-3-(3-cyanophenyl)-N-methyl-N-phenyl-2-(2-(3-(trifluoromethyl)-4,5,6,7-tetrahydro-1H-indazol-1-yl)acetamido)propanamide (15)

Compound 15 was prepared according to the method presented for the synthesis of Example 1 utilizing (S)-2-((tert-butoxycarbonyl)amino)-3-(3-cyanophenyl)propanoic acid for 1A to provide 7 mg of title compound. MS (m/z) 510 [M+H]$^+$. $^1$H NMR (400 MHz, DMSO-d$_6$) δ 8.73 (d, 1H), 7.62 (d, 1H) 7.53-7.31 (m, 4H), 7.30-7.13 (m, 3H), 7.08 (d, 1H), 4.75-4.61 (m, 2H), 2.91 (d, 1H), 2.72 (d, 1H), 2.37 (d, 3H), 2.12 (d, 1H), 1.60 (m, 4H).

Example 16

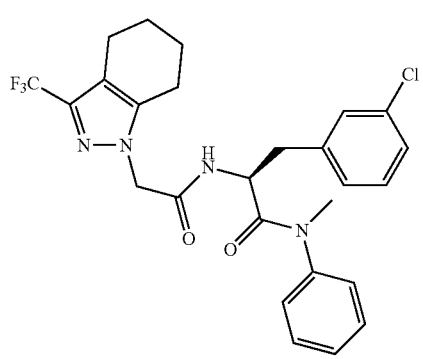

Synthesis of (S)-3-(3-chlorophenyl)-N-methyl-N-phenyl-2-(2-(3-(trifluoromethyl)-4,5,6,7-tetrahydro-1H-indazol-1-yl)acetamido)propanamide (16)

Compound 16 was prepared according to the method presented for the synthesis of Example 1 utilizing (S)-2-((tert-butoxycarbonyl)amino)-3-(3-chlorophenyl)propanoic acid for 1A to provide 8 mg of title compound. MS (m/z) 519 [M+H]$^+$. $^1$H NMR (400 MHz, DMSO-d$_6$) δ 8.74 (d, 1H), 7.40 (dd, 3H), 7.19 (dt, 4H), 6.84-6.65 (m, 2H), 4.77-4.61 (m, 2H), 4.45 (m, 1H), 2.88-2.81 (m, 1H), 2.64 (dd, 1H), 2.33 (m, 3H), 2.15 (m, 1H), 1.60 (in, 4H).

Example 17

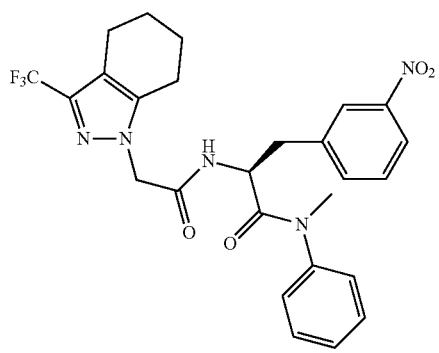

Synthesis of (S)—N-methyl-3-(3-nitrophenyl)-N-phenyl-2-(2-(3-(trifluoromethyl)-4,5,6,7-tetrahydro-1H-indazol-1-yl)acetamido)propanamide (17)

Compound 17 was prepared according to the method presented for the synthesis of Example 1 utilizing (S)-2-((tert-butoxycarbonyl)amino)-3-(3-nitrophenyl)propanoic acid for 1A to provide 7 mg of title compound. MS (m/z) 530 [M+H]$^+$. $^1$H NMR (400 MHz, DMSO-d$_6$) δ 8.79 (d, 1H), 8.01 (d, 1H), 7.64 (s, 1H), 7.54-7.31 (m, 4H), 7.23 (d, 3H), 4.76-4.61 (m, 2H), 2.99 (s, 1H), 2.87-2.73 (m, 1H), 2.42 (d, 2H), 2.29 (s, 1H), 2.14 (s, 1H), 1.58 (m, 4H).

Example 18

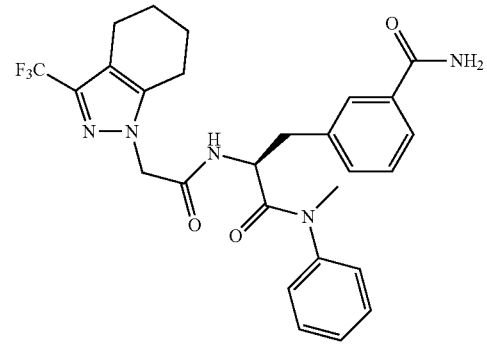

Synthesis of (S)-3-(3-(methyl(phenyl)amino)-3-oxo-2-(2-(3-(trifluoromethyl)-4,5,6,7-tetrahydro-1H-indazol-1-yl)acetamido)propyl)benzamide (18)

Compound 18 was prepared according to the method presented for the synthesis of Example 1 utilizing (S)-2-((tert-butoxycarbonyl)amino)-3-(3-carbamoylphenyl)propanoic acid for 1A to provide 11 mg of title compound. MS (m/z) 528 [M+]$^+$. $^1$H NMR (400 MHz, DMSO-d$_6$) δ 8.70 (d, 1H), 7.78 (s, 1H), 7.68-7.58 (m, 1H), 7.47-7.17 (m, 6H), 7.11 (d, 2H), 6.87 (d, 1H), 4.79-4.63 (m, 2H), 2.96-2.87 (m, 1H), 2.71-2.64 (m, 1H), 2.42 (s, 2H), 2.32 (d, 1H), 2.14 (d, 1H), 1.60 (m, 4H).

Example 19

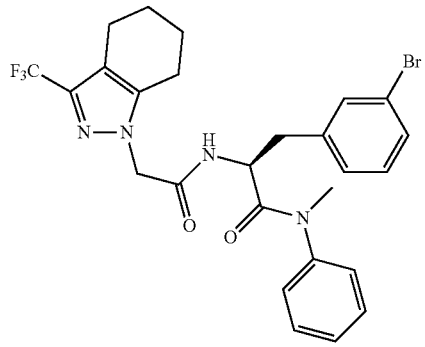

Synthesis of (S)-3-(3-bromophenyl)-N-methyl-N-phenyl-2-(2-(3-(trifluoromethyl)-4,5,6,7-tetrahydro-1H-indazol-1-yl)acetamido)propanamide (19)

Compound 19 was prepared according to the method presented for the synthesis of Example 1 utilizing (S)-3-(3-bromophenyl)-2-((tert-butoxycarbonyl)amino)propanoic acid for 1A to provide 5 mg of title compound. MS (m/z) 563 [M+H]$^+$. $^1$H NMR (400 MHz, DMSO-d$_6$) δ 8.74 (d, 1H), 7.50-7.29 (m, 4H), 7.21 (d, 2H), 7.11 (t, 1H), 6.91 (s, 1H), 6.78 (s, 1H), 4.76-4.60 (m, 2H), 4.44 (s, 1H), 2.85 (d, 1H), 2.42 (s, 3H), 2.16 (s, 1H), 1.61 (m, 4H).

Example 20

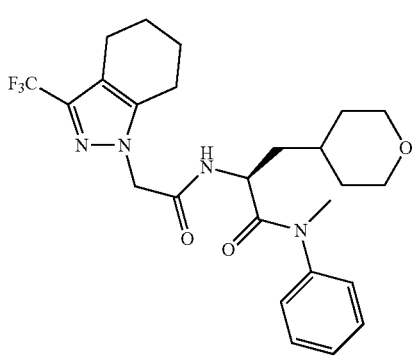

Synthesis of (S)—N-methyl-N-phenyl-3-(tetra-hydro-2H-pyran-4-yl)-2-(2-(3-(trifluoromethyl)-4,5,6,7-tetrahydro-1H-indazol-1-yl)acetamido)propan-amdide (20)

Compound 20 was prepared according to the method presented for the synthesis of Example 1 utilizing (S)-2-((tert-butoxycarbonyl)amino)-3-(tetrahydro-2H-pyran-4-yl) propanoic acid for 1A to provide 30 mg of title compound. MS (n/z) 493 [M+H]$^+$. $^1$H NMR (400 MHz, DMSO-d$_6$) δ 8.54 (d, 1H), 7.39 (dd, 4H), 4.76 (s, 2H), 4.49-4.37 (m, 1H), 3.74-3.58 (m, 1H), 3.53 (dd, 1H), 3.12 (s, 3H), 2.95 (t, 1H), 2.51 (t, 2H), 1.78-1.55 (m, 4H), 1.48-1.14 (m, 4H), 0.96 (dt, 2H), 0.41 (dd, 1H),

Example 21

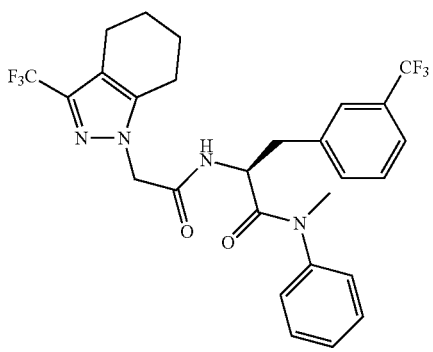

Synthesis of (S)—N-methyl-N-phenyl-2-(2-(3-(trifluoromethyl)-4,5,6,7-tetrahydro-1H-indazol-1-yl) acetamido)-3-(3-(trifluoromethyl)phenyl)propana-mide (21)

Compound 21 was prepared according to the method presented for the synthesis of Example 1 utilizing (2S)-2-[(tert-butoxycarbonyl)amino]-3-[3-trifluoromethyl)phenyl] propanoic acid for 1A to provide 12 mg of title compound. MS (m/z) 553 [M+H]$^+$.

Example 22

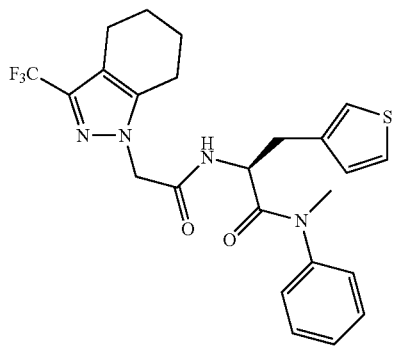

Synthesis of (S)—N-methyl-N-phenyl-3-(thiophen-3-yl)-2-(2-(3-(trifluoromethyl)-4,5,6,7-tetrahydro-1H-indazol-1-yl)acetamido)propanamide (22)

Compound 22 was prepared according to the method presented for the synthesis of Example 1 utilizing (S)-2-((tert-butoxycarbonyl)amino)-3-(thiophen-3-yl)propanoic acid for 1A to provide 5 mg of title compound. MS (m/z) 4.91 [M+H]$^+$.

Example 23

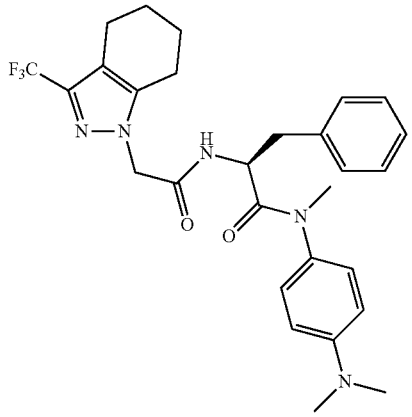

Synthesis of (S)—N-(4-(dimethylamino)phenyl)-N-methyl-3-phenyl-2-(2(3-(trifluoromethyl)-4,5,6,7-tetrahydro-1H-indazol-1-yl)acetamido)propanamide (23)

Compound 23 was prepared according to the method presented for the synthesis of Example 1 utilizing 1A and substituting N1,N1,N4-trimethylbenzene-1,4-diamine for N-methylaniline to provide 58 mg of title compound. MS (m/z) 528 [M+H]$^+$. $^1$H NMR (400 MHz, DMSO-d$_6$) δ 8.72-8.54 (m, 1H), 7.14 (d, 3H), 6.96 (d, 2H), 6.82 (d, 2H), 6.69 (d, 2H), 4.77-4.58 (m, 2H), 3.06 (s, 3H), 2.88 (s, 6H), 2.65-2.58 (m, 1H), 2.41 (d, 1H), 2.33 (d, 1H), 2.16 (s, 1H), 1.73-1.55 (m, 5H).

Example 24

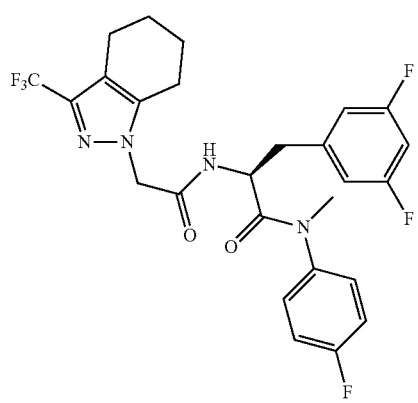

Synthesis of (S)-3-(3,5-difluorophenyl)-N-(4-fluorophenyl)-N-methyl-2-(2-(3-(trifluoromethyl)-4,5,6,7-tetrahydro-1H-indazol-1-yl)acetamido)propanamide (28)

Compound 28 was prepared according to the method presented for the synthesis of Example 1 utilizing (S)-2-((tert-butoxycarbonyl)amino)-3-(3,5-difluorophenyl)propanoic acid for 1A and substituting 4-fluoro-N-methylaniline for N-methylaniline to provide 17 mg of title compound. MS (m/z) 551 [M+H]⁺.

Example 25

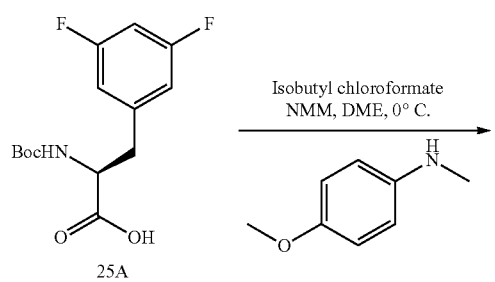

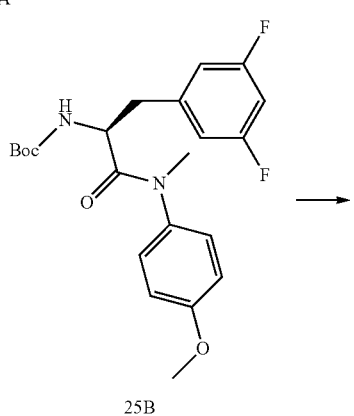

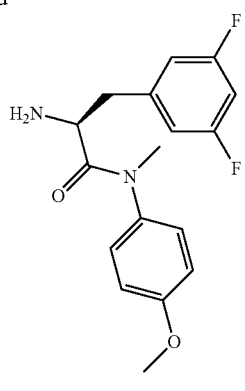

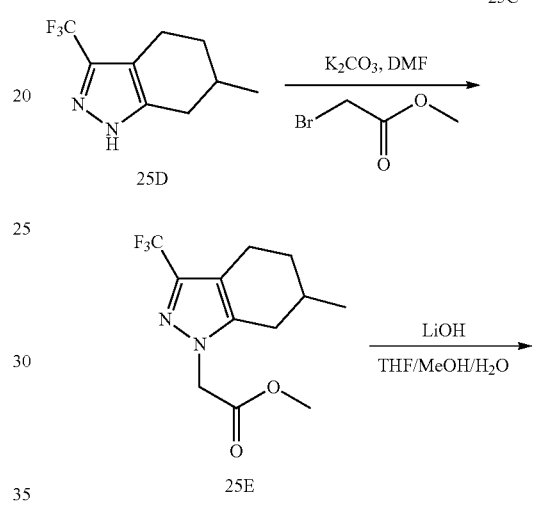

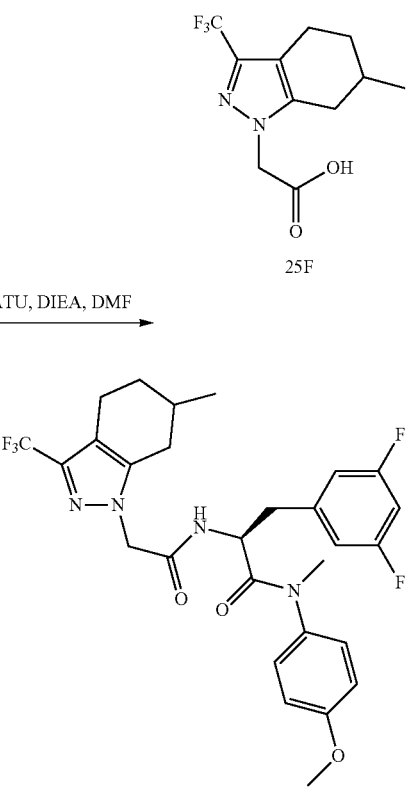

Synthesis of (S)-tert-butyl 3-(3,5-difluorophenyl)-1-((4-methoxyphenyl)(methyl)amino)-1-oxopropan-2-ylcarbamate (25B)

The title compound was prepared according to the method presented for the synthesis of 1B in Example 1 utilizing (S)-2-(tert-butoxycarbonylamino)-3-(3,5-difluorophenyl)propanoic acid and 4-methoxy-N-methylaniline to provide title compound.

Synthesis of (S)-2-amino-3-(3,5-difluorophenyl)-N-(4-methoxyphenyl)-N-methylpropanamide (25)

To a solution of 25B in DCM, TFA was added stirred for 1 hour. The solvent was removed and concentrated to dryness in vacuo. The material was used directly without further purification. MS (m/z) 321.0 [M+H]$^+$.

Synthesis of methyl 2-(6-methyl-3-(trifluoromethyl)-4,5,6,7-tetrahydro-1H-indazol-1-yl)acetate (25E)

The title compound was prepared according to the method presented for the synthesis of 31C in Example 31 utilizing 6-methyl-3-(trifluoromethyl)-4,5,6,7-tetrahydro-1H-indazole (obtained via the method described in WO2008/148832, which is incorporated by reference) to provide title compound.

Synthesis of 2-(6-methyl-3-(trifluoromethyl)-4,5,6,7-tetrahydro-1H-indazol-1-yl)acetic acid (25F)

The title compound was prepared from 25E according to the method presented for the synthesis of 31D in Example 31 to provide title compound.

Synthesis of (2S)-3-(3,5-difluorophenyl)-N-(4-methoxyphenyl)-N-methyl-2-(2-(6-methyl-3-(trifluoromethyl)-4,5,6,7-tetrahydro-1H-indazol-1-yl)acetamido)propanamide (25)

The title compound was prepared according to the method presented for the synthesis of 1C in Example 1 utilizing 25C and 25F to provide title compound (87 mg). MS (m/z) 565.2 [M+H]$^+$.

Example 26

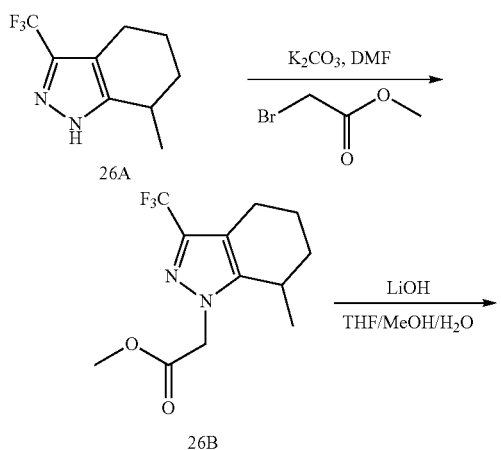

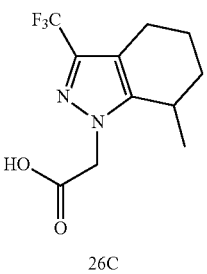

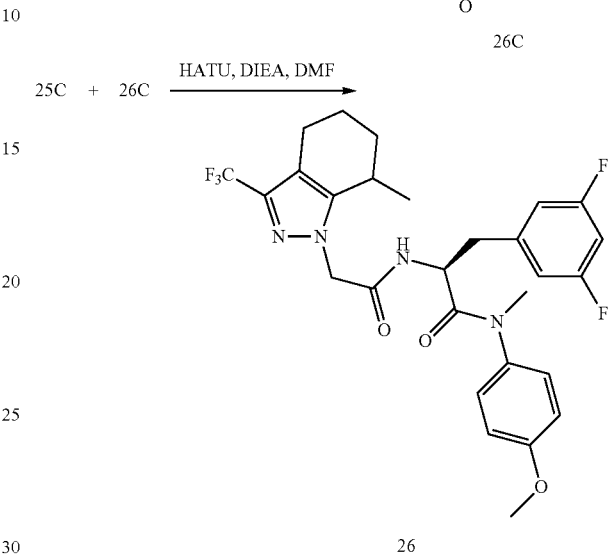

Synthesis of methyl 2-(7-methyl-3-(trifluoromethyl)-4,5,6,7-tetrahydro-1H-indazol-1-yl)acetate (26B)

The title compound was prepared according to the method presented for the synthesis of 31C in Example 31 utilizing 7-methyl-3-(trifluoromethyl)-4,5,6,7-tetrahydro-1H-indazole (obtained via the method described in WO2008/148832, which is incorporated by reference) to provide title compound.

Synthesis of 2-(7-methyl-3-trifluoromethyl)-4,5,6,7-tetrahydro-1H-1-indazol-1-yl)acetic acid (26C)

The title compound was prepared from 26B according to the method presented for the synthesis of 31D in Example 31 to provide title compound.

Synthesis of (2S)-3-(3,5-difluorophenyl)-N-(4-methoxyphenyl)-N-methyl-2-(2-(7-methyl-3-(trifluoromethyl)-4,5,6,7-tetrahydro-1H-indazol-1-yl)acetamido)propanamide (26)

The title compound was prepared according to the method presented for the synthesis of 1C in Example 1 utilizing 25C and 26C to provide title compound (40 mg). MS (m/z) 565.2 [M+H]$^+$.

Example 27

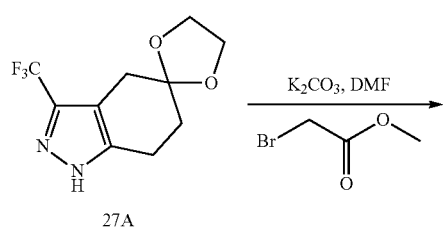

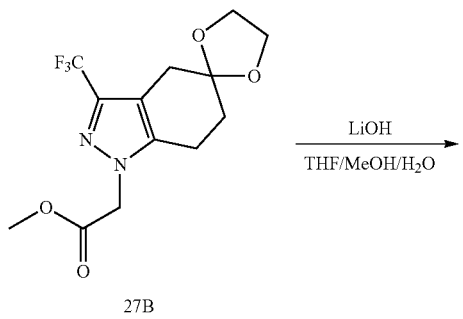

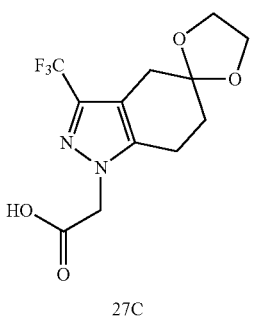

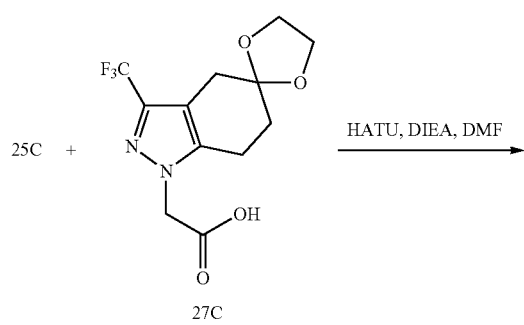

Synthesis of methyl 2-(3'-(trifluoromethyl)-6',7'-dihydrospiro[[1,3]dioxolane-2,5'-indazole]-1'(4H)-yl)acetate (27B)

The title compound was prepared according to the method presented for the synthesis of 31C in Example 31 utilizing 3'-(trifluoromethyl)-1',4',6',7'-tetrahydrospiro[[1,3]dioxolane-2,5'-indazole] (obtained via the method described in WO2008/148832, which is incorporated by reference) to provide title compound.

Synthesis of 2-(3'-(trifluoromethyl)-6',7'-dihydrospiro[[1,3]dioxolane-2,5'-indazole]-1'(4'H)-yl) acetic acid (27C)

The title compound was prepared from 27B according to the method presented for the synthesis of 31D in Example 31 to provide title compound.

Synthesis of (2S)-3-(3,5-difluorophenyl)-N-(4-methoxyphenyl)-N-methyl-2-(2-(7-methyl-3-(trifluoromethyl-4,5,6,7-tetrahydro-1H-indazol-1-yl)acetamido)propanamide (27)

The title compound was prepared according to the method presented for the synthesis of 1C in Example 1 utilizing 25C and 27C to provide title compound (12 mg). MS (m/z) 608.7 [M+H]$^+$.

Example 28

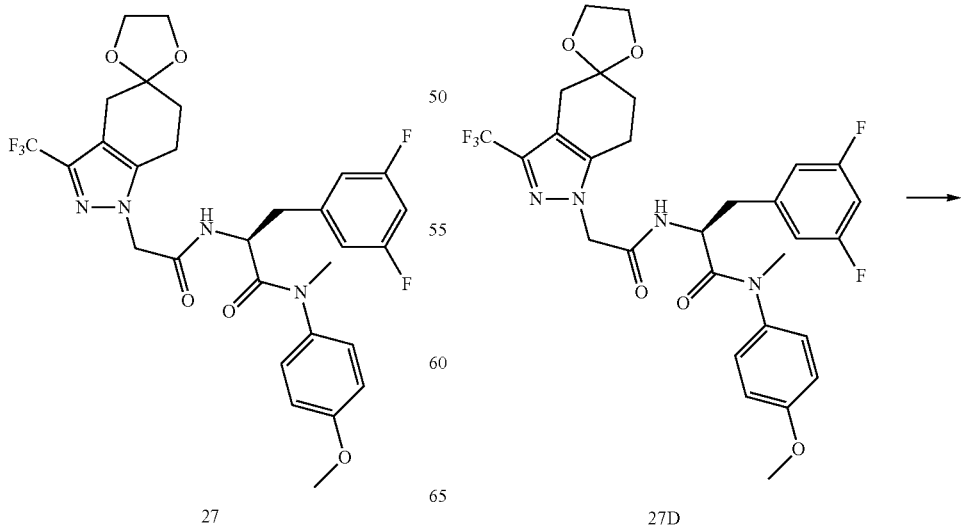

-continued

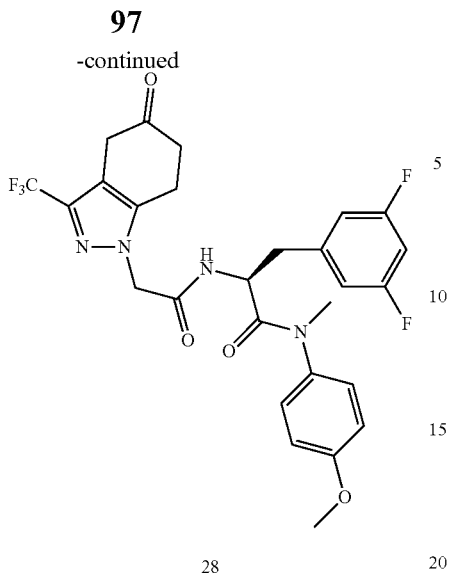

28

Synthesis of (S)-3-(3,5-difluorophenyl)-N-(4-methoxyphenyl)-N-methyl-2-(2-(5-oxo-3-(trifluoromethyl)-4,5,6,7-tetrahydro-1H-indazol-1-yl)acetamido)propanamide (28)

Compound 27D (40 mg) was dissolved in 3 mL of 50% TFA/CH$_2$Cl$_2$, to it was added 30 μL of water. After stirring at ambient temperature for 30 minutes, it was quenched with saturated aqueous sodium bicarbonate and extracted with CH$_2$Cl$_2$. The organic layer was separated, dried over sodium sulfate and concentrated. The residue was purified by reverse phase HPLC eluting with acetonitrile/water (with 0.1% TFA) to afford 15 mg of the title compound. MS (m/z) 565.0 [M+H]$^+$.

Example 29

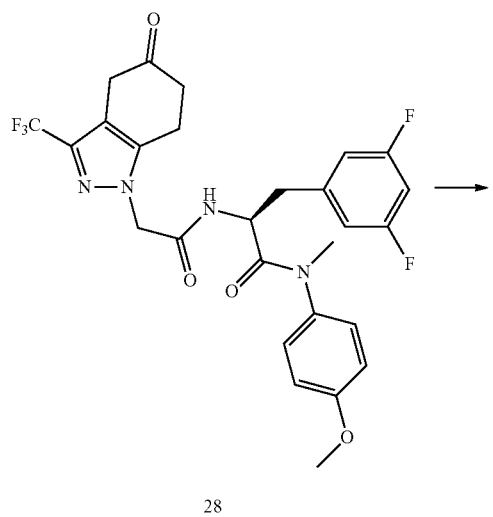

28

-continued

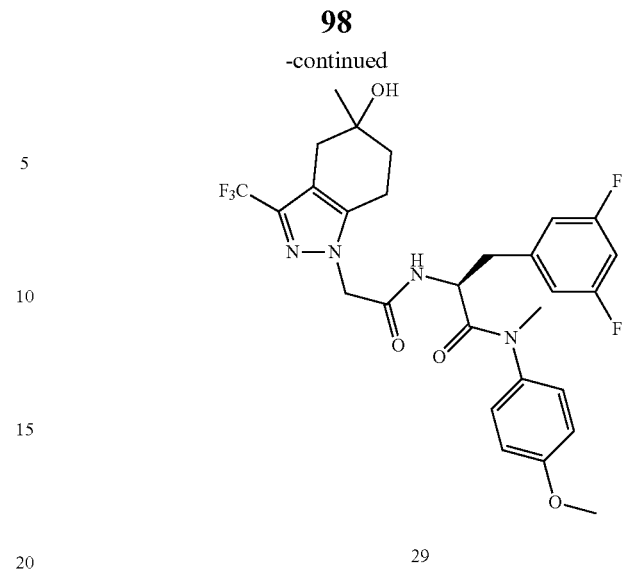

29

Synthesis of (2S)-3-(3,5-difluorophenyl)-2-(2-(5-hydroxy-5-methyl-3-(trifluoromethyl)-4,5,6,7-tetrahydro-1H-indazol-1-yl)acetamido)-N-(4-methoxyphenyl)-N-methylpropanamide (29)

Compound 2 (38 mg, 0.067 mmol) was dissolved in 0.5 mL of THF and cooled down to 0° C. To it was added MeMgBr (3N in diethylether, 22 μL, 0.066 mmol) and stirred at 0° C. for two hours. MeMgBr (3N in diethylether, 22 μL, 0.066 mmol) was added and the reaction mixture was allowed to stir at ambient temperature for overnight. More MeMgBr (3N in diethylether, 22 μL, 0.066 mmol) was added and stirred at ambient temperature for two hours. It was quenched with water at 0° C. and extracted with EtOAc. The organic layer was separated, dried over sodium sulfate and concentrated. The residue was purified by reverse phase HPLC eluting with acetonitrile/water (with 0.1% TFA) to afford 13 mg of the title compound. MS (m/z) 581.1 [M+H]$^+$.

Example 30

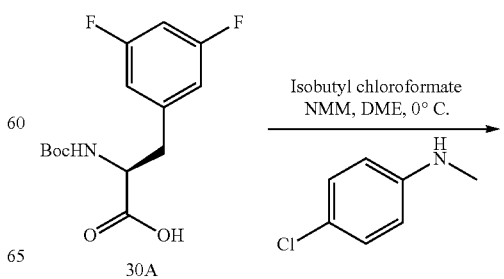

30A

-continued

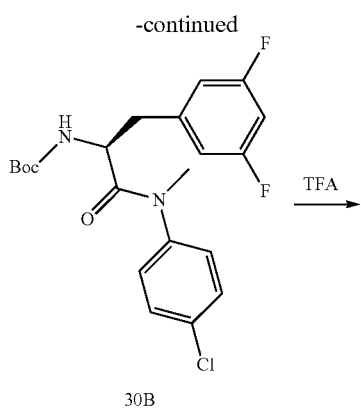

Synthesis of (S)-tert-butyl 1-((4-chlorophenyl)(methyl)amino)-3-3,5-difluorophenyl)-1-oxopropan-2-ylcarbamate (30B)

The title compound was prepared according to the method presented for the synthesis of 1B in Example 1 utilizing (S)-2-(tert-butoxycarbonylamino)-3-(3,5-difluorophenyl)propanoic acid and 4-chloro-N-methylaniline to provide title compound.

Synthesis of (S)-2-amino-N-(4-chlorophenyl)-3-(3,5-difluorophenyl)-N-methylpropanamide (30C)

The title compound was prepared from 30B according to the method presented for the synthesis of 25C in Example 25 to provide title compound MS (m/z) 325.1 [M+H]$^+$.

Synthesis of (S)—N-(4-chlorophenyl-3-(3,5-difluorophenyl)-N-methyl-2-(2-(3-oxo-2,3,4,5,6,7-hexahydro-1H-indazol-1-yl)acetamido)propanamide (30)

The title compound was prepared according to the method presented for the synthesis of 1C in Example 1 utilizing 30C and 2-(3-oxo-2,3,4,5,6,7-hexahydro-1H-indazol-1-yl)acetic acid (30D) to provide title compound (25 mg). MS (m/z) 503.4 [M+H]$^+$.

Example 31

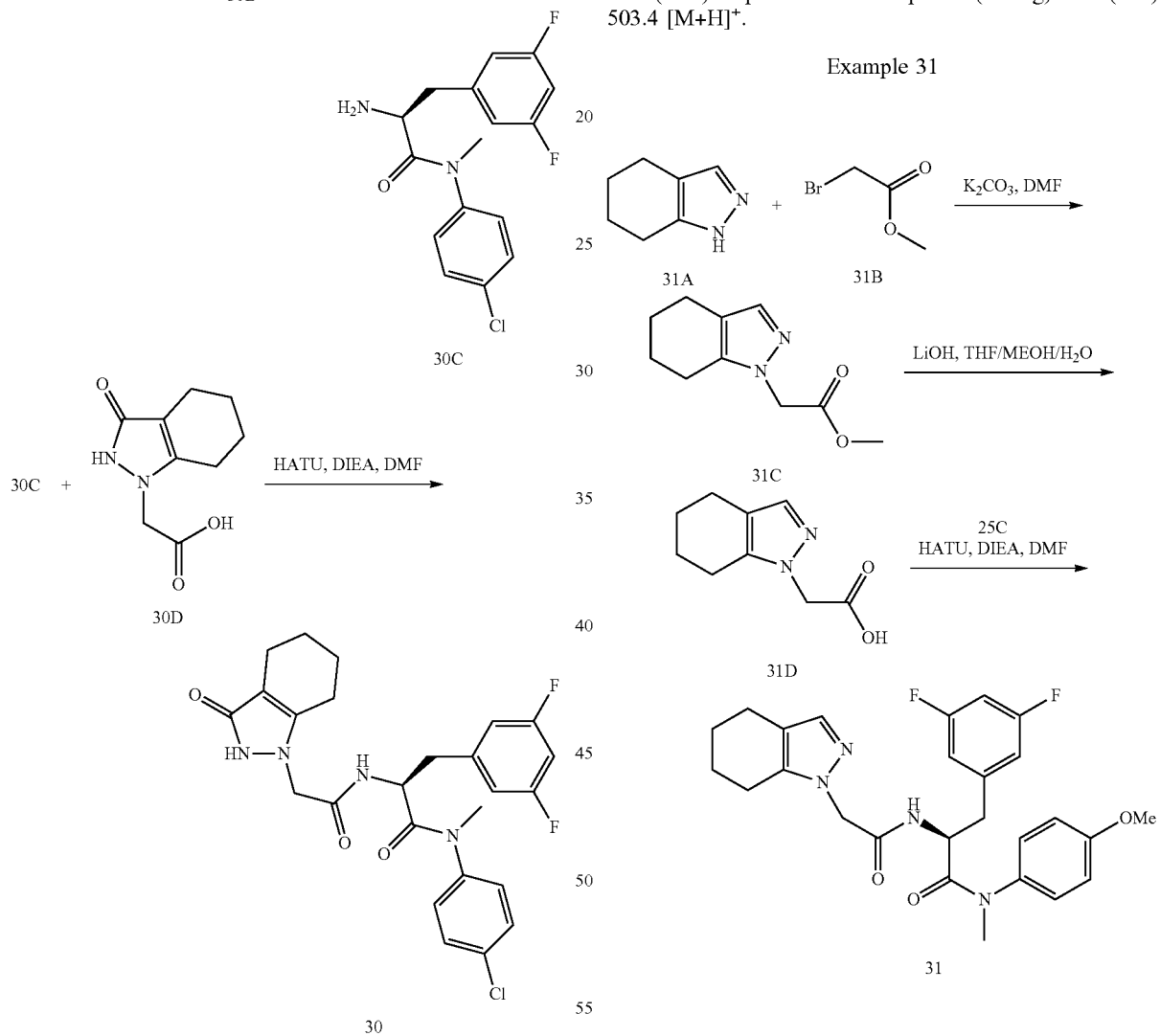

Synthesis of methyl 2-(4,5,6,7-tetrahydro-1H-indazol-1-yl)acetate (31C)

To a solution of 4,5,6,7-tetrahydro-1H-indazole (488 mg, 4.0 mmol) in DMF (5 mL) was slowly added potassium carbonate (1.1 g, 8.0 mmol) and methyl 2-bromoacetate (765 mg, 5.0 mmol) at room temperature. The reaction mixture was stirred at room temperature for 1 h and was then poured into ethyl acetate (150 mL) and washed with 5% LiCl solution. The organic layer was dried over sodium sulfate, filtered and concentrated to afford the title product (800 mg crude, used in the next step without further purification). MS (m/z): 195.0 [M+H]$^+$; HPLC retention time 2.69 min (2-98% acetonitrile:water with 0.05% trifluoroacetic acid).

Synthesis of 4-bromo-5-ethyl-3-(trifluoromethyl)-1H-pyrazole (31D)

To a solution of methyl 2-(4,5,6,7-tetrahydro-1H-indazol-1-yl)acetate (31C) (800 mg crude, 4.0 mmol) in a mixture of THF (10 mL), MeOH (1 mL) and H$_2$O (1 mL) was added lithium chloride monohydrate (840 mg, 20 mmol). The reaction mixture was stirred at room temperature for 5 min and was then poured into ethyl acetate and washed with saturated NH$_4$Cl solution and brine. The organic layer was dried over sodium sulfate, filtered and concentrated. The crude product was used in the next step without further purification. MS (m/z): 181.3 [M+H]$^+$; HPLC retention time 2.16 min (2-98% acetonitrile:water with 0.05% trifluoroacetic acid).

Synthesis of (S)-3-(3,5-difluorophenyl)-N-(4-methoxyphenyl)-N-methyl-2-(2-(4,5,6,7-tetrahydro-1H-indazol-1-yl)acetamido)propanamide (31)

The title compound was prepared according to the method presented for the synthesis of Example 1 utilizing 31D and (S)-2-amino-3-(3,5-difluorophenyl)-N-(4-methoxyphenyl)-N-methylpropanamide to provide (S)-3-(3,5-difluorophenyl)-N-(4-methoxyphenyl)-N-methyl-2-(2-(4,5,6,7-tetrahydro-1H-indazol-4-yl)acetamido)propanamide: MS (m/z): 483.0 [M+H]$^+$; HPLC retention time 2.15 min (2-98% acetonitrile:water with 0.05% trifluoroacetic acid). $^1$H NMR (400 MHz, cd$_3$cl) δ 7.69 (d, J=8.0 Hz, 1H), 7.30 (s, 1H), 6.89 (s, 4H), 6.64 (t, J=8.8 Hz, 1H), 6.37 (d, J=6.4 Hz, 2H), 4.96 (s, 2H), 4.74 (q, J=7.6 Hz, 1H), 3.83 (s, 3H), 3.21 (s, 1H), 2.89-2.84 (m, 1H), 2.76-2.69 (m, 3H), 2.56-2.53 (m, 2H), 1.86-1.76 (m, 4H).

Example 32

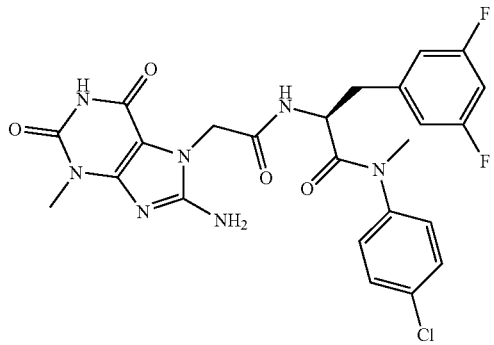

Synthesis of (S)-2-(2-(8-amino-3-methyl-2,6-dioxo-2,3-dihydro-1H-purin-7(6)-yl)acetamido)-N-(4-chlorophenyl)-3-(3,5-difluorophenyl)-N-methylpropanamide (32)

The title compound was prepared according to the method presented for the synthesis of 1C in Example 1 utilizing 30C and 2-(8-amino-3-methyl-2,6-dioxo-2,3-dihydro-1H-purin-7(6H)-yl)acetic acid to provide title compound (1.2 mg). MS (m/z) 545.9 [M+H]$^+$.

Example 33

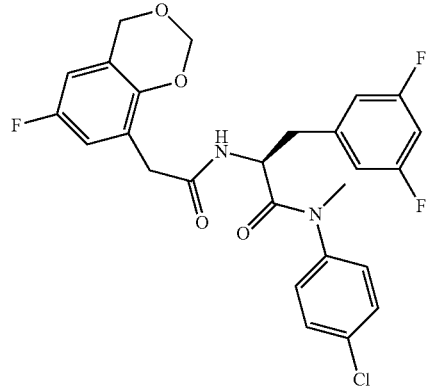

Synthesis of (S)—N-(4-chlorophenyl)-3-(3,5-difluorophenyl)-2-(2-(6-fluoro-4H-benzo[d][1,3]dioxin-8-yl)acetamido)-N-methylpropanamide (33)

The title compound was prepared according to the method presented for the synthesis of 1C in Example 1 utilizing 30C and 2-(6-fluoro-4H-benzo[d][1,3]dioxin-8-yl)acetic acid to provide title compound (5 mg), MS (m/z) 518.8 [M+H]$^+$.

Example 34

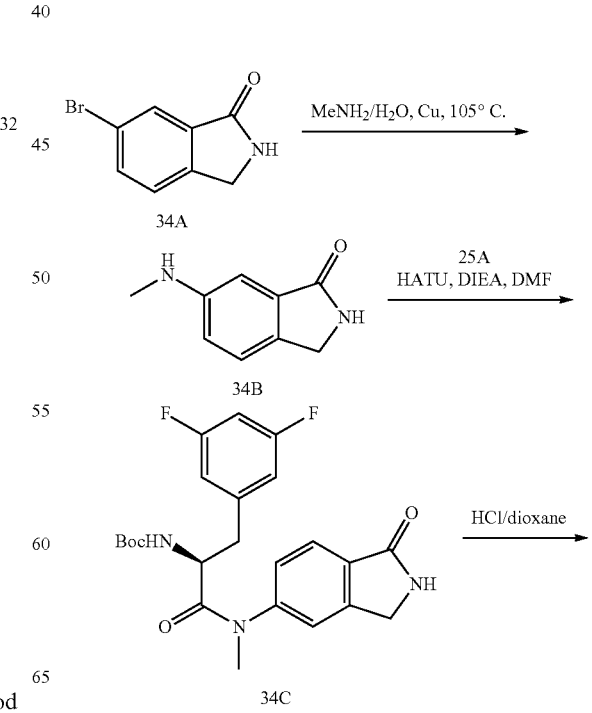

103

-continued

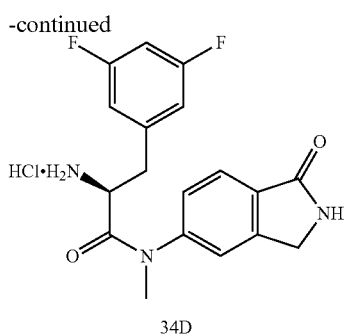

34D

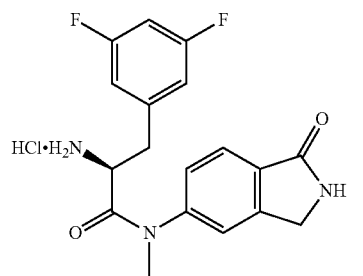

34D

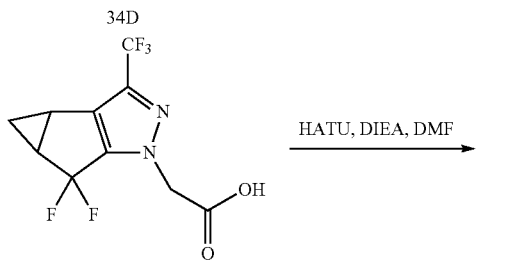

34E

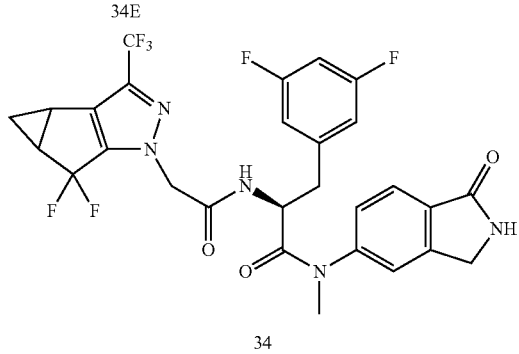

34

Synthesis of 6-(methylamino)isoindolin-1-one (34B)

6-bromoisoindolin-1-one (1050 mg, 5.0 mmol), copper powder (32 mg, 0.5 mmol) and methylamine (40% in $H_2O$, 2.7 mL) were placed in a pressure vessel and the sealed reaction was heated at 105° C. overnight. The reaction mixture was poured into ethyl acetate (150 mL) and washed with saturated $NH_4Cl$ solution. The organic layer was dried over sodium sulfate, filtered and concentrated. The volatile was removed in vacuo and the residue was then purified by silica gel chromatography eluting with MeOH and dichloromethane (Rf=0.2, 5% MeOH in DCM) to afford 300 mg of the title compound. MS (m/z): 163.13 $[M+H]^+$; HPLC retention time 0.17 min (2-98% acetonitrile:water with 0.05% trifluoroacetic acid). $^1H$ NMR (400 MHz, dmso) δ 8.28 (s, 1H), 7.20 (d, J=8.2 Hz, 1H), 6.75 (dd, 8.2, 2.2 Hz, 1H), 6.68 (d, J=2.1 Hz, 1H), 5.83 (d, J=5.0 Hz, 1H), 4.15 (s, 2H), 2.66 (d, J=5.1 Hz, 3H).

Synthesis of (S)-tert-butyl (3-(3,5-difluorophenyl)-1-(methyl(1-oxoisoindolin-5-yl)amino)-1-oxopropan-2-yl)carbamate (34C)

The title compound was prepared according to the method presented for the synthesis of 1B in Example 1 utilizing 34B and (S)-2-((tert-butoxycarbonyl)amino)-3-(3,5-difluorophenyl)propanoic acid to provide (S)-tert-butyl (3-(3,5-difluorophenyl)-1-(methyl(1-oxoisoindolin-5-yl)amino)-1-oxopropan-2-yl)carbamate; MS (m/z): 445.99 $[M+H]^+$; HPLC retention time 1.17 min (2-98% acetonitrile:water with 0.05% trifluoroacetic acid).

Synthesis of (2S)-2-(2-(5,5-difluoro-3-(trifluoromethyl)-3b,4,4a,5-tetrahydro-1H-cyclopropa[3,4]-cyclopenta[1,2-c]pyrazol-1-yl)acetamido)-3-(3,5-difluorophenyl)-N-methyl-N-(1-oxoisoindolin-5-yl)propanamide (34D)

To (S)-tert-butyl (3-(3,5-difluorophenyl)-1-(methyl(1-oxoisoindolin-5-yl)amino)-1-oxopropan-2-yl)carbamate in DCM was added 4N HCl in dioxanes. The reaction was stirred at ambient temperature until full conversion was observed by LCMS. Removal of solvents provided the title product which was used without further purification: MS (m/z); 346.32 $[M+H]^+$.

Synthesis of (2S)-2-(2-(5,5-difluoro-3-(trifluoromethyl)-3b,4,4a,5-tetrahydro-1H-cyclopropa[3,4]cyclopenta[1,2-c]pyrazol-1-yl)acetamido)-3-(3,5-difluorophenyl)-N-methyl-N-(1-oxoisoindolin-5-yl)propanamide (34)

The title compound was prepared according to the method presented for the synthesis of Example 1 utilizing 34D and 2-(5,5-difluoro-3-(trifluoromethyl)-3b,4,4a,5-tetrahydro-1H-cyclopropa[3,4]cyclopenta[1,2-c]pyrazol-1-yl)acetic acid to provide (2S)-2-(2-(5,5-difluoro-3-(trifluoromethyl)-3b,4,4a,5-tetrahydro-1H-cyclopropa[3,4]cyclopenta[1,2-c]pyrazol-1-yl)acetamido)-3-(3,5-difluorophenyl)-N-methyl-N-(1-oxoisoindolin-5-yl)propanamide as a mixture of diastereomers: MS (m/z): 610.31 $[M+H]^+$; HPLC retention time 1.30 min (2-98% acetonitrile:water with 0.05% trifluoroacetic acid).

Example 35

Test A: Antiviral assay in MT4 Cells

For the antiviral assay, 40 μL of a concentration required to achieve a final effective 1× test concentration of 3-fold serially diluted compound in culture medium with 10% FBS was added to each well of a 384-well plate (10 concentrations) in quadruplicate. MT4 cells were next mixed with HIV-IIIb at an m.o.i of 0.003 for 1 hour, after which time 35 μL of virus/cell mixture (2000 cells) was immediately added to each well containing 40 μL of diluted compound. The plates were then incubated at 37° C. for 5 days. After 5 days of incubation, 25 μl of 2× concentrated CellTiter-Glo™ Reagent (catalog # G7571, Promega Biosciences, Inc., Madison, Wis.) was added to each well containing MT-4 cells. Cell lysis was carried out by incubating at room temperature for 10 min and then chemiluminescence was read. EC50 values were calculated as the compound concentration that caused a 50% decrease in luminescence signal, a measure of HIV-1 replication. Percent inhibition of virus-induced cell killing calculated from the dose response curve at 2 μM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity (Test A) as depicted in the table below. Shown below are the corresponding values for CC50 and percent inhibition of vines-induced cell killing in the presence of 2 μM drug concentration. In the table, percent inhibition values have been normalized to 100% where the calculation of percent inhibition would have resulted in a value greater than 100.

| Compound | % Inhibition at 2 μM | CC50 (nM) |
|---|---|---|
| 1 | 98 | 23525.8 |
| 2 | 100 | 18425.8 |
| 3 | 79 | 11076.9 |
| 4 | 100 | 12459.1 |
| 5 | 0 | >53000 |
| 6 | 52 | >53000 |
| 7 | 1 | >53000 |
| 8 | 95 | 25645.9 |
| 9 | 5 | >53000 |
| 10 | 2 | 10505.5 |
| 11 | 21 | >53000 |
| 12 | 10 | >53000 |
| 13 | 87 | 22205.4 |
| 14 | 16 | 28975.4 |
| 15 | 26 | 26322.9 |
| 16 | 58 | 16730.7 |
| 17 | 0 | 19170.1 |
| 18 | 0 | >53000 |
| 19 | 27 | 17287 |
| 20 | 0 | >53000 |
| 21 | 0 | 11317 |
| 22 | 94 | 25007.9 |
| 23 | 100 | 19226.1 |
| 24 | 93 | 12172.3 |
| 25 | 100 | 11124.3 |
| 26 | 100 | 9823.1 |
| 27 | 32 | 19929.9 |
| 28 | 76 | 37230.5 |
| 29 | 82 | 32072.2 |
| 30 | 100 | 22247.5 |
| 31 | 78 | >53000 |
| 32 | 39 | >53000 |
| 33 | 34 | 18390.2 |
| 34 | 97 | >53000 |

In one embodiment, the compounds demonstrate >10% inhibition at 2 μM. In one embodiment, the compounds demonstrate >30% inhibition at 2 μM. In one embodiment, the compounds demonstrate >50% inhibition at 2 μM. In one embodiment, the compounds demonstrate >70% inhibition at 2 μM. In one embodiment, the compounds demonstrate >75% inhibition at 2 μM. In one embodiment, the compounds demonstrate >80% inhibition at 2 μM. In one embodiment, the compounds demonstrate >85% inhibition at 2 μM. In one embodiment, the compounds demonstrate >90% inhibition at 2 μM. In one embodiment, the compounds demonstrate >95% inhibition at 2 μM. It is to be understood that the compounds disclosed herein can be grouped according to their % inhibition as described above.

In one variation, a compound is of any formulae provided herein, wherein the compound exhibits from 85%-100% inhibition of virus-induced cell killing at 2 μM. In other embodiments, a compound is of any formulae provided herein wherein the compound exhibits from 50-100, 60-100, 70-400, 80-100, or 90-100% inhibition of virus-induced cell killing at 2 μM.

It is understood that % inhibition may be evaluated by techniques known in the art. In a particular variation, a compound is of any formulae provided herein wherein the compound exhibits from 85%-100% inhibition of virus-induced cell killing at 2 μM as measured by the method provided in the Test A and Test B sections discussed above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds, it is to be understood that individual steps described herein may be combined. It is also to be understood that separate batches of a compound may be combined and then carried forth in the next synthetic step.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:
1. A compound of Formula I:

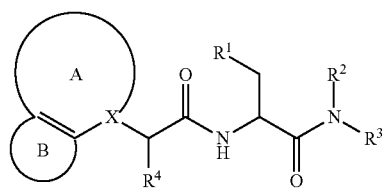

wherein:
ring A, including the two carbon atoms to which it is fused to ring B, is a 5-6 membered monocyclic heteroaryl comprising 1-2 annular nitrogen atoms and 3-4 annular carbon atoms, wherein the 5-6 membered heteroaryl of A is optionally substituted with 1, 2, or 3 $Z^1$ groups, wherein the $Z^1$ groups are the same or different;
ring B, including the two carbon atoms to which it is fused to ring A, is a 5-7 membered monocyclic carbocycle, 6-10 membered bicyclic carbocycle, 5-7 membered monocyclic heterocycle, or 6-10 membered bicyclic heterocycle, wherein any 5-7 membered monocyclic carbocycle, 6-10 membered bicyclic carbocycle, 5-7 membered monocyclic heterocycle, or 6-10 bicyclic heterocycle of B is optionally substituted with 1, 2, 3, 4 or 5 $Z^2$ groups, wherein the $Z^2$ groups are the same or different;

X is C or N;

or the moiety

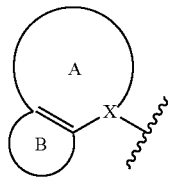

is

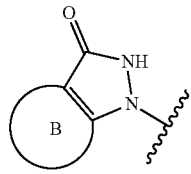

wherein B is as defined above;

$R^1$ is phenyl, 5-6 membered monocyclic heteroaryl, 5-6-membered monocyclic heterocycle, 9-10 membered bicyclic heterocycle, or 3-7 membered carbocycle, wherein any phenyl, 5-6 membered monocyclic heteroaryl, 5-6-membered monocyclic heterocycle, 9-10 membered bicyclic heterocycle, or 3-7 membered carbocycle of $R^1$ is optionally substituted with 1, 2, 3, 4 or 5 $Z^3$ groups, wherein the $Z^3$ groups are the same or different; or $R^1$ is benzothiofuranyl, in which any of the rings are optionally substituted with 1, 2, or 3 $Z^3$ groups;

$R^2$ is $(C_1\text{-}C_6)$alkyl or 3-7 membered carbocycle, wherein any $(C_1\text{-}C_6)$alkyl of $R^2$ is optionally substituted with 1, 2, 3, 4 or 5 halo groups, which may be same or different;

$R^3$ is phenyl, 9-10 membered bicyclic aryl, 5-7 membered monocyclic heterocycle, or 8-10 membered bicyclic heterocycle, wherein any phenyl, 9-10 membered bicyclic aryl, 5-7 membered monocyclic heterocycle, or 8-10 membered bicyclic heterocycle of $R^3$ is optionally substituted with 1, 2, 3, 4 or 5 $Z^4$ groups, wherein the $Z^4$ groups are the same or different;

$R^4$ is H or $(C_1\text{-}C_6)$alkyl optionally substituted with 1, 2, 3, 4 or 5 halo groups, which may be same or different;

each $Z^1$ is independently $(C_1\text{-}C_6)$alkyl, $(C_2\text{-}C_6)$alkenyl, $(C_2\text{-}C_6)$alkynyl, 3-7 membered carbocycle, halo, —CN, —$OR^{n1}$, —$OC(O)R^{p1}$, —$OC(O)NR^{q1}R^{r1}$, —$SR^{n1}$, —$S(O)R^{p1}$, —$S(O)_2OH$, —$S(O)_2R^{p1}$, —$S(O)_2NR^{q1}R^{r1}$, —$NR^{q1}R^{r1}$, —$NR^{n1}COR^{p1}$, —$NR^{n1}CO_2R^{p1}$, —$NR^{n1}CONR^{q1}R^{r1}$, —$NR^{n1}S(O)_2R^{p1}$, —$NR^{n1}S(O)_2OR^{p1}$, —$NR^{n1}S(O)_2NR^{q1}R^{r1}$, $NO_2$, —$C(O)R^{n1}$, —$C(O)OR^{n1}$, or —$C(O)NR^{q1}R^{r1}$, wherein any 3-7 membered carbocycle of $Z^1$ is optionally substituted with 1, 2, 3, 4 or 5 halo groups or $(C_1\text{-}C_6)$alkyl, which may be same or different, and wherein any $(C_1\text{-}C_6)$alkyl, $(C_2\text{-}C_6)$alkenyl and $(C_2\text{-}C_6)$alkynyl of $Z^1$ is optionally substituted with 1, 2, 3, 4 or 5 halo groups, which may be same or different;

each $R^{n1}$ is independently H or $(C_1\text{-}C_6)$alkyl;

each $R^{p1}$ is independently $(C_1\text{-}C_6)$alkyl;

each $R^{q1}$ and $R^{r1}$ is independently H or $(C_1\text{-}C_6)$alkyl;

each $Z^2$ is independently $(C_1\text{-}C_6)$alkyl, halo, oxo, or —$OR^{n2}$, wherein any 3-7 membered carbocycle of $Z^2$ is optionally substituted with 1, 2, 3, 4 or 5 $(C_1\text{-}C_6)$alkyl or halo groups, which may be same or different, and wherein any $(C_1\text{-}C_6)$alkyl of $Z^2$ is optionally substituted with 1, 2, 3, 4 or 5 halo groups, which may be same or different;

each $R^{n2}$ is independently H, $(C_1\text{-}C_3)$alkyl, $(C_1\text{-}C_3)$haloalkyl, or $(C_3\text{-}C_7)$carbocycle;

each $Z^3$ is independently $(C_1\text{-}C_6)$alkyl, halo, —CN, —$OR^{n3}$, $NO_2$, or —$C(O)NR^{q3}R^{r3}$ wherein any $(C_1\text{-}C_6)$alkyl of $Z^3$ is optionally substituted with 1, 2, 3, 4 or 5 halo groups, which may be same or different;

each $R^{n3}$ is independently H, $(C_1\text{-}C_3)$alkyl, $(C_1\text{-}C_3)$haloalkyl, or $(C_3\text{-}C_7)$carbocycle;

each $R^{q3}$ and $R^{r3}$ is independently H or $(C_1\text{-}C_6)$alkyl;

each $Z^4$ is independently $(C_1\text{-}C_6)$alkyl, $(C_2\text{-}C_6)$alkenyl, $(C_2\text{-}C_6)$alkynyl, $(C_3\text{-}C_7)$carbocycle, halo, oxo, —CN, —$OR^{n4}$, —$OC(O)R^{p4}$, —$OC(O)NR^{q4}R^{r4}$, —$SR^{n4}$, —$S(O)R^{p4}$, —$S(O)_2OH$, —$S(O)_2R^{p4}$, —$S(O)_2NR^{q4}R^{r4}$, —$NR^{q4}R^{r4}$, —$NR^{n4}COR^{p4}$, —$NR^{n4}CO_2R^{p4}$, —$NR^{n4}CONR^{q4}R^{r4}$, —$NR^{n4}S(O)_2R^{p4}$, —$NR^{n4}S(O)_2OR^{p4}$, —$NR^{n4}S(O)_2NR^{q4}R^{r4}$, $NO_2$, —$C(O)R^{n4}$, —$C(O)OR^{n4}$, or —$C(O)NR^{q4}R^{r4}$, wherein any $(C_3\text{-}C_7)$carbocycle, of $Z^1$ is optionally substituted with 1, 2, 3, 4 or 5 halo groups or $(C_1\text{-}C_6)$alkyl, and wherein any $(C_1\text{-}C_6)$alkyl, $(C_2\text{-}C_6)$alkenyl and $(C_2\text{-}C_6)$alkynyl of $Z^4$ is optionally substituted with 1, 2, 3, 4 or 5 halo groups, which may be same or different;

each $R^{n4}$ is independently H or $(C_1\text{-}C_6)$alkyl;

each $R^{p4}$ is $(C_1\text{-}C_6)$alkyl; and each $R^{q4}$ and $R^{r4}$ is independently H or $(C_1\text{-}C_6)$alkyl;

or a pharmaceutically acceptable salt thereof.

2. The compound of claim 1, or a pharmaceutically acceptable salt thereof, wherein $R^4$ is H.

3. The compound of claim 1, or a pharmaceutically acceptable salt thereof, wherein the compound of Formula I is a compound of Formula Ia:

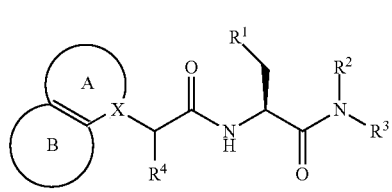

Ia

4. The compound of claim 1, or a pharmaceutically acceptable salt thereof, wherein ring A is a 5-6 membered monocyclic heteroaryl, wherein the 5-6 membered heteroaryl of A comprises 1-2 nitrogen atoms and 3-4 carbon atoms in the ring, and wherein any 5-6 membered heteroaryl of A is optionally substituted with 1 or 2 $Z^1$ groups.

5. The compound of claim 1, or a pharmaceutically acceptable salt thereof, wherein ring A, including the two carbon atoms to which it is fused to ring B, is a 5-6 membered monocyclic heteroaryl, wherein the 5-6 membered heteroaryl of A comprises 1-2 annular nitrogen atoms and 3-4 annular carbon atoms in the ring, and wherein any 5-6 membered heteroaryl of A is optionally substituted with 1 or 2 $Z^1$ groups; and X is N.

6. The compound of claim 1, or a pharmaceutically acceptable salt thereof, wherein the moiety

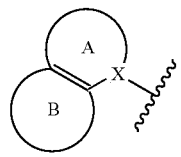

is

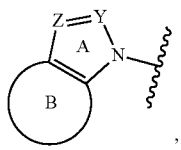

wherein:
Y is $CZ^{1a}$ or N;
Z is $CZ^{1a}$ or N; and
each $Z^{1a}$ is independently H or $Z^1$.

7. The compound of claim 1, or a pharmaceutically acceptable salt thereof, wherein the moiety

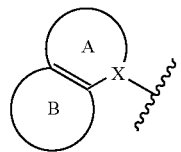

is

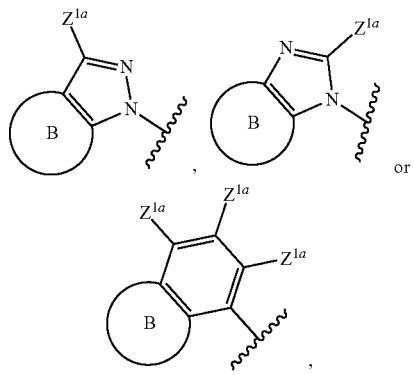

wherein each $Z^{1a}$ is independently H or $Z^1$.

8. The compound of claim 1, or a pharmaceutically acceptable salt thereof, wherein the moiety

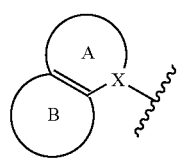

is

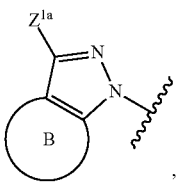

wherein each $Z^{1a}$ is independently H or $Z^1$.

9. The compound of claim 1, or a pharmaceutically acceptable salt thereof, wherein the compound of Formula I is a compound of Formula Ib:

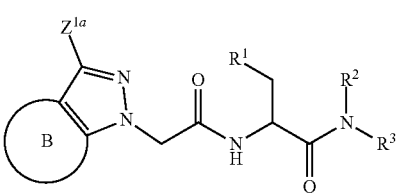

wherein $Z^{1a}$ is H or $Z^1$.

10. The compound of claim 1, or a pharmaceutically acceptable salt thereof, wherein each $Z^1$ is independently $(C_1-C_6)$alkyl, halo, —OH, or —$NR^{q1}R^{r1}$, wherein any $(C_1-C_6)$alkyl of $Z^1$ is optionally substituted with 1, 2, or 3 halo groups.

11. The compound of claim 1, or a pharmaceutically acceptable salt thereof, wherein each $Z^1$ is independently —$CF_3$, halo, —OH, or —$NH_2$.

12. The compound of claim 1, or a pharmaceutically acceptable salt thereof, wherein $Z^1$ is H, $CF_3$, or OH.

13. The compound of claim 1, or a pharmaceutically acceptable salt thereof, wherein the moiety

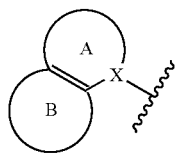

is

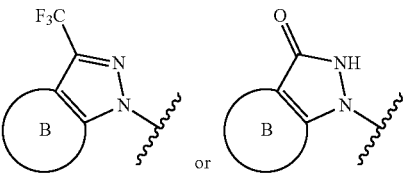

14. The compound of claim 1, or a pharmaceutically acceptable salt thereof, wherein ring B is a 5-7 membered monocyclic carbocycle, or 6-10 membered bicyclic carbocycle, wherein any 5-7 membered monocyclic carbocycle or 6-10 membered bicyclic carbocycle of B is optionally substituted with 1, 2, or 3 $Z^2$ groups.

15. The compound of claim 1, or a pharmaceutically acceptable salt thereof, wherein ring B is a 6-7 membered monocyclic carbocycle, or 6 membered bicyclic carbocycle, wherein any 6-7 membered monocyclic carbocycle or 6 membered bicyclic carbocycle of B is optionally substituted with 1, 2, or 3 $Z^2$ groups.

16. The compound of claim 1, or a pharmaceutically acceptable salt thereof, wherein ring B is a 6-10 membered bicyclic carbocycle, or 6-10 membered bicyclic heterocycle, wherein any 6-10 membered bicyclic carbocycle or 6-10 bicyclic heterocycle of B is optionally substituted with 1, 2, or 3 $Z^2$ groups.

17. The compound of claim 1, or a pharmaceutically acceptable salt thereof, wherein ring B is a 6-10 membered bicyclic carbocycle, wherein any 6-10 membered bicyclic carbocycle of B is optionally substituted with 1, 2, or 3 $Z^2$ groups.

18. The compound of claim 1, or a pharmaceutically acceptable salt thereof, wherein ring B is a 6-7 membered bicyclic carbocycle, wherein any 6-7 membered bicyclic carbocycle is optionally substituted with 1 or 2 $Z^2$ groups.

19. The compound of claim 1, or a pharmaceutically acceptable salt thereof, wherein ring B is bicyclo[3.1.0]hex-2-ene, wherein bicyclo[3.1.0]hex-2-ene is optionally substituted with 1, 2 or 3 $Z^2$ groups.

20. The compound of claim 1, or a pharmaceutically acceptable salt thereof, wherein each $Z^2$ is independently $(C_1-C_6)$alkyl, halo, or $—OR^{n2}$, wherein any $(C_1-C_6)$alkyl of $Z^2$ is optionally substituted with 1, 2, or 3 halo groups.

21. The compound of claim 1, or a pharmaceutically acceptable salt thereof, wherein each $Z^2$ is independently methyl, fluoro, oxo, or OH.

22. The compound of claim 1, or a pharmaceutically acceptable salt thereof, wherein each $Z^2$ is independently methyl, fluoro, or OH.

23. The compound of claim 1, or a pharmaceutically acceptable salt thereof, wherein the moiety

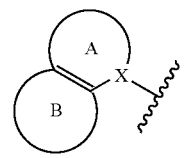

is

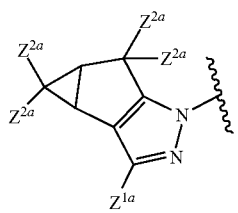

wherein $Z^{1a}$ is independently H or $Z^1$; and each $Z^{2a}$ is independently H or $Z^2$.

24. The compound of claim 1, or a pharmaceutically acceptable salt thereof, wherein the moiety

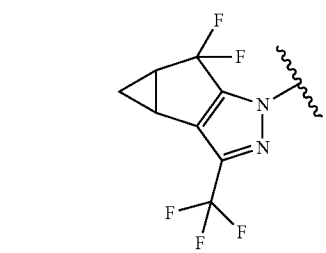

is

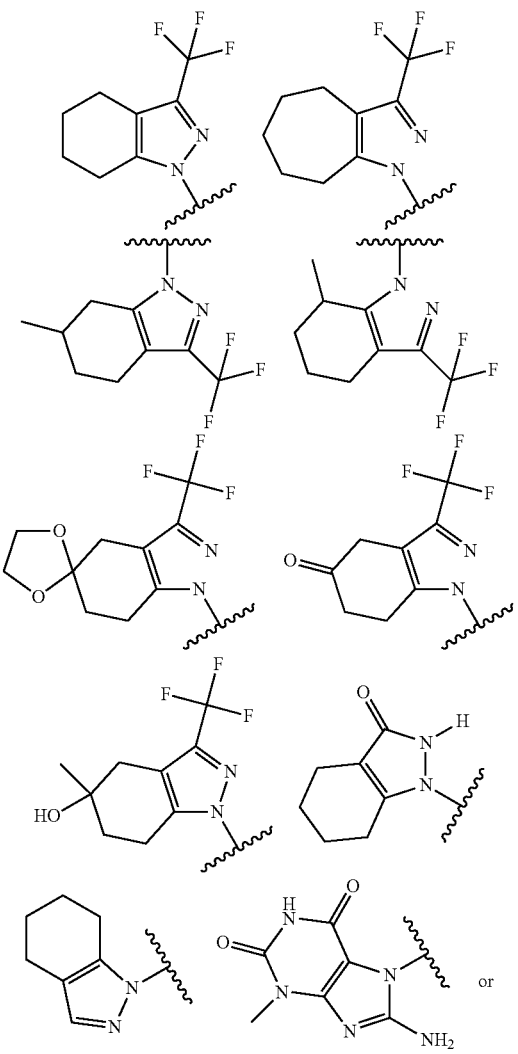

25. The compound of claim 1, or a pharmaceutically acceptable salt thereof, wherein $R^1$ is phenyl or 5-6 membered monocyclic heteroaryl, wherein any phenyl or 5-6 membered monocyclic heteroaryl of $R^1$ is optionally substituted with 1 or 2 $Z^3$ groups.

26. The compound of claim 1, or a pharmaceutically acceptable salt thereof, wherein $R^1$ is phenyl, wherein the phenyl is optionally substituted with 1 or 2 $Z^3$ groups.

27. The compound of claim 1, or a pharmaceutically acceptable salt thereof, wherein each $Z^3$ is independently $(C_1-C_6)$alkyl, halo, —CN, —$NO_2$, or —$C(O)NR^{q3}R^{r3}$, wherein any $(C_1-C_6)$alkyl of $Z^3$ is optionally substituted with 1, 2, or 3 halo groups.

28. The compound of claim 1, or a pharmaceutically acceptable salt thereof, wherein each $Z^3$ is independently methyl, fluoro, bromo, chloro, CN, $NO_2$, —$C(O)NH_2$, or —$CF_3$.

29. The compound of claim 1, or a pharmaceutically acceptable salt thereof, wherein each $Z^3$ is fluoro.

30. The compound of claim 1, or a pharmaceutically acceptable salt thereof, wherein $R^1$ is:

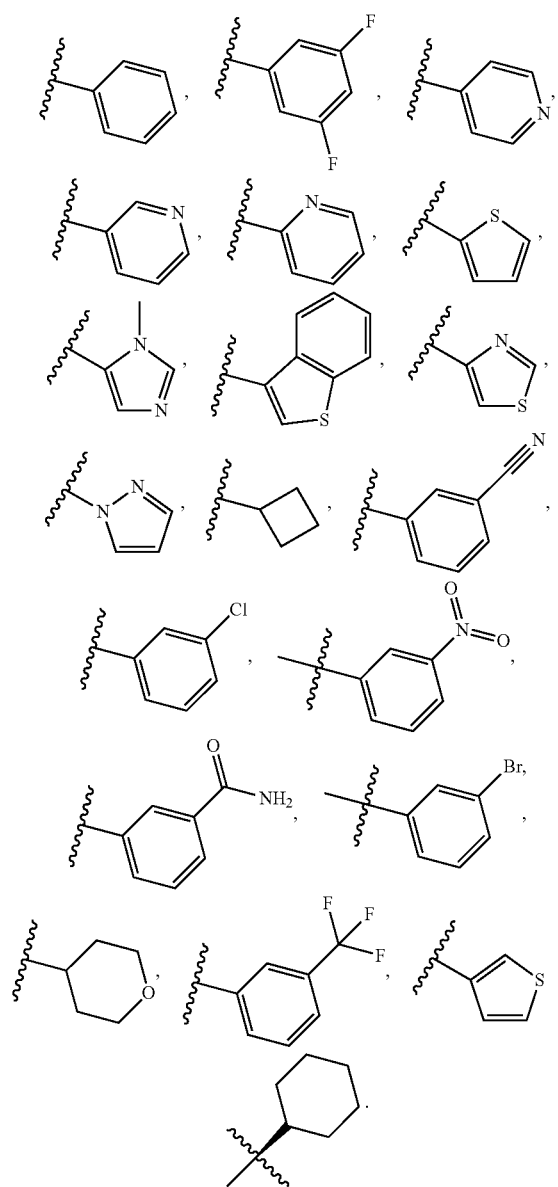

31. The compound of claim 1, or a pharmaceutically acceptable salt thereof, wherein $R^2$ is $(C_1-C_6)$alkyl.

32. The compound of claim 1, or a pharmaceutically acceptable salt thereof, wherein $R^2$ is methyl.

33. The compound of claim 1, or a pharmaceutically acceptable salt thereof, wherein $R^3$ is phenyl, 9-10 membered bicyclic aryl, or 8-10 membered bicyclic heterocycle, wherein any phenyl, 9-10 membered bicyclic aryl or 8-10 membered bicyclic heterocycle of $R^3$ is optionally substituted with 1 $Z^4$ group.

34. The compound of claim 1, or a pharmaceutically acceptable salt thereof, wherein $R^3$ is phenyl or 9-10 membered bicyclic aryl, wherein any phenyl or 9-10 membered bicyclic aryl of $R^3$ is optionally substituted with 1 $Z^4$ group.

35. The compound of claim 1, or a pharmaceutically acceptable salt thereof, wherein $R^3$ is phenyl, naphthyl or isoindolin-1-one, wherein any phenyl, naphthyl, or isoindolin-1-one of $R^3$ is optionally substituted with 1 $Z^4$ group.

36. The compound of claim 1, or a pharmaceutically acceptable salt thereof, wherein each $Z^4$ is independently $(C_1-C_6)$alkyl, halo, —CN, —$OR^{n4}$, —$NR^{q4}R^{r4}$, or oxo, wherein any $(C_1-C_6)$alkyl of $Z^4$ is optionally substituted with 1, 2, or 3 halo groups.

37. The compound of claim 1, or a pharmaceutically acceptable salt thereof, wherein each $Z^4$ is independently $(C_1-C_6)$alkyl, halo, —CN, —$O(C_1-C_6)$alkyl, —$N((C_1-C_6)$alkyl$)_2$, or oxo.

38. The compound of claim 1, or a pharmaceutically acceptable salt thereof, wherein each $Z^4$ is independently methyl, —$OCH_3$, fluoro, chloro, —$N(CH_3)_2$, or oxo.

39. The compound of claim 1, or a pharmaceutically acceptable salt thereof, wherein $R^3$ is:

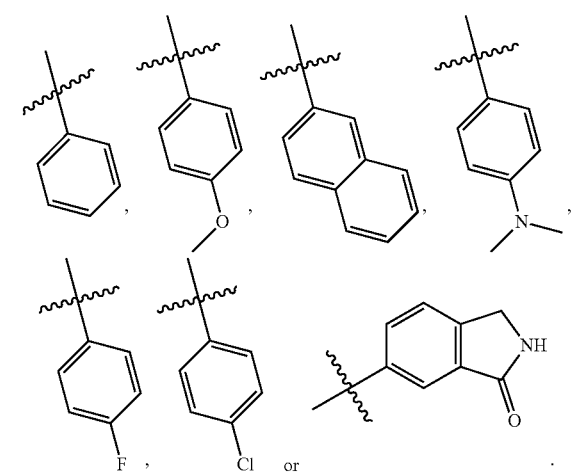

40. The compound of claim 1, or a pharmaceutically acceptable salt thereof, which is:

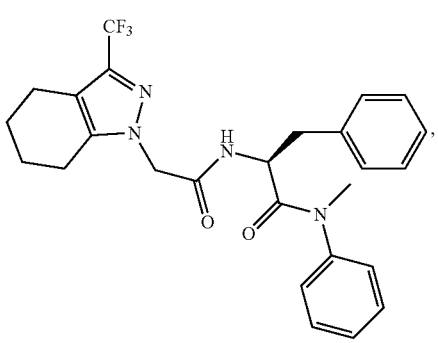

115
-continued
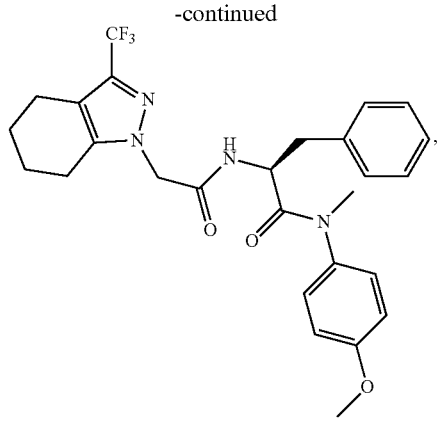
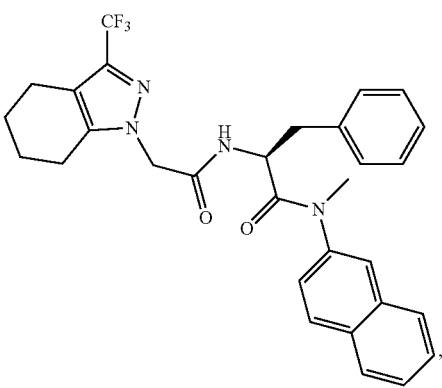
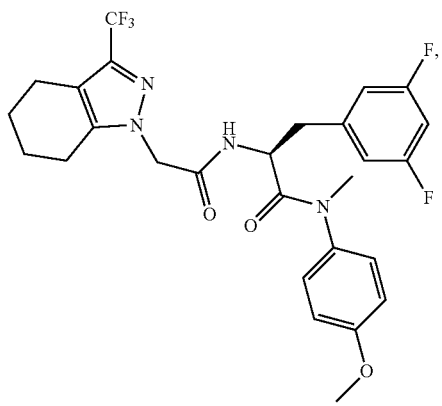
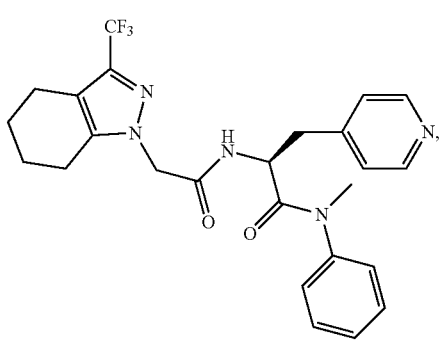
116
-continued
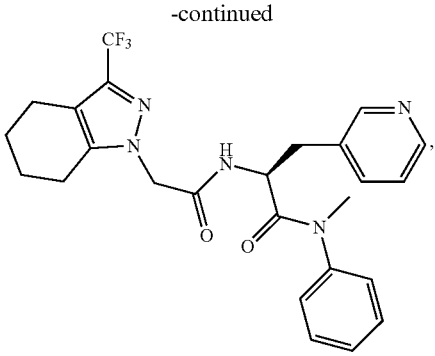
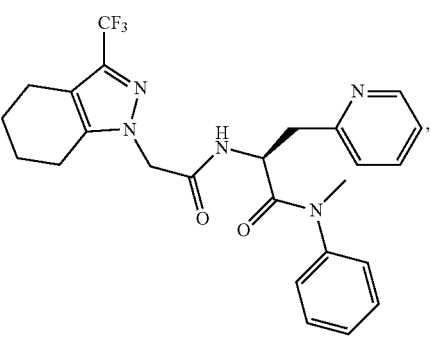
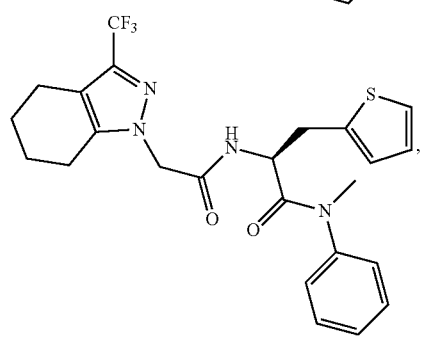
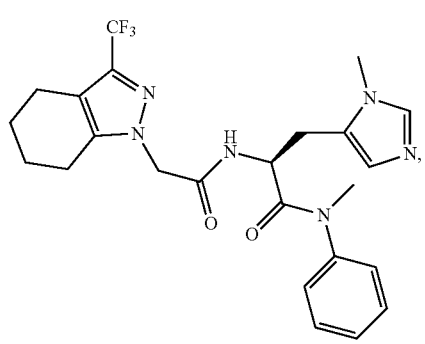
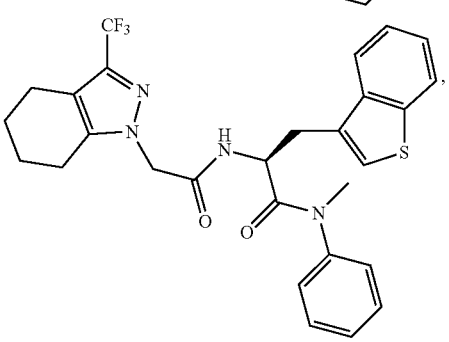

117
-continued
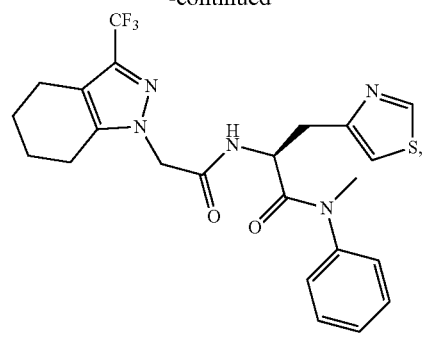
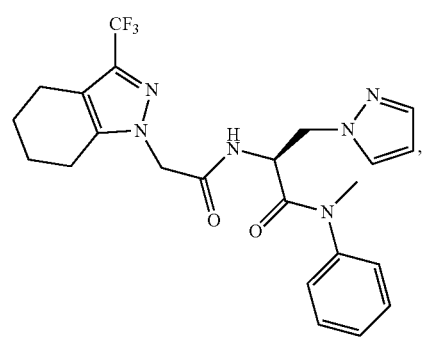
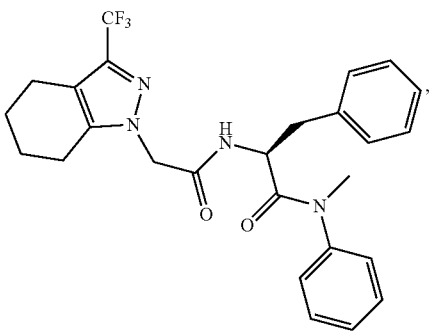
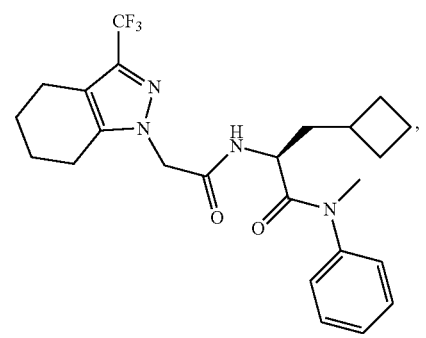
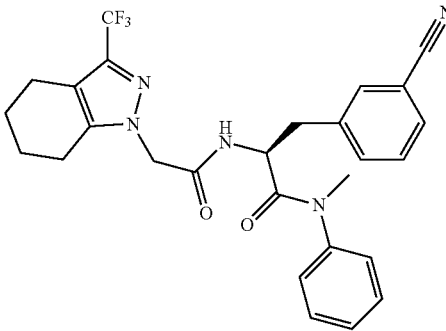
118
-continued
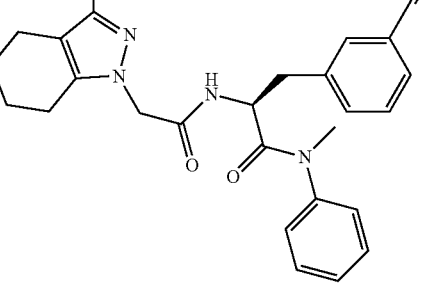

119
-continued
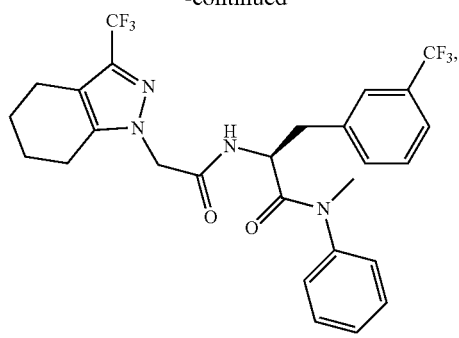
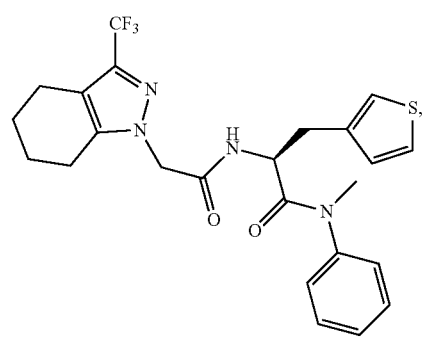
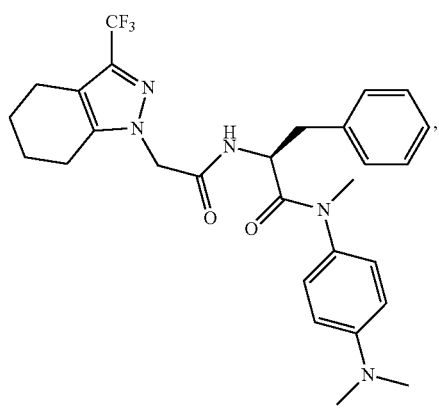
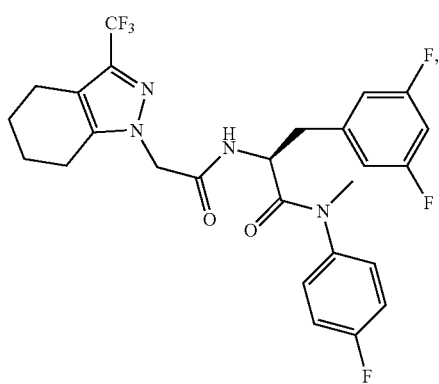
120
-continued
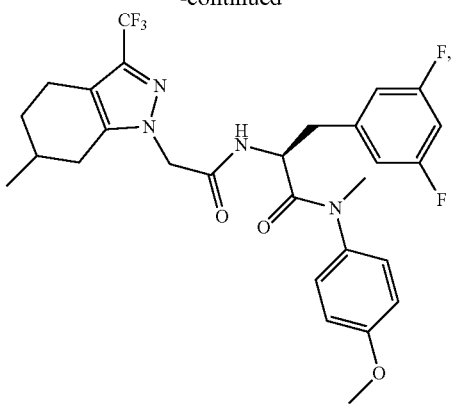
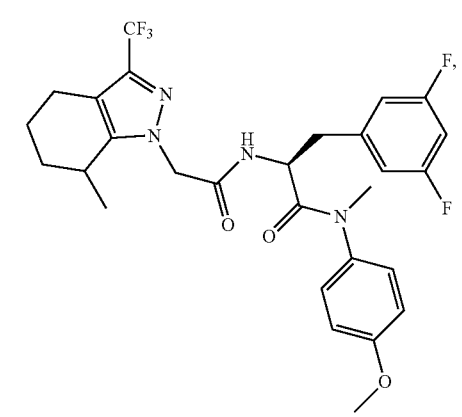
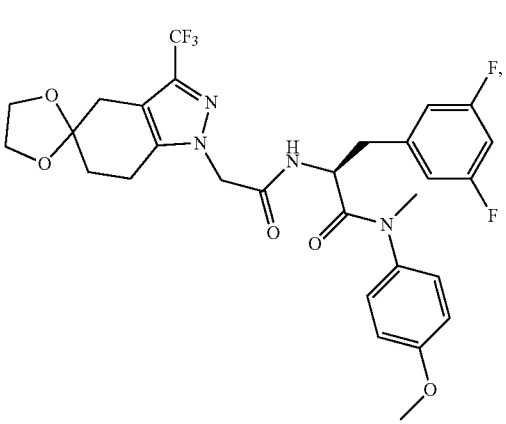
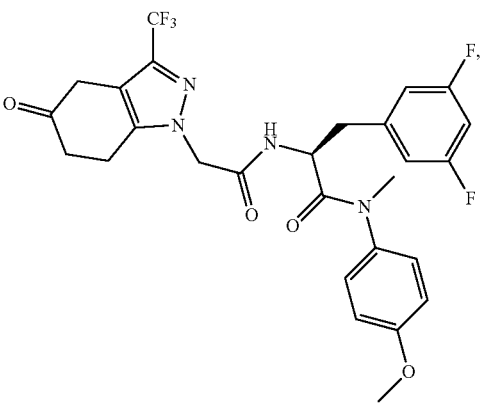

121
-continued
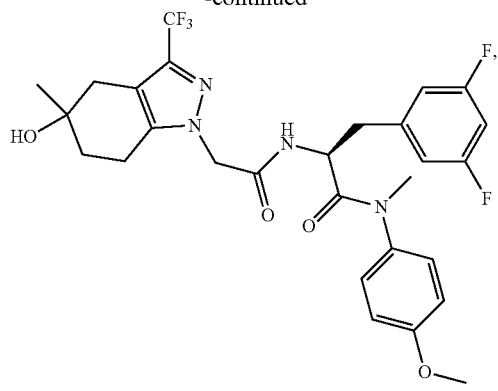
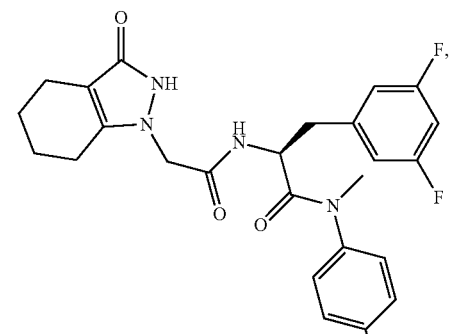
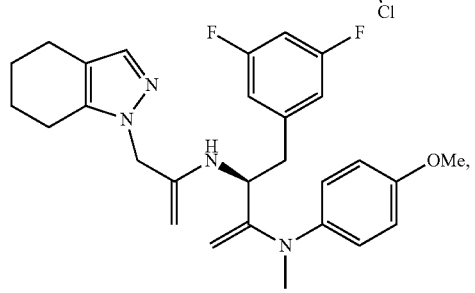
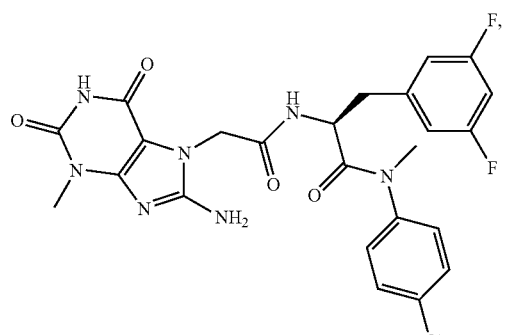
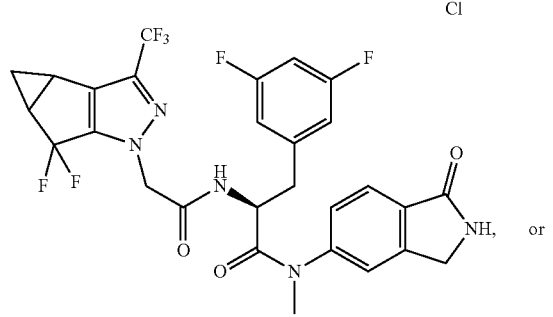
122
-continued
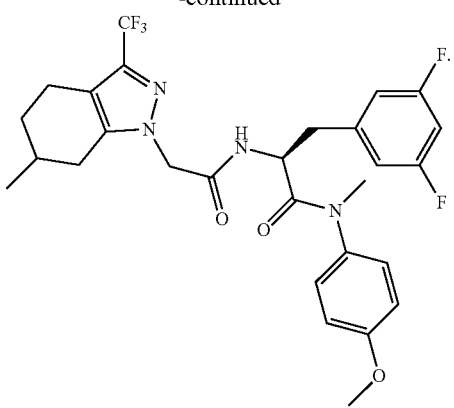
41. The compound of claim 1, or a pharmaceutically acceptable salt thereof, which is:
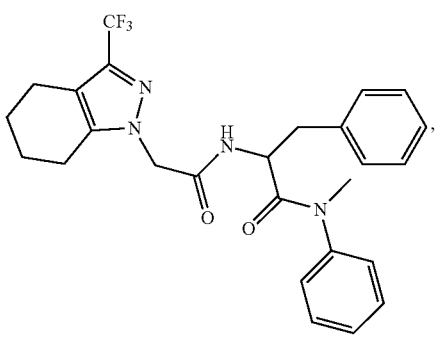
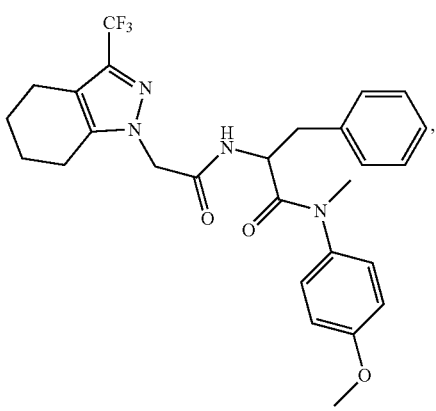
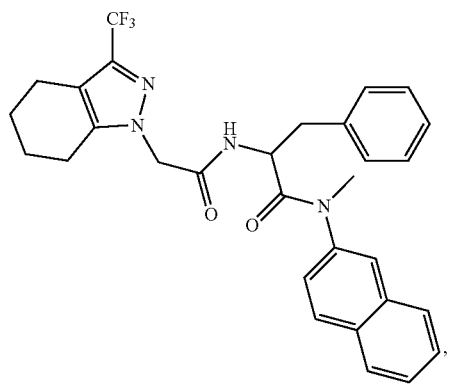

123
-continued
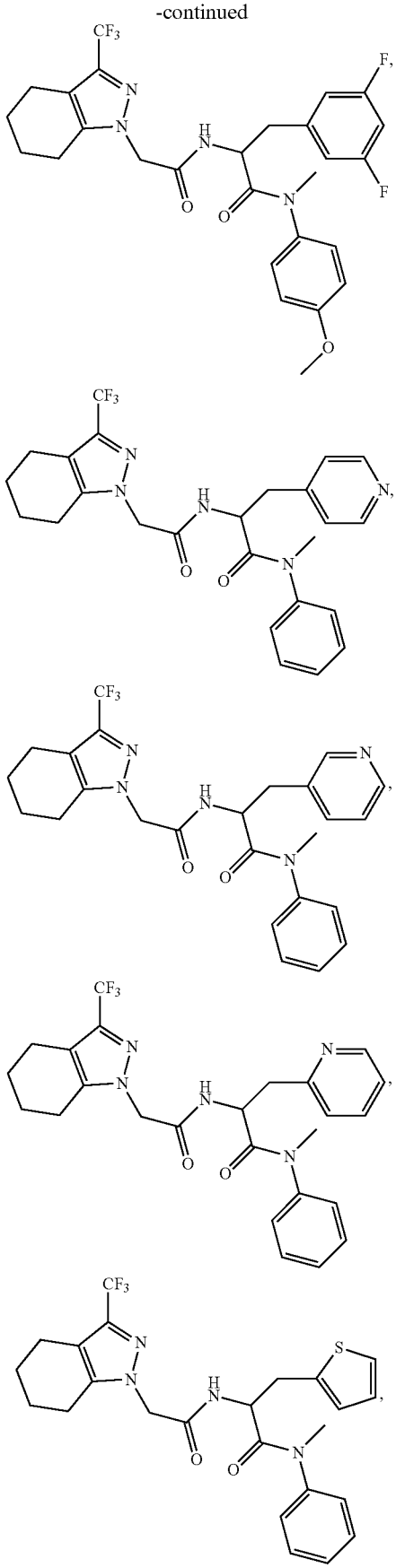
124
-continued
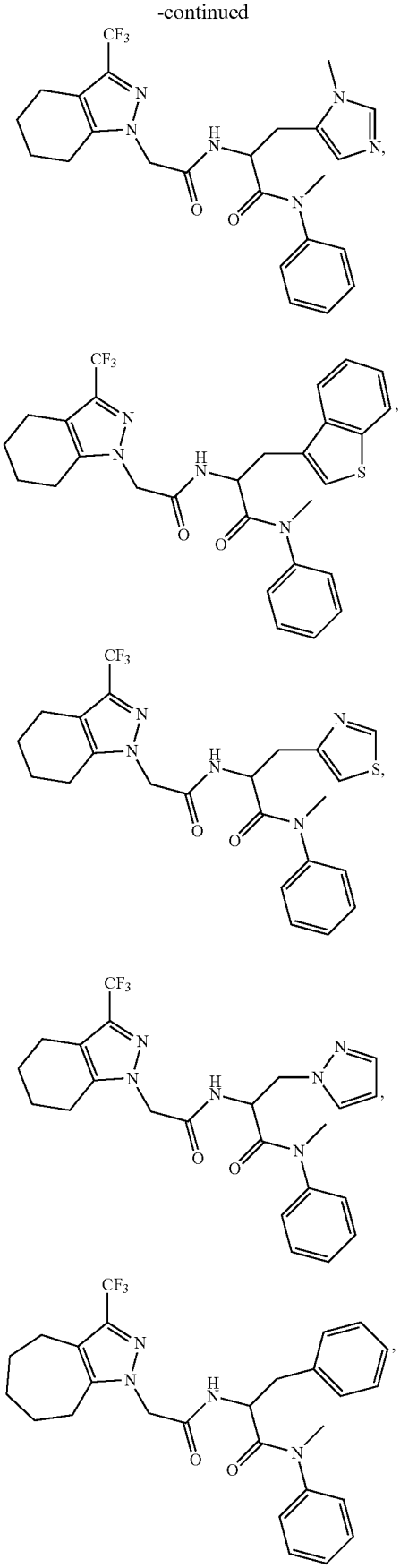

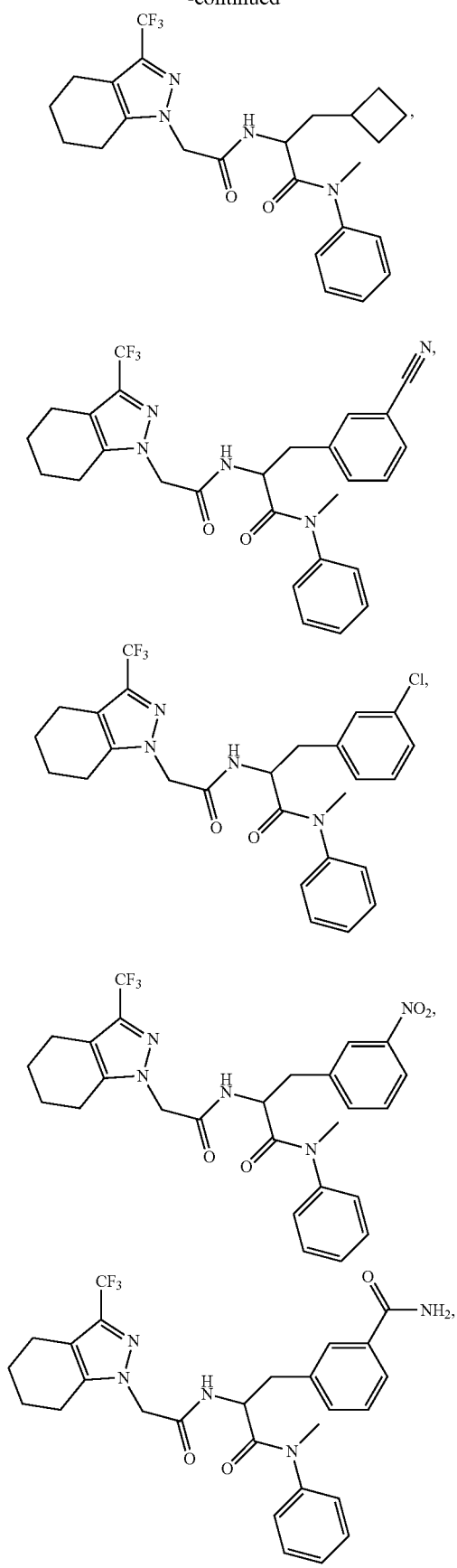
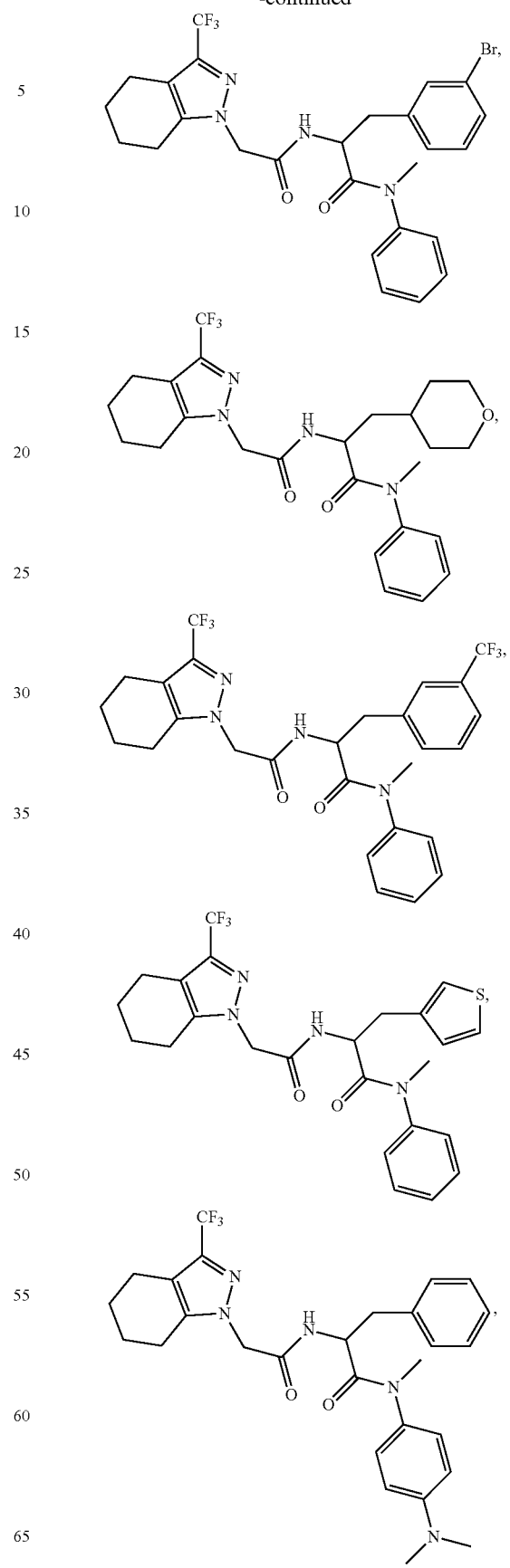

127
-continued
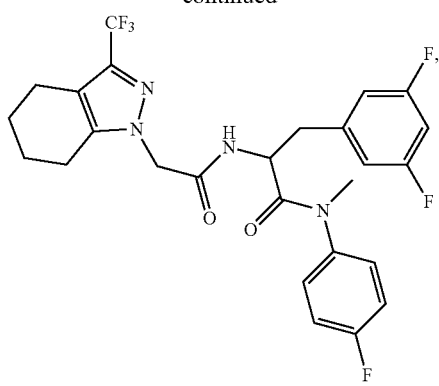
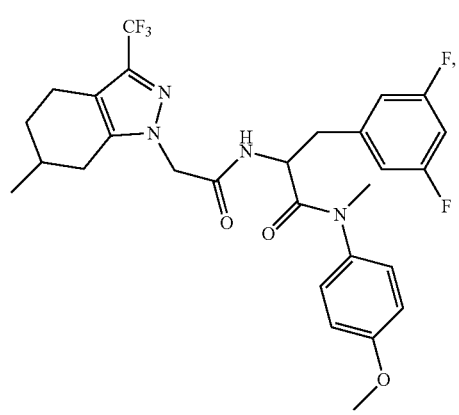
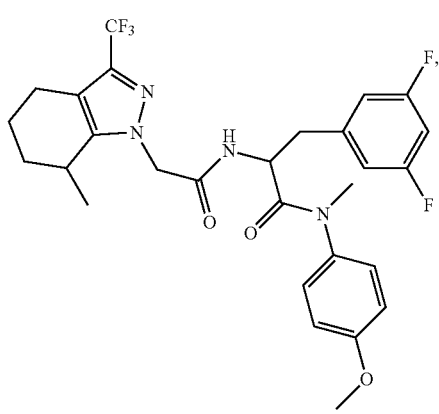
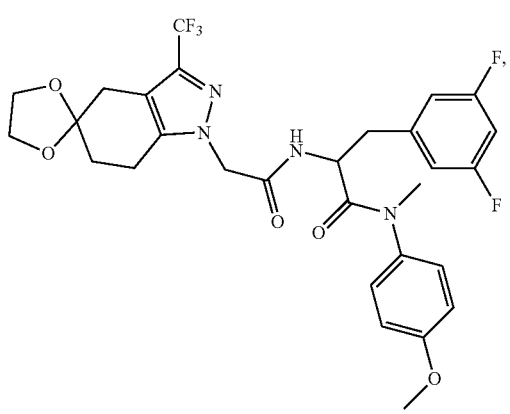
128
-continued
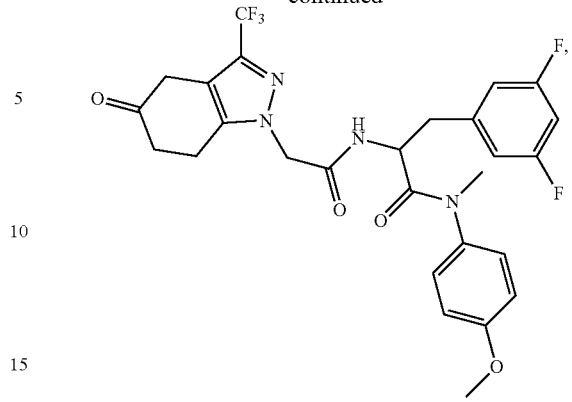
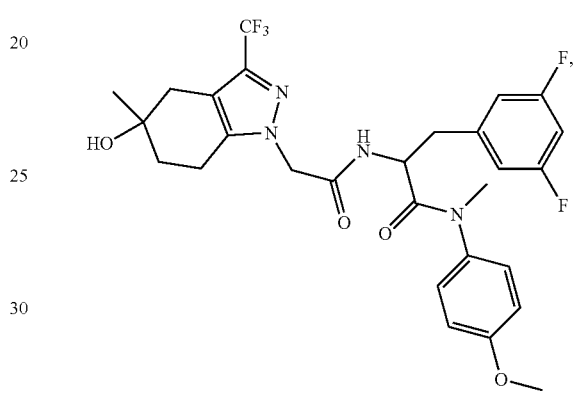
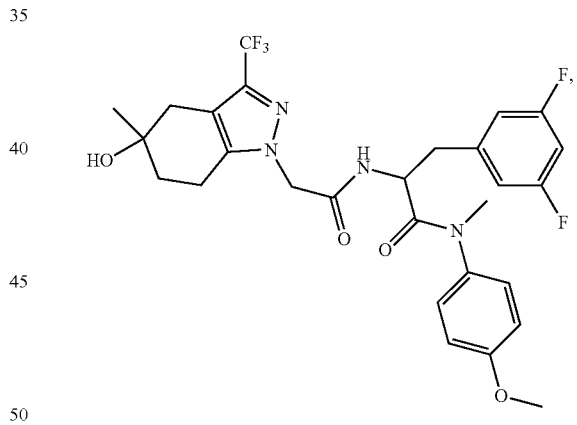
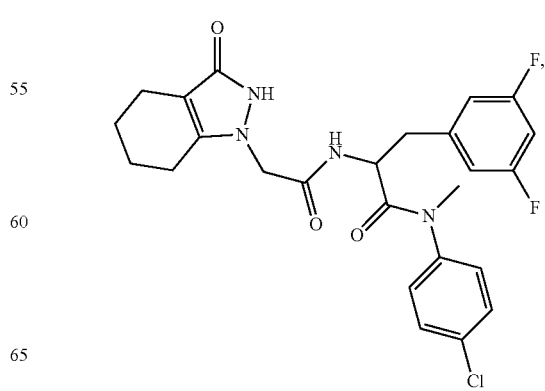

-continued

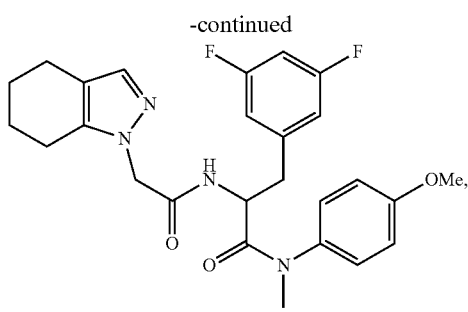

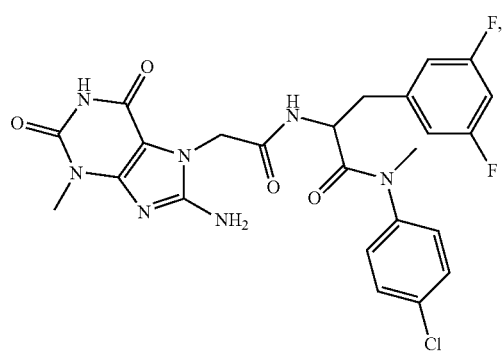

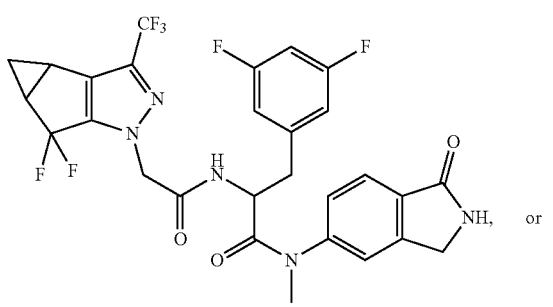

-continued

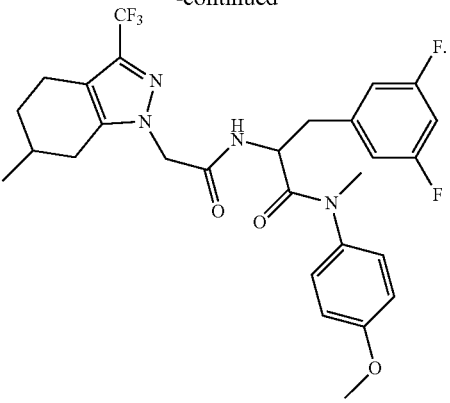

or

42. A pharmaceutical composition comprising a compound of Formula I of claim 1, or a pharmaceutically acceptable salt thereof, and a pharmaceutically acceptable carrier.

43. A pharmaceutical composition comprising a compound of claim 1, or a pharmaceutically acceptable salt thereof, and an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase inhibitor and combinations thereof.

44. A method for treating an HIV infection in a patient in need thereof comprising administering a therapeutically effective amount of a compound of claim 1, or a pharmaceutically acceptable salt thereof, to the patient.

45. A method for treating an HIV infection in a patient in need thereof comprising administering to the patient in need thereof a therapeutically effective amount of a compound of Formula I of claim 1, or a pharmaceutically acceptable salt thereof, in combination with a therapeutically effective amount of an additional therapeutic agent, wherein the additional therapeutic agent is an HIV protease inhibiting compound, an HIV non-nucleoside inhibitor of reverse transcriptase, an HIV nucleoside inhibitor of reverse transcriptase, an HIV nucleotide inhibitor of reverse transcriptase, an HIV integrase inhibitor, a gp41 inhibitor, a CXCR4 inhibitor, a gp120 inhibitor, a CCR5 inhibitor, a capsid polymerization inhibitor, or a non-catalytic site HIV integrase site inhibitor and combinations thereof.

* * * * *